US010988748B2

United States Patent
Pultz et al.

(10) Patent No.: US 10,988,748 B2
(45) Date of Patent: *Apr. 27, 2021

(54) COMPOSITIONS AND METHODS FOR TREATING CELIAC SPRUE DISEASE

(71) Applicants: UNIVERSITY OF WASHINGTON, Seattle, WA (US); The Regents of the University of California, Oakland, CA (US)

(72) Inventors: Ingrid Swanson Pultz, Seattle, WA (US); Clancey Wolf, Seattle, WA (US); Justin Bloomfield Siegel, Seattle, WA (US); Christine Elaine Tinberg, Seattle, WA (US); Lance Stewart, Seattle, WA (US); David Baker, Seattle, WA (US)

(73) Assignees: University of Washington, Seattle, WA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/719,183

(22) Filed: Dec. 18, 2019

(65) Prior Publication Data

US 2020/0109387 A1  Apr. 9, 2020

Related U.S. Application Data

(63) Continuation of application No. 15/575,159, filed as application No. PCT/US2016/036356 on Jun. 8, 2016, now Pat. No. 10,793,846.

(60) Provisional application No. 62/172,557, filed on Jun. 8, 2015.

(51) Int. Cl.
*C12N 9/50* (2006.01)
*C12N 9/52* (2006.01)
*A61K 38/00* (2006.01)
*A61P 1/14* (2006.01)

(52) U.S. Cl.
CPC .......... *C12N 9/50* (2013.01); *A61P 1/14* (2018.01); *C12N 9/52* (2013.01); *A61K 38/00* (2013.01)

(58) Field of Classification Search
None
See application file for complete search history.

(56) References Cited

U.S. PATENT DOCUMENTS

| 5,554,508 | A | 9/1996 | Auriol et al. |
|---|---|---|---|
| 7,202,216 | B2 | 4/2007 | Sollid et al. |
| 7,265,093 | B2 | 9/2007 | Khosla et al. |
| 7,303,871 | B2 | 12/2007 | Hausch et al. |
| 7,320,788 | B2 | 1/2008 | Shan et al. |
| 7,462,688 | B2 | 12/2008 | Khosla et al. |
| 7,534,426 | B2 | 5/2009 | Piper et al. |
| 7,563,864 | B2 | 7/2009 | Marti et al. |
| 7,579,313 | B2 | 8/2009 | Khosla et al. |
| 7,605,150 | B2 | 10/2009 | Khosla et al. |
| 7,628,985 | B2 | 12/2009 | Shan et al. |
| 7,776,545 | B2 | 8/2010 | Khosla et al. |
| 7,910,541 | B2 | 3/2011 | Hausch et al. |
| 7,923,532 | B2 | 4/2011 | Hausch et al. |
| 7,928,056 | B2 | 4/2011 | Hausch et al. |
| 7,943,312 | B2 | 5/2011 | Hausch et al. |
| 8,071,316 | B2 | 12/2011 | Khosla et al. |
| 8,143,210 | B2 | 3/2012 | Shan et al. |
| 8,153,593 | B2 | 4/2012 | Khosla et al. |
| 8,426,145 | B2 | 4/2013 | Khosla et al. |
| 8,470,782 | B2 | 6/2013 | Khosla et al. |
| 8,796,201 | B2 | 8/2014 | Shan et al. |
| 8,871,718 | B2 | 10/2014 | Khosla et al. |
| 8,962,545 | B2 | 2/2015 | Hausch et al. |
| 9,707,280 | B2 * | 7/2017 | Siegel ..................... C12N 9/52 |
| 10,266,815 | B2 | 4/2019 | Siegel |
| 10,487,318 | B1 | 11/2019 | Siegel |
| 2006/0269538 | A1 | 11/2006 | Kolterman et al. |
| 2009/0117092 | A1 | 5/2009 | Kappler et al. |
| 2009/0280555 | A1 | 11/2009 | Hausch et al. |
| 2011/0171201 | A1 | 7/2011 | Siegel et al. |

(Continued)

FOREIGN PATENT DOCUMENTS

| JP | 2002078489 | 3/2002 |
|---|---|---|
| WO | 2013/023151 | 2/2013 |
| WO | 2013/083338 A1 | 6/2013 |

(Continued)

OTHER PUBLICATIONS

Akobeng, et al., "Systematic review: tolerable amount of gluten for people with coeliac disease," Alimentary Pharmacology & Therapeutics, 27: 1044-1052 (2008).
Arentz-Hansen, et al., "The Intestinal T Cell Response to a-Gliadin in Adult Celiac Disease Is Focused on a Single Deamidated Glutamine Targeted by Tissue Transglutaminase," J. Exp. Med., 191(4): 603-612, 2000.
Armstrong, et al., "Advances in coeliac disease," Curr Opin Gastroenterol 2012, 28:104-112.
Arnold, "Combinatorial and computational challenges for biocatalyst design," Nature, 409: 253-257, Jan. 2001.
Bershtein, et al., "Advances in laboratory evolution of enzymes," Current Opinion in Chemical Biology 2008, 12:151-158.

(Continued)

*Primary Examiner* — Patricia Duffy
(74) *Attorney, Agent, or Firm* — McDonnell Boehnen Hulbert & Berghoff LLP

(57) ABSTRACT

Polypeptides, and methods for their use, are disclosed that have an amino acid sequence at least 75% identical to the amino acid sequence of SEQ ID NO:1, are provided, wherein (a) the polypeptide degrades a PFQPQLPY (SEQ ID NO: 140) peptide and/or a PFPQPQQPF (SEQ ID NO: 68) at pH 4; (b) residue 467 is Ser, residue 267 is Glu, and residue 271 is Asp; and (c) the polypeptide comprises an amino acid change from SEQ ID NO: 1 at one or more residues selected from the group consisting of 221, 262E, 268, 269, 270, 319A, 320, 354E/Q/R/Y, 358S/Q/T, 368F/Q, 399, 402, 406, 424, 449, 461, 463, 105, 171, 172, 173, 174, and 456.

2 Claims, 8 Drawing Sheets

Specification includes a Sequence Listing.

(56) References Cited

U.S. PATENT DOCUMENTS

2011/0293724 A1  12/2011  Hausch et al.

FOREIGN PATENT DOCUMENTS

| WO | 2015/023728 |   | 2/2015 |
|----|-------------|---|--------|
| WO | 2016/200880 | * | 12/2016 |

OTHER PUBLICATIONS

Bethune, et al., "Heterologous Expression, Purification, Refolding, and Structural-Functional Characterization of EP-B2, a Self-Activating Barley Cysteine Endoprotease," Chemistry & Biology 13, 637-647, Jun. 2006.

Bethune, et al., "Oral Enzyme Therapy for Celiac Sprue," Methods in Enzymology, 502: 241-270, 2012.

Camacrca, et al., "Intestinal T Cell Responses to Gluten Peptides Are Largely Heterogeneous: Implications for a Peptide-Based Therapy in Celiac Disease," The Journal of Immunology, 2009, 4158-4166.

Castillo, et al., "The present and the future in the diagnosis and management of celiac disease," Gastroenterology Report, 3(1), 2015, 3-11.

Catassi, et al., "World Perspective and Celiac Disease Epidemiology," Dig Dis 2015;33:141-146.

Catassi, et al., "A prospective, double-blind, placebo-controlled trial to establish a safe gluten threshold for patients with celiac disease," Am J Clin Nutr 2007;85:160-6.

Chand, et al., "Celiac Disease Current Concepts in Diagnosis and Treatment," J Clin Gastroenterol 2006;40:3-14.

Chang, et al., "A Novel Placement Method of the Bravo Wireless pH Monitoring Capsule for Measuring Intragastric pH," Dig Dis Sci (2009) 54:578-585.

Ehern, et al., "A Food-Grade Enzyme Preparation with Modest Gluten Detoxification Properties," PLoS One 4(7): e6313. doi:10.1371/journal.pone.0006313, Jul. 2009.

Ehern, et al., "Protein engineering of improved prolyl endopeptidases for celiac sprue therapy," Protein Engineering, Design & Selection vol. 21 No. 12 pp. 699-707, 2008.

Eiben, et al., "Increased Diels-Alderase activity through backbone remodeling guided by Foldit players," Nature Biotechnology, 30(2): 190-194, 2012.

Fleishman, et al., "Computational Design of Proteins Targeting the Conserved Stem Region of Influenza Hemagglutinin," Science, 332:816-821, May 2011.

Gardner, et al., Measurement of meal-stimulated gastric acid secretion by in vivo gastric autotitration, J Appl Physiol 92: 427-434, 2002.

Gass, et al., "Combination Enzyme Therapy for Gastric Digestion of Dietary Gluten in Patients With Celiac Sprue," Gastroenterology 2007;133:472-480.

Gass, et al., "Effect of Barley Endoprotease EP-B2 on Gluten Digestion in the Intact Rat," The Journal of Pharmacology and Experimental Therapeutics vol. 318, No. 3, pp. 1178-1186, 2006.

Arentz-Hansen et al. (Sep. 2002) "Celiac lesion T cells recognize epitopes that cluster in regions of gliadins rich in proline residues," Gastroenterology, 123(3):803-809.

Hausch, et al., "Intestinal digestive resistance of immunodominant gliadin peptides," Am J Physiol Gastrointest Liver Physiol 283: G996-G1003, 2002.

Houghton, et al., "Relationship of the Motor Activity of the Antrum, Pylorus, and Duodenum to Gastric Emptying of a Solid Liquid Mixed Meal," Gatroenterology, 1988; 94:1285-91.

International Search Report PCT/US2012/050364, dated Apr. 18, 2013.

International Search Report PCT/US2014/050835, dated Dec. 2, 2014.

Kuhlman, et al., "Design of a Novel Globular Protein Fold with Atomic-Level Accuracy," Science, 302: 1364-1368, Nov. 2003.

Kunkel, "Rapid and efficient site-specific mutagenesis without phenotypic selection," Proc. Natl. Acad. Sci. USA vol. 82, pp. 488-492, Jan. 1985.

Lahdeaho, et al., "Glutenase ALV003 Attenuates Gluten-Induced Mucosal Injury in Patients With Celiac Disease," Gastroenterology 2014;146:1649-1658.

Leaver-Fay, et al., "ROSETTA3: An Object-Oriented Software Suite for the Simulation and Design of Macromolecules," Methods in Enzymology, vol. 487:545-574, 2011.

Lupo, et al., "Validation Study of the Veratox R5 Rapid ELISA for Detection of Gliadin," Journal of AOA C International vol. 96, No. 1, 2013.

Moron, et al., "Sensitive detection of cereal fractions that are toxic to celiac disease patients by using monoclonal antibodies to a main immunogenic wheat peptide," Am J Clin Nutr 2008;87:405-14.

Mustalahti, et al., "The prevalence of celiac disease in Europe: Results of a centralized, international mass screening project," Annals of Medicine, 42:8, 587-595, Nov. 2010.

Oda, et al., "Subsite Preferences of Pepstatin-Insensitive Carboxyl Proteinases from Prokaryotes: Kumamolysin, a Thermostable Pepstatin-Insensitive Carboxyl Proteinase," J. Biochem. 128,499-607 (2000).

Okubo, et al., "Processing, catalytic activity and crystal structures of kumamolisin-As with an engineered active site," FEBS Journal 273 (2006) 2563-2576.

Siegel et al. (Jul. 2010) "Computational Design of an Enzyme Catalyst for a Stereoselective Bimolecular Diels-Alder Reaction," Science, 329(5989):309-313.

Pera, et al., "Influence of Mastication on Gastric Emptying," J Dent Res 81(3):179-181, 2002.

Petersen, et al., "T-cell receptor recognition of HLA-DQ2-gliadin complexes associated with celiac disease," Nature Structural & Molecular Biology, 21(5): 480-490, May 2014.

Picariello, et al., "Proteomics, Peptidomics, and Immunogenic Potential of Wheat Beer (Weissbier)," J. Agric. Food Chem. 2015, 63, 3579-3586.

Richter, et al., "De Novo Enzyme Design Using Rosetta3," PLoS One 6(5): e19230. doi:10.1371/journal.pone.0019230, May 2011.

Romero, et al., "Exploring protein fitness landscapes by directed evolution," Nature Reviews: Molecular cell Biology, 10: 866-876, Dec. 2009.

Rubio-Tapia, et al., "The Prevalence of Celiac Disease in the United States," Am J Gastroenterol 2012; 107:1538-1544; doi: 10.1038/ajg.2012.219; published online Jul. 31, 2012.

Shan, et al., "Comparative biochemical analysis of three bacterial prolyl endopeptidases: implications for coeliac sprue," Biochem. J. (2004) 383, 311-318.

Shan, et al., "Identification and Analysis of Multivalent Proteolytically Resistant Peptides from Gluten: Implications for Celiac Sprue," Journal of Proteome Research 2005, 4, 1732-1741.

Shan, et al., "Structural Basis for Gluten Intolerance in Celiac Sprue," Science, 297:2275-2279, Sep. 2002.

Siegel, et al., "Rational Design of Combination Enzyme Therapy for Celiac Sprue," Chemistry & Biology 13, 649-658, Jun. 2006.

Siegel, et al., "Safety, Tolerability, and Activity of ALV003: Results from Two Phase 1 Single, Escalating-Dose Clinical Trials," Dig Dis Sci (2012) 57:440-450.

Sollid, et al., "Nomenclature and listing of celiac disease relevant gluten T-cell epitopes restricted by HLA-DQ molecules," Immunogenetics (2012) 64:455-460.

Sollid, et al., "Coeliac Disease: Dissecting a Complex Inflammatory Disorder," Nature Reviews: Immunology, 2:847-855, Sep. 2002.

Stepniak, et al., "Highly efficient gluten degradation with a newly identified prolyl endoprotease: implications for celiac disease," Am J Physiol Gastrointest Liver Physiol 291: G621-G629, May 2006.

Tye-Din, et al., "Comprehensive, Quantitative Mapping of T Cell Epitopes in Gluten in Celiac Disease," Sci Transl Med 2, 41ra51 (2010).

Office Action dated Dec. 23, 2015 in EP 12748354.3.

Wlodawer A, M Li, A Gustchina, N Tsuruoka, M Ashida, H Minakata, H Oyama, K Oda, T Nishino, and T Nakayama. 2004. "Crystallographic and biochemical investigations of kumamolisin-As, a serine-carboxyl peptidase with collagenase activity". The Journal of Biological Chemistry. 279 (20): 21500-10.

(56) References Cited

OTHER PUBLICATIONS

Vora Harmit, et al., (2007) "A scaleable manufacturing process for pro-EP-B2, a cysteine protease from barley indicated for celiac psrue," Biotechnology and Bioengineering, 98(1): 177-185.
Dunn, et al., "Engineered Enzyme," Encyclopedia of Life Sciences, 2005, p. 1-8.
Wieser, "Chemistry of gluten proteins," Food Microbiology 24 (2007) 115-119.
GenBank: BAC41257.1, kumamolisin-As precursor, Jun. 2003.
Uniprot C8WU40—Retrieved from ,http://www.uniprot.org/uniprot/C8WU40> on Jan. 29, 2015.
Cornellas-Bigler, et al., "1.2 a crystal structure of the serine carboxyl porteinase pro-kumamolisin: structure of an intact pro-subtilase," Structure, 12: 1313-1323, Jul. 2004.
GenBank: 1SIO_A, Chain A, Structure of Kumamolisin-As Complex, Sep. 2008.
Genbank: ACV57803.1, Peptidase S53 propeptide, Sep. 2009.
The International Search Report (ISR) with Written Opinion for PCT/US2016/036356 dated Aug. 10, 2016, pp. 1-22.
Database UNI PARC [Online] Jan. 15, 2818 (Jan. 15, 2010), XP002760283, retrieved from EBI accession No. UNIPARC:UPI0000402017 Database accession No. UPI0000402017.

Wolf, Clancey et al. "Engineering of Kuma030: A Gliadin Peptidase That Rapidly Degrades Immunogenic Gliadin Peptides in Gastric Conditions" A Journal of the American Chemical Society (2015) vol. 137, pp. 13106-13113.
Gordon, Sydney R. et al. "Computational Design of an [alpha]-Gliadin Peptidase" Journal of the American Chemical Society (2012) vol. 134(50), pp. 20513-20520.
Oyama, Hiroshi et al. "A CLN2-related and thermostable serine-carboxyl proteinase kumamolysin: cloning, expression, and identification of catalytic serine residue" Journal of Biochemistry (2002) vol. 131, pp. 757-765.
UniProt K8RML0_9BURK, Feb. 6, 2013.
Houghten et al. (Vaccines, 1986, Edited by Fred Brown: Cold Spring Harbor Laboratory) (Year: 1886).
Byun et al. "Synergistic Action of an X-Prolyl Dipeptidyl Amino-peptidase and a Non-Specific Aminopeptidase in Protein Hydrolysis" J Agric. Food Chem. 49:2061-63 (2001).
Genbank accession No. ACU54006.1 "Peptidase S53 propeptide [Acidimicrobium ferrooxidans DSM 10331]" (Genbank accession No. ACU54006.1, publically available since Aug. 18, 2009, retrieved from the internet: (https://www.ncbi.nlm.nih.gov/protein/ACU54006?report=genbank&log$=pro-.align&blast_rank=18LRID=E6Z6PR8P015, retrieved on Apr. 27, 2018).
GenPept: PDB 4NE7_A Chain A, Kumamolisin-as; pp. 1-4, Nov. 2013.

* cited by examiner

A

Degradation of 33mer Peptide:
Appearance of LPYPQPQPF Breakdown Product

B

Degradation of 26mer Peptide:
Appearance of FLQPQ Breakdown Product

COMPOSITIONS AND METHODS FOR TREATING CELIAC SPRUE DISEASE

CROSS REFERENCE

This application is a continuation of U.S. application Ser. No. 15/575,159 filed Nov. 17, 2017, which is a national stage filing of PCT Application Serial No. PCT/US2016/036356 filed Jun. 8, 2016, which claims priority to U.S. Provisional Patent Application Ser. No. 62/172,557 filed Jun. 8, 2015, each incorporated by reference herein in its entirety.

BACKGROUND

Celiac sprue is a highly prevalent disease in which dietary proteins found in wheat, barley, and rye products known as 'glutens' evoke an immune response in the small intestine of genetically predisposed individuals. The resulting inflammation can lead to the degradation of the villi of the small intestine, impeding the absorption of nutrients. Symptoms can appear in early childhood or later in life, and range widely in severity, from diarrhea, fatigue and weight loss to abdominal distension, anemia, and neurological symptoms. There are currently no effective therapies for this lifelong disease except the total elimination of glutens from the diet. Although celiac sprue remains largely underdiagnosed, its' prevalence in the US and Europe is estimated at 0.5-1.0% of the population. In addition to celiac sprue, a significant fraction of the population is thought to suffer from the condition of non-celiac gluten sensitivity (NCGS), which is caused by the ingestion of gluten but is mechanistically distinct from celiac disease, though the symptoms are frequently indistinguishable from those of celiac sprue. The identification of suitable naturally-occurring enzymes as oral therapeutics for celiac disease and NCGS is difficult due to the stringent physical and chemical requirements to specifically and efficiently degrade gluten-derived peptides in the harsh and highly acidic environment of the human digestive tract. Since gluten peptides initiate the immune response immediately upon entering the intestines, it is imperative that any oral enzyme therapeutic for celiac disease break down these immunogenic gluten regions in the gastric compartment, thereby preventing these gluten peptides from causing intestinal damage due to inflammation.

SUMMARY OF THE INVENTION

In one aspect, the invention provides polypeptides comprising an amino acid sequence at least 75%, 80%, 85%, 90%, 95%, or more identical to the amino acid sequence of SEQ ID NO: 1, wherein
  (a) residue 467 is Ser, residue 267 is Glu, and residue 271 is Asp; and
  (b) the polypeptide comprises an amino acid change from SEQ ID NO: 1 at one or more residues selected from the group consisting of 463, 221, 262E, 268, 269, 270, 319A, 320, 354E/Q/R/Y, 358S/Q/T, 368F/Q, 399, 402, 406, 424, 449, 461, 105, 171, 172, 173, 174, and 456.

In one embodiment, the polypeptide comprises an amino acid change from SEQ ID NO: 1 at one or more residues selected from the group consisting of 463, 221, 262E, 268, 269, 270, 319A, 320, 354E/Q/R/Y, 358S/Q/T, 368F/Q, 399, 402, 406, 424, 449, and 461. In another embodiment, the polypeptide comprises an amino acid change from SEQ ID NO: 1 at one or more residues selected from the group consisting of 221D/N/Q/H, 262E, 268S/T/A, 269L/T, 270A/T/V, 319A, 354E/Q/R/Y, 358S/Q/T, 368F/Q, 399Q, 402S/Q, 406S, 424K, 449E/N/Q, 461R, and 463A/L/M/Q/R/T/V. In a further embodiment, the polypeptide comprises an amino acid change from SEQ ID NO: 1 at 2, 3, 4, 5, 6, 7, 8, 9, 10, 11, 12, 13 or more residues selected from the group.

In one embodiment, the polypeptide comprises amino acid changes from SEQ ID NO: 1 at residues 399 and 449, such as amino acid changes 399Q and 449Q. In another embodiment, the polypeptide comprises amino acid changes 358S and 463T. In a further embodiment, the polypeptide comprises amino acid changes 262E, 269T, 354Q, 358S, 399Q, 449Q, and 463T. In another embodiment, the polypeptide comprises amino acid changes 319A, 368F, 399Q, 449Q, and 463T. In a further embodiment, the polypeptide comprises amino acid changes 262E, 269T, 270V, 354Q, 358S, 399Q, and 449Q. In a still further embodiment, the polypeptide comprises amino acid changes 262E, 269T, 320M, 354Q, 358S, 399Q, 449Q, and 463T. In another embodiment, the polypeptide comprises amino acid changes 319A, 320M, 368F, 399Q, 449Q, and 463T. In one embodiment, the polypeptides comprise an amino acid change from SEQ ID NO: 1 at one or more amino acid positions selected from the group consisting of 105, 171, 172, 173, 174, and 456, such as amino acid changes 105H; 171R A, or S; 172R, A, or S; 173R or S, 174S, and/or 456V.

In another aspect, the invention provides polypeptide comprising an amino acid sequence at least 75%, 80%, 85%, 90%, 95%, or more identical to the amino acid sequence of SEQ ID NO: 71, wherein
  (a) residue 278 is Ser, residue 78 is Glu, and residue 82 is Asp; and
  (b) the polypeptide comprises an amino acid change from SEQ ID NO: 71 at one or more residues selected from the group consisting of 274, 32, 73E, 79, 80, 81, 130A, 165E/Q/R/Y, 169S/Q/T, 179F/Q, 210, 213, 217, 235, 260, 267, and 272.

In one embodiment, the polypeptide comprises an amino acid change from SEQ ID NO: 71 at one or more residues selected from the group consisting of 274, 32, 73E, 79, 80, 81, 130A, 165E/Q/R/Y, 169S/Q/T, 179F/Q, 210, 213, 217, 235, 260, and 272.

In one embodiment, the polypeptide comprises an amino acid change from SEQ ID NO: 71 at one or more residues selected from the group consisting of 32D/N/Q/H, 73E, 79S/T/A, 80L/T, 81A/T/V, 130A, 165E/Q/R/Y, 169S/Q/T, 179F/Q, 210Q, 2135/Q, 217S, 235K, 260E/N/Q, 272R, and 274A/L/M/Q/R/TN. In a further embodiment, the polypeptide comprises an amino acid change from SEQ ID NO: 71 at 2, 3, 4, 5, 6, 7, 8, 9, 10, 11, 12, or more residues selected from the group. In one embodiment, the polypeptide comprises amino acid changes from SEQ ID NO: 71 at residues 210 and 260, including but not limited to amino acid changes 210Q and 260Q. In another embodiment, the polypeptide comprises amino acid changes 169S and 274T. In a further embodiment, the polypeptide comprises amino acid changes 73E, 80T, 165Q, 169S, 210Q, 260Q, and 274T. In another embodiment, the polypeptide comprises amino acid changes 130A, 179F, 210Q, 260Q, and 274T. In a further embodiment, the polypeptide comprises amino acid changes 73E, 80T, 81V, 165Q, 169S, 210Q, and 260Q. In a still further embodiment, the polypeptide comprises amino acid changes 73E, 80T, 320M, 165Q, 169S, 210Q, 260Q, and 274T. In one embodiment, the polypeptide comprises amino acid changes 130A, 131M, 179F, 210Q, 260Q, and 274T. In another embodiment, the polypeptide comprises an amino acid change from SEQ ID NO: 71 at amino acid position 267, including but not limited to 267V.

In another embodiment, the polypeptide comprises the amino acid sequence selected from the group consisting of SEQ ID NOs: 2-42, 44-60 and 72-112, and 114-130 and 150-155. In a further embodiment, the polypeptide comprises the amino acid sequence selected from the group consisting of SEQ ID NOs: 2-42, 55-60 and 72-112, and 125-130 and 150-155.

In one embodiment, the polypeptides of the invention may further comprise a histidine tag at the C-terminus of the polypeptide. In another embodiment, the histidine tag comprises a cleavable histidine tag In a specific embodiment, the cleavable histidine tag may comprise or consist of the amino acid sequence GSTENLYFQSGALEHHHHHH (SEQ ID NO: 139). In another embodiment, the cleavable histidine tag may comprise the amino acid sequence $X_N$PQ(L/Q)PX$_N$HHHHHH (SEQ ID NO: 131), wherein $X_N$ is an linker of between 1-25 amino acid residue. In a further embodiment, the cleavable histidine tag may comprise the amino acid sequence GSSGSSGSQPQLPYGSSGSSGSHHHHHH (SEQ ID NO: 132).

In another aspect, the invention provides nucleic acids encoding the polypeptide of any embodiment of the invention. The invention further provides nucleic acid expression vector comprising the nucleic acids of the invention. The invention further provides recombinant host cells comprising the nucleic acid expression vectors of the invention. The invention also provides pharmaceutical composition, comprising the polypeptide, nucleic acid, nucleic acid expression vector, and/or the recombinant host cell of any embodiment of the invention, and a pharmaceutically acceptable carrier.

In another aspect, the invention provides methods for treating celiac sprue or non-celiac gluten sensitivity (NCGS), comprising administering to an individual with celiac sprue or NCGS an amount effective to treat the celiac sprue or NCGS of a polypeptide or pharmaceutical composition of any embodiment of the invention. In one embodiment, the polypeptide or the pharmaceutical composition is administered orally.

BRIEF DESCRIPTION OF THE FIGURES

FIG. 8a: detection of full-length DQ2.5-glia-ω1; FIG. 8b: detection of the PFPQPQ (SEQ ID NO: 148) breakdown product. Samples were taken at the indicated timepoints, and the concentration of either full-length peptide, or breakdown product PFPQPQ (SEQ ID NO: 148), was measured. Activities are graphed as the ratio of the appropriate m/z signal to that of the internal standard.

DETAILED DESCRIPTION

Figure 1:
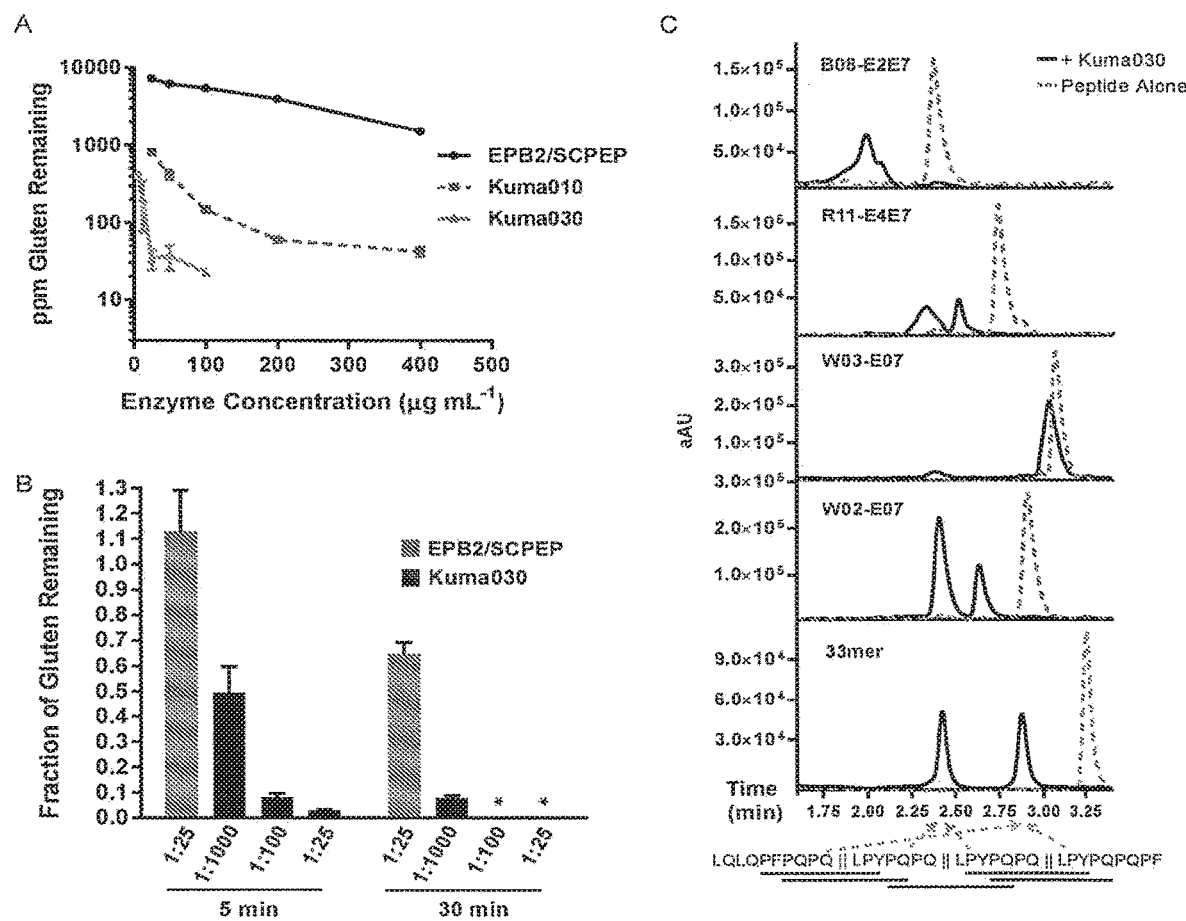
FIG. 1. Kuma030 is capable of rapidly and effectively degrading the immunogenic regions of gluten in gastric conditions. (A) The amount of gluten detected after a 60 minute incubation period with the indicated concentrations of either EPB2 and SCPEP (at a 1:1 ratio), Kuma010, or Kuma030 in gastric conditions, as measured by ELISA using the G12 antibody. The starting concentration of gluten was 10 mg mL-1 (10,000 ppm). Note that the Y-axis is plotted on a logarithmic scale. (B) The amount of gluten detected at 5 or 30 minutes after incubation with EPB2 and SCPEP at 400 µg mL-1, or Kuma030 at 10, 100, or 400 µg mL-1. The starting concentration of gluten was 10 mg mL-1. Samples were normalized to the amount of gluten measured after incubation with pepsin alone. ES: a 1:1 weight ratio of EPB2 and SCPEP. Asterisk indicates that the amount of gluten was below the level of quantification (5 ppm). (C) HPLC trace of full-length peptide (grey dotted lines) or breakdown products (black lines) of the immunodominant peptides from gliadin (W02-E07, W03-E07, 33mer), hordein (B08-E2E7), or secalin (R11-E4E7). The bottom of the figure shows the amino acid sequence of the 33mer peptide, position of known immunogenic epitopes (horizontal lines), location of the Kuma030 cleavage sites as determined by LCMS (vertical lines), and elution peaks of the resulting breakdown products (grey arrows). Immunodominant peptides displayed the following breakdown patterns: B08-E2E7: PQQPIPQ∥QPQPYPQ∥Q (SEQ ID NO: 61); R11-E4E5: QPFPQ∥QPEQIIPQ∥QP (SEQ ID NO:62); W02-E7: LQPFPQPQ∥LPYPQPQ (SEQ ID NO: 63); W03-E7: QPF-POPQ∥QPFPWQP (SEQ ID NO: 64). All peptide masses and elution times were confirmed by LCMS. Note that although the undigested W03-E07 peptide eluted at approximately the same time as the W03-E07 breakdown fragments, these are separate peaks, as determined by LCMS. aAU, arbitrary absorbance units.
Figure 2:
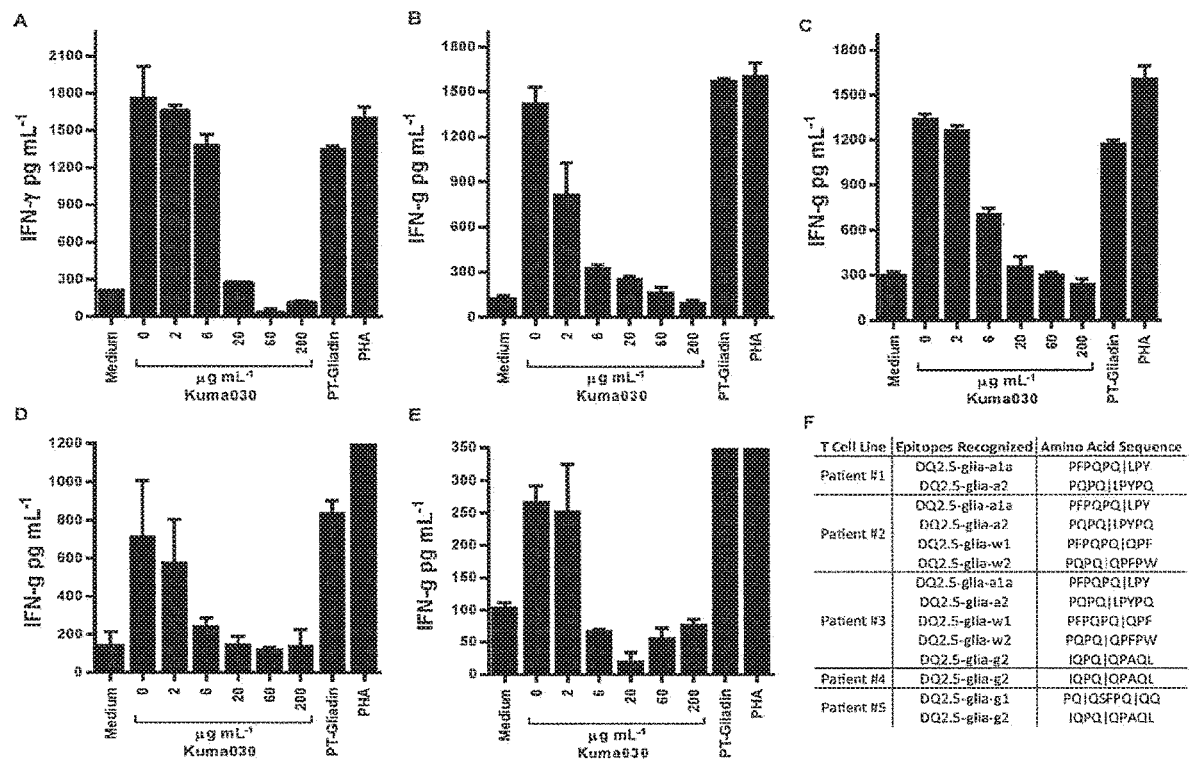
FIG. 2. Gliadin treated with Kuma030 loses it immunostimulatory potential. (A-E) Purified gliadin was treated with Kuma030 at the specified concentration for 60 minutes at pH 4.0 at 37° C. in the presence of 0.6 mg mL-1 pepsin. After the gastric phase, the pH of the samples was increased, and samples were treated with chymotrypsin and TG2. Samples were then exposed to T cell lines from patients #1 (A), #2 (B), #3 (C), #4 (D), or #5 (E), in the presence of autologous irradiated B cell lines, and IFN-γ was measured by ELISA. Phytohemagglutenin (PHA) and a peptic-tryptic digest of gliadin (PT-Gliadin) were included as positive controls. Incubation of T cell lines with antigen-presenting cells in the absence of antigens acted as a negative control. (F) T cell stimulatory epitopes recognized by the T cells used in this assay and the predicted Kuma030 cleavage sites within these epitopes. Predicted Kuma030 cleavage sites are shown by a vertical Cleavage sites are predicted based on Kuma030 activity on gliadin peptides as presented in FIG. 1F (from top to bottom: SEQ ID NOs: 141, 142, 141, 142, 143, 144, 141, 142, 143, 144, 145, 145, 146, 145).
Figure 3:
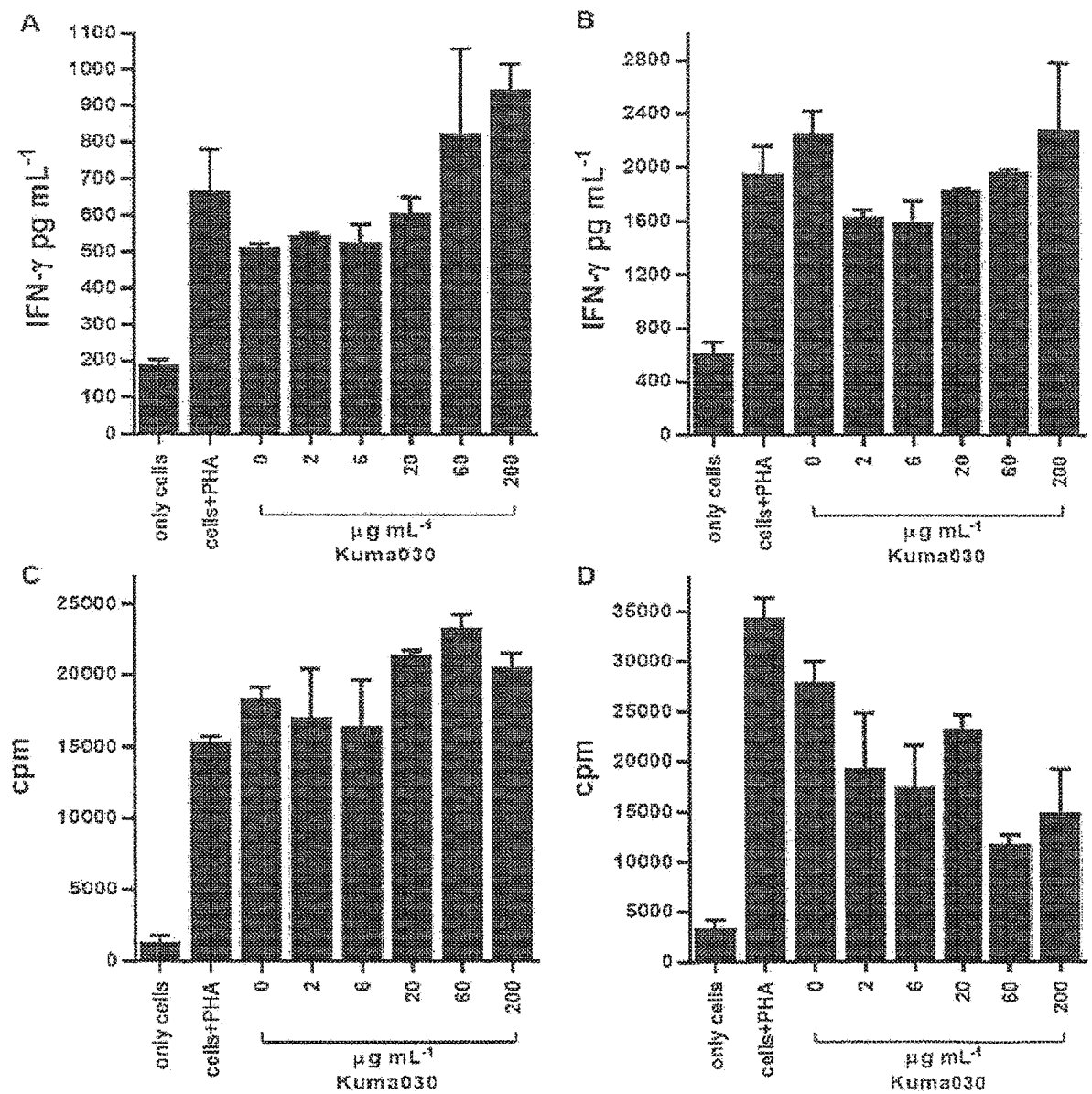
FIG. 3. Kuma030 is not toxic to T cells. Possible toxic effect of enzyme-treated gliadin was assessed in human peripheral blood mononuclear cells (PBMCs) from healthy donors that were stimulated with the mitogen phytohemagglutinin (PHA). (a,b) IFN-g production of T cells from healthy donor #1 (A) or healthy donor #2 (B). (C,D) T cell proliferation of T cells from healthy donor #1 (C) or healthy donor #2 (D). No effect on IFN-g production or cell proliferation was observed, except in the proliferation of healthy donor #2 (but not in the production of IFN-g). Since the reduction of PHA-stimulated cell proliferation was the same irrespective of the enzyme treatment, we conclude that this effect was not due to toxicity of the samples.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, 2nd Ed.* (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the invention can be used in combination, unless the context clearly dictates otherwise.

In a first aspect, the present invention provides polypeptides comprising an amino acid sequence at least 75% identical to the amino acid sequence of SEQ ID NO:1, wherein (a) residue 467 is Ser, residue 267 is Glu, and residue 271 is Asp; and (b) the polypeptide comprises an amino acid change from SEQ ID NO: 1 at one or more residues selected from the group consisting of 221, 262E, 268, 269, 270, 319A, 320, 354E/Q/R/Y, 358S/Q/T, 368F/Q, 399, 402, 406, 424, 449, 461, 463, 105, 171, 172, 173, 174, and 456. In one embodiment, the polypeptide comprises an amino acid change from SEQ ID NO: 1 at one or more residues selected from the group consisting of 221, 262E, 268, 269, 270, 319A, 320, 354E/Q/R/Y, 358S/Q/T, 368F/Q, 399, 402, 406, 424, 449, 461, and 463.

SEQ ID NO: 1 (Kuma 011)
Kuma011

(SEQ ID NO: 1)
MSDMEKPWKE(10)GEEARAVLQG(20)HARAQAPQAV(30)DKGPVAGD

ER(40)MAVTVVLRRQ(50)RAGELAAHVE(60)RQAAIAPHAR(70)EH

LKREAFAA(80)SHGASLDDFA(90)ELRRFADAHG(100)LALDRANVA

A(110)GTAVLSGPDD(120)AINRAFGVEL(130)RHFDHPDGSY

(140)RSYLGEVTVP(150)ASIAPMIEAV(160)LGLDTRPVAR(170)

PH(172)FRMQRRAE(180)GGFEARSQ(188)A

A(190)APTAYTPLDV(200)AQAYQFPEGL(210)DGQGQCIAII (220)E(221/32)LGGGYDEAS(230/41)LAQYFASLGV(240/51)

PAPQVVSVSV(250/61)DGASNQPTGD(260/71)PK(262/73)GPDG

E(267/78)V(268/79)E(269/80)L(270/81)D(271/82)IEVAG

ALAP(280/91)GAKFAVYFAP(290/101)DTTAGFLDAI(300/111)

TTAIHDPTLK(310/121)PSVVSISWS(319/130)G(320/131)PED

SWTSAAI(330/141)AAMNRAFLDA(340/151)AALGVTVLAA(350/

161)AGDS(354/165)GSTG(358/169)GE(360/171)QDGLYHVH (368/179)FP(370/181)AASPYVLACG(380/191)GTRLVASGGR (390/201)IAQETVWND(399/210)G(400/211)PD(402/213)GG

AT(406/217)GGGV(410/221)SRIFPLPAWQ(420/231)EHAN (424/235)VPPSAN(430/241)PGASSGRGVP(440/251)DLAGNAD

PA(449/260)T(450/261)GYEVVIDGEA(460/271)T(461/272)

VI(463/274)GGTS(467/278)AVAPLFAALVARINQKLGKAVGYLNP

TLYQLPADVFHDITEGNNDIANRAQIYQAGPGWDPCTGLGSPIGVRLLQA

LLPSASQPQP

Kuma010 as reference herein is identical to Kuma011, but includes the histidine tag sequence GSTENLYFQS-GALEHHHHHH (SEQ ID NO: 139) at its C-terminus.

Bold face residues represent the N-terminal portion present in the unprocessed polypeptide; non-bold faced font represents residues present in the processed version of the polypeptide. The numbers in parentheses indicate residue number; where there are two numbers separated by a "/", the number on the left is the residue number in the unprocessed version, and the number on the right is the residue number in the processed version. SEQ ID NO:1 is the unprocessed version of Kuma011; SEQ ID NO:71 is the processed version of Kuma011.

As disclosed in the examples that follow, polypeptides according to this aspect of the invention are improved polypeptides for use, for example, in treating celiac sprue. The polypeptides are modified versions of either the processed version or the preprocessed version of the polypeptide of SEQ ID NO: 1 (KUMAMAX™, hereinafter referred to as Kuma010), which was disclosed as useful for treating celiac sprue (WO2013/023151). Polypeptides for treating celiac sprue are capable of degrading proline (P)- and glutamine (Q)-rich components of gluten known as 'gliadins' believed responsible for the bulk of the immune response in most celiac sprue patients. The polypeptides of the present invention show superior activity in degrading peptides having a PQLP (SEQ ID NO: 65) or PQQP (SEQ ID NO: 66) motif (such as PFPQPQLPY (SEQ ID NO: 67) and/or PFPQPQQPF (SEQ ID NO: 68)), which are substrates representative of gliadin) at pH 4 compared to Kuma011 and other polypeptides disclosed as useful for treating celiac sprue (WO2015/023728), and/or are shown to improve production of the polypeptides. Thus, the polypeptides of the invention constitute significantly improved therapeutics for treating celiac sprue.

Thus, the polypeptides of the invention degrade a PFPQPQLPY (SEQ ID NO: 67) peptide and/or a PFPQPQQPF (SEQ ID NO: 68) peptide at pH 4, as well as LQLQPFPQPQLPYPQPQLPYPQPQLPYPQPQPF (SEQ ID NO: 69) and/or FLQPQQPFPQQPQQPYPQQPQQPFPQ (SEQ ID NO: 70).

Polypeptides of the first aspect of the invention comprise preprocessed versions of the polypeptide enzymes of the invention.

In a second aspect, the invention provides polypeptides comprising an amino acid sequence at least 75% identical to the amino acid sequence of SEQ ID NO:71, wherein (a) residue 278 is Ser, residue 78 is Glu, and residue 82 is Asp; and (b) the polypeptide comprises an amino acid change from SEQ ID NO: 71 at one or more residues selected from the group consisting of 32, 73E, 79, 80, 81, 130A, 131, 165E/Q/R/Y, 169S/Q/T, 179F/Q, 210, 213, 217, 235, 260, 267, 272, and 274. In one embodiment, the polypeptide comprises an amino acid change from SEQ ID NO: 71 at one or more residues selected from the group consisting of 32, 73E, 79, 80, 81, 130A, 131, 165E/Q/R/Y, 169S/Q/T, 179F/Q, 210, 213, 217, 235, 260, 272, and 274.

Polypeptides of the first aspect of the invention comprise processed versions of the polypeptide enzymes of the invention, and also degrade a PFPQPQLPY (SEQ ID NO: 67) peptide and/or a PFPQPQQPF (SEQ ID NO: 68) peptide at pH 4, as well as LQLQPFPQPQLPYPQPQLPYPQPQLPYPQPQPF (SEQ ID NO: 69) and/or FLQPQQPFPQQPQQPYPQQPQQPFPQ (SEQ ID NO: 70).

As used herein, "at least 75% identical" means that the polypeptide differs in its full length amino acid sequence by 25% or less (including any amino acid substitutions, deletions, additions, or insertions) from the polypeptide defined by SEQ ID NO: 1 or SEQ ID NO: 71.

In various embodiments of any aspect of the polypeptides of the invention, the polypeptides comprise or consist of an amino acid sequence at least 76%, 77%, 78%, 79%, 80%, 81%, 82%, 83%, 84%, 85%, 86%, 87%, 88%, 89%, 90%, 91%, 92%, 92%, 93%, 94%, 95%, 96%, 97%, 98%, or 99% identical to an amino acid sequence according to SEQ ID NO: 1 (preprocessed) or SEQ ID NO:71 (processed).

The polypeptide of any aspect of the polypeptides of the invention may comprises an amino acid change from SEQ ID NO: 1 or SEQ ID NO:71 at 2, 3, 4, 5, 6, 7, 8, 9, 10, 11, 12, 13, 14, 15, 16, 17, 18, 19, 20, 21, 22, 23, or all 24 (depending on the embodiment) of the recited residues.

In one embodiment of the polypeptides of the first aspect of the invention, the polypeptide comprises one or more amino acid changes from SEQ ID NO: 1 at one or more residues selected from the group consisting of 221D/N/Q/H, 262E, 268S/T/A, 269L/T, 270A/T/V, 319A, 354E/Q/R/Y, 358S/Q/T, 368F/Q, 399Q, 402S/Q, 406S, 424K, 449E/N/Q, 461R, and 463A/L/M/Q/R/T/V. As used throughout, the number indicates the residue number in the SEQ ID NO:1 or SEQ ID NO:71 polypeptide sequence, and the single letter amino acid abbreviations to the right of the number indicate the possible amino acid substitutions compared to the amino acid residue present at that position in SEQ ID NO:1 or 71.

In another embodiment of the polypeptides of the first aspect of the invention, the polypeptide comprises amino acid changes from SEQ ID NO: 1 at residues 399 and 449. In one embodiment, the polypeptide comprises amino acid changes 399Q and 449Q.

In a further embodiment of the polypeptides of the first aspect of the invention, the polypeptide comprises 358S and 463T. These polypeptide are extensively characterized in the examples that follow, as exemplified by the polypeptide designated as Kuma020 and variants thereof.

In one embodiment of the polypeptides of the first aspect of the invention, the polypeptide comprises 262E, 269T, 354Q, 358S, 399Q, 449Q, and 463T. These polypeptide are extensively characterized in the examples that follow, as exemplified by the polypeptide designated as Kuma030 and variants thereof. In another embodiment of the polypeptides of the first aspect of the invention, the polypeptide comprises 319A, 368F, 399Q, 449Q, and I463T. These polypeptide are extensively characterized in the examples that follow, as exemplified by the polypeptide designated as Kuma040 and variants thereof. In a further embodiment of the polypeptides of the first aspect of the invention, the polypeptide comprises 262E, 269T, 270V, 354Q, 358S, 399Q, and A449Q. These polypeptide are extensively characterized in the examples that follow, as exemplified by the polypeptide designated as Kuma050 and variants thereof. In one embodiment of the polypeptides of the first aspect of the invention, the polypeptide comprises 262E, 269T, 320M, 354Q, 358S, 399Q, 449Q, and 463T. These polypeptide are extensively characterized in the examples that follow, as exemplified by the polypeptide designated as Kuma060 and variants thereof. In a still further embodiment of the polypeptides of the first aspect of the invention, the polypeptide comprises, 319A, 320M, 368F, 399Q, 449Q, and 463T. These polypeptide are extensively characterized in the examples that follow, as exemplified by the polypeptide designated as Kuma070 and variants thereof.

In another embodiment of the polypeptides of the first aspect of the invention, the polypeptides comprise an amino acid change from SEQ ID NO: 1 at one or more amino acid positions selected from the group consisting of 105, 171, 172, 173, 174, and 456. In one embodiment, the amino acid change is 105H; 171R A, or S; 172R, A, or S; 173R or S, 174S, and/or 456V. In another embodiment, the amino acid change is 171R, 172R, and/or 456V.

In one embodiment of the polypeptides of the second aspect of the invention the polypeptide comprises one or more amino acid change from SEQ ID NO: 71 at one or more residues selected from the group consisting of 32D/N/Q/H, 73E, 79S/T/A, 80L/T, 81A/TN, 130A, 165E/Q/R/Y, 169S/Q/T, 179F/Q, 210Q, 213S/Q, 217Q, 235K, 260E/N/Q, 272R, and 274A/L/M/Q/R/T/V. In another embodiment of the polypeptides of the second aspect of the invention, the polypeptide comprises amino acid changes from SEQ ID NO: 71 at residues 210 and 260. In a further embodiment of the polypeptides of the second aspect of the invention, the polypeptide comprises amino acid changes 210Q and 260Q. In one embodiment of the polypeptides of the second aspect of the invention, the polypeptide comprises 169S and 274T. (Kuma 20 genus) In another embodiment of the polypeptides of the second aspect of the invention the polypeptide comprises 73E, 80T, 165Q, 169S, 210Q, 260Q, and 274T. (Kuma 30 genus) In a further embodiment of the polypeptides of the second aspect of the invention, the polypeptide comprises 130A, 179F, 210Q, 260Q, and 274T. (Kuma 40 genus) In a still further embodiment of the polypeptides of the second aspect of the invention, the polypeptide comprises 73E, 80T, 81V, 165Q, 169S, 210Q, and 260Q. (Kuma 50 genus) In one embodiment of the polypeptides of the second aspect of the invention, the polypeptide comprises 73E, 80T, 320M, 165Q, 169S, 210Q, and 274T. (Kuma 60 genus) In another embodiment of the polypeptides of the second aspect of the invention, the polypeptide comprises 130A, 131M, 179F, 210Q, 260Q, and 274T. (Kuma 70 genus) In a still further embodiment of the polypeptides of the second aspect of the invention, the polypeptides comprise an amino acid change from SEQ ID NO: 71 at one or more amino acid positions selected from the group consisting of 267. In one embodiment, the amino acid change is, 267V.

In a further embodiment of the polypeptides of any aspect of the invention, the polypeptides further comprise a histidine tag at the C-terminus of the polypeptide, to facilitate isolation of the polypeptide. Any suitable histidine tag can be used; in one embodiment the tag is linked to a TEV protease cut sit (ENLYFQS) (SEQ ID NO: 149) to allow for its efficient removal with TEV protease after purification, for example, the tag may comprise or consist of the amino acid sequence GSTENLYFQSGALEHHHHHH (SEQ ID NO: 139). In another embodiment, the histidine tag is a. cleavable histidine tag, permitting easier removal of the His-tag. In one embodiment, the cleavable histidine tag comprises the amino acid sequence $X_N$PQ(L/Q)PX$_N$HHHHHH (SEQ ID NO: 131), wherein $X_N$ is an linker of between 1-25 amino acid residues. In one non-limiting example, the cleavable histidine tag comprises the amino acid sequence GSSGSSGSQPQLPYGSSGSSGSHHHHHH (SEQ ID NO: 132).

In one embodiment of any aspect of the polypeptides of the invention, amino acid substitutions compared to SEQ ID NO: 1 or SEQ ID NO: 71 may comprise one or more of the substitutions noted in Tables 1 or 2. Substitutions at these positions were found to be generally well-tolerated (i.e. generally result in minor to no effects on activity), and in some cases to increase the activity of the polypeptides of the invention by no more than 20%.

TABLE 1

Possible Amino Acid Substitutions at Position Relative to Kuma10.

| Residue number (preprocessed/processed) | Residue |
|---|---|
| 221/32 | D, N, Q, H |
| 261/72 | A, R, N, D, C, Q, E, G, H, I, L, K, M, S, T, W, Y, V |
| 262/73 | A, R, N, D, C, Q, E, G, H, I, L, M, F, T, W, Y, V |
| 264/75 | A, N, D, C, Q, E, G, S, T, Y |
| 266/77 | A, C, S |

TABLE 1-continued

Possible Amino Acid Substitutions at Position Relative to Kuma10.

| Residue number (preprocessed/processed) | Residue |
|---|---|
| 268/79 | S, T |
| 269/80 | L, T |
| 270/81 | A, R, N, D, C, Q, E, G, I, K, S, T, V |
| 317/128 | A, N, C, G, T, V |
| 318/129 | A, R, N, D, C, Q, E, G, H, L, K, M, F, S, T, Y, V |
| 319/130 | A, N, D, C, Q, H, M, T |
| 320/131 | A, R, N, D, C, Q, K, M, S |
| 350/161 | N, D, C, G, S, T |
| 351/162 | G, S |
| 353/164 | A, R, N, C, Q, E, G, I, K, M, S, T, V |
| 354/165 | A, R, N, D, C, Q, E, G, H, L, K, M, F, T, W, Y |
| 358/169 | A, S, N, Q, T |
| 368/179 | A, R, N, C, Q, E, G, K, M, F, S, T, W, Y |
| 397/208 | A, C, F, Y |
| 399/210 | Q, N |
| 402/213 | Q, N, S |
| 406/217 | S |
| 424/235 | K |
| 446/257 | G, S |
| 448/259 | A, R, N, D, C, Q, E, G, H, I, L, K, M, F, S, T, W, Y, V |
| 449/260 | Q, E, G, N |
| 456/267 | A, N, D, C, Q, E, G, H, L, S, T, V |
| 461/272 | R |
| 463/274 | A, R, N, D, C, Q, E, G, H, L, K, M, F, S, T, W, Y, V |
| 464/277 | A, N, D, C, S, |
| 466/279 | D, C, G, S |

In another embodiment of any aspect of the polypeptides of the invention, amino acid substitutions compared to SEQ ID NO: 1 or SEQ ID NO: 71 may comprise one or more of the substitutions noted in Table 2.

| Residue number (preprocessed/processed) | Residue |
|---|---|
| 221/32 | D, N, Q, H |
| 261/72 | S |
| 262/73 | A, R, N, D, Q, E, G, L, M, T |
| 264/75 | A |
| 268/79 | S, T |
| 269/80 | L, T |
| 270/81 | A, T, V |
| 317/128 | A, T |
| 319/130 | A |
| 354/165 | A, R, N, D, Q, E, K, T, Y |
| 358/169 | A, S, N, Q, T |
| 368/179 | A, N, D, Q, E, S, T |
| 402/213 | Q, S |
| 406/217 | S |
| 424/235 | K |
| 446/257 | S |
| 449/260 | Q, N, A |
| 456/267 | V |
| 461/272 | R |
| 463/274 | A, R, Q, L, M, T, V |

In another embodiment of any aspect of the polypeptides of the invention, amino acid at each residue of the polypeptides of the invention may be as noted in Table 3, which lists all of the possible mutations at each position in the polypeptide enzymes as predicted by computational mutagenesis analysis. As described in the examples that follow, mutations were tested at each position found in the active site (residues 261-264, 266-267, 270, 317-320, 350-354, 368, 397, 403-404, 446, 448, 456, and 463-468) using degenerate primers to test the effects of various amino acid substitutions on activity; those that did not interfere with activity can be incorporated in the polypeptides of the invention, as reflected in Table 3.

TABLE 3

Possible Amino Acids at Residues Relative to Kuma 010

| Full Length | Mature | Amino Acid Possibilities |
|---|---|---|
| 190 | 1 | ALA, ARG, ASN, ASP, CYS, GLN, GLU, GLY, HIS, ILE, LEU, LYS, MET, PHE, PRO, SER, THR, TRP, TYR, VAL |
| 191 | 2 | ALA, ARG, ASN, ASP, CYS, GLN, GLU, GLY, HIS, ILE, LYS, MET, PHE, PRO, SER, THR, TRP, VAL |
| 192 | 3 | ALA, ARG, ASN, ASP, CYS, GLN, GLU, GLY, HIS, LEU, LYS, MET, PHE, PRO, SER, TRP, TYR |
| 193 | 4 | ALA, ARG, ASN, ASP, CYS, GLN, GLU, GLY, HIS, ILE, LEU, LYS, MET, PHE, PRO, SER, THR, TRP, TYR, VAL |
| 194 | 5 | ALA, ARG, ASN, ASP, CYS, GLN, GLU, GLY, HIS, LEU, LYS, MET, PHE, SER, THR, TRP, TYR, VAL |
| 195 | 6 | ALA, ASN, CYS, GLN, HIS, LEU, MET, PHE, THR, TYR |
| 196 | 7 | ALA, ARG, ASN, ASP, CYS, GLN, GLU, GLY, HIS, LYS, MET, PHE, SER, THR, TRP, TYR |
| 197 | 8 | ALA, GLY, PRO, SER |
| 198 | 9 | ALA, ARG, ASN, ASP, CYS, GLN, GLU, GLY, HIS, ILE, LEU, LYS, MET, PHE, SER, THR, TRP, TYR, VAL |
| 199 | 10 | ALA, ARG, ASN, ASP, CYS, GLN, GLU, GLY, HIS, LEU, LYS, MET, PHE, SER, THR, TRP, TYR |
| 200 | 11 | ALA, ASN, ASP, CYS, GLY, ILE, SER, THR, VAL |
| 201 | 12 | ALA, CYS, GLY, SER |
| 202 | 13 | ALA, ARG, ASN, ASP, CYS, GLN, GLU, GLY, HIS, ILE, LEU, LYS, MET, PHE, SER, THR, TRP, TYR, VAL |
| 203 | 14 | ALA, GLY, SER |
| 204 | 15 | ALA, ASN, ASP, CYS, GLN, GLU, GLY, HIS, ILE, LEU, LYS, MET, PHE, SER, THR, TYR |
| 205 | 16 | ALA, ARG, ASN, ASP, CYS, GLN, GLU, GLY, HIS, ILE, LEU, LYS, MET, PHE, SER, THR, TRP, TYR, VAL |
| 206 | 17 | ALA, ASN, ASP, CYS, GLN, GLU, GLY, HIS, ILE, LEU, LYS, MET, PHE, SER, THR, TYR, VAL |
| 207 | 18 | ALA, CYS, GLN, GLU, GLY, LYS, PRO, SER, THR, TRP |
| 208 | 19 | ALA, ARG, ASN, ASP, CYS, GLN, GLU, GLY, HIS, ILE, LEU, LYS, MET, PHE, PRO, SER, THR, TRP, TYR, VAL |
| 209 | 20 | ALA, ARG, ASN, ASP, CYS, GLN, GLU, GLY, HIS, ILE, LEU, LYS, MET, PHE, SER, THR, TRP, TYR, VAL |
| 210 | 21 | ALA, ARG, ASN, ASP, CYS, GLN, GLU, GLY, LEU, MET, SER, THR, VAL |
| 211 | 22 | ALA, ARG, ASN, ASP, CYS, GLN, GLU, GLY, HIS, LYS, MET, PHE, SER, THR, TYR |
| 212 | 23 | GLY |
| 213 | 24 | ALA, ARG, ASN, ASP, CYS, GLN, GLU, GLY, HIS, LEU, LYS, MET, PHE, SER, THR, TRP, TYR, VAL |
| 214 | 25 | GLY |
| 215 | 26 | ALA, ASN, ASP, CYS, GLN, GLU, GLY, SER, THR |
| 216 | 27 | ALA, ASN, ASP, CYS, GLN, GLY, SER, THR, VAL |
| 217 | 28 | ALA, CYS, ILE, LEU, SER, THR, VAL |
| 218 | 29 | ALA, GLY, SER |
| 219 | 30 | ALA, ASN, ASP, CYS, GLN, GLU, GLY, HIS, ILE, LEU, MET, SER, THR, VAL |
| 220 | 31 | ALA, ASN, ASP, CYS, GLN, GLU, GLY, ILE, SER, THR, VAL |
| 221 | 32 | ALA, ASN, ASP, CYS, GLN, GLU, GLY, ILE, SER, THR, VAL |
| 222 | 33 | ALA, ASN, ASP, CYS, GLN, GLU, GLY, ILE, LEU, LYS, SER, THR, VAL |
| 223 | 34 | ALA, ARG, ASN, ASP, CYS, GLU, GLY, LYS, MET, SER |
| 224 | 35 | GLY |
| 225 | 36 | GLY |
| 226 | 37 | ALA, ARG, ASN, ASP, CYS, GLU, GLY, HIS, LEU, PHE, SER, THR, TRP, TYR |
| 227 | 38 | ALA, ARG, ASN, ASP, CYS, GLN, GLU, GLY, LYS, MET, SER |
| 228 | 39 | ALA, ARG, ASN, ASP, CYS, GLN, GLU, GLY, HIS, ILE, LEU, LYS, MET, PHE, PRO, SER, THR, TRP, TYR, VAL |
| 229 | 40 | ALA, ARG, ASN, ASP, CYS, GLN, GLU, GLY, HIS, ILE, LEU, LYS, MET, PHE, SER, THR, TRP, TYR, VAL, |
| 230 | 41 | ALA, GLY, SER |
| 231 | 42 | ALA, ASN, ASP, CYS, GLN, GLU, GLY, LEU, SER, THR |
| 232 | 43 | ALA, ARG, ASN, ASP, CYS, GLN, GLU, GLY, HIS, ILE, LEU, LYS, MET, PHE, SER, THR, TRP, TYR, VAL, |
| 233 | 44 | ALA, ARG, ASN, ASP, CYS, GLN, GLU, GLY, HIS, ILE, LEU, LYS, MET, PHE, SER, THR, TRP, TYR, VAL, |
| 234 | 45 | ALA, ASN, CYS, GLY, HIS, PHE, SER, TYR |
| 235 | 46 | ALA, ASN, ASP, CYS, HIS, MET, PHE, SER, THR, TRP, TYR |
| 236 | 47 | ALA, ARG, ASN, ASP, CYS, GLN, GLU, GLY, HIS, ILE, LEU, LYS, MET, PHE, SER, THR, TRP, TYR, VAL, |
| 237 | 48 | ALA, ARG, ASN, ASP, CYS, GLN, GLU, GLY, HIS, ILE, LEU, LYS, MET, PHE, SER, THR, TRP, TYR, VAL, |
| 238 | 49 | ALA, ARG, ASN, ASP, CYS, GLN, GLU, GLY, HIS, ILE, LEU, MET, SER, THR, VAL |
| 239 | 50 | GLY |
| 240 | 51 | ALA, ARG, ASN, ASP, CYS, GLN, GLU, GLY, HIS, LEU, LYS, MET, SER, THR, TYR, VAL |
| 241 | 52 | ALA, ARG, ASN, ASP, CYS, GLN, GLU, GLY, HIS, ILE, LEU, LYS, MET, PHE, PRO, SER, THR, TRP, TYR, VAL |
| 242 | 53 | ALA, ARG, ASN, ASP, CYS, GLN, GLU, GLY, HIS, ILE, LYS, MET, PRO, SER, THR, VAL |
| 243 | 54 | ALA, GLY, PRO, SER |
| 244 | 55 | ALA, ARG, ASN, ASP, CYS, GLN, GLU, GLY, HIS, ILE, LEU, LYS, MET, PHE, PRO, SER, THR, TRP, TYR, VAL |
| 245 | 56 | ALA, ASN, CYS, GLY, SER, THR, VAL |
| 246 | 57 | ALA, ARG, ASN, ASP, CYS, GLN, GLU, GLY, HIS, ILE, LEU, LYS, MET, PHE, SER, THR, TRP, TYR, VAL |
| 247 | 58 | ALA, ARG, ASP, CYS, GLY, ILE, LYS, MET, PRO, SER |
| 248 | 59 | ALA, ARG, ASN, ASP, CYS, GLN, GLU, GLY, HIS, ILE, LYS, MET, PHE, SER, THR, TRP, TYR, VAL |
| 249 | 60 | ALA, ARG, ASN, ASP, CYS, GLN, GLU, GLY, ILE, LEU, LYS, MET, PRO, SER, THR |
| 250 | 61 | ALA, ASN, ASP, CYS, GLN, GLU, GLY, ILE, SER, THR, VAL |
| 251 | 62 | ALA, ARG, ASN, ASP, CYS, GLN, GLU, GLY, HIS, ILE, LEU, LYS, MET, PHE, SER, THR, TYR, VAL |
| 252 | 63 | ASN, ASP, GLY, SER |
| 253 | 64 | ALA, ARG, ASN, ASP, CYS, GLN, GLU, GLY, HIS, LYS, MET, PHE, SER, THR, TRP |
| 254 | 65 | ALA, ARG, ASN, ASP, CYS, GLN, GLU, GLY, HIS, ILE, LEU, LYS, MET, PHE, SER, THR, TRP, TYR, VAL |
| 255 | 66 | ALA, ARG, ASN, ASP, CYS, MET, SER, THR |
| 256 | 67 | ALA, ARG, ASN, ASP, CYS, GLN, GLU, GLY, HIS, ILE, LEU, LYS, MET, PHE, SER, THR, TRP, TYR, VAL |
| 257 | 68 | ALA, ARG, ASN, CYS, GLN, GLU, GLY, ILE, LYS, MET, PRO, SER, THR, VAL |
| 258 | 69 | ALA, ARG, ASN, ASP, CYS, GLN, GLU, GLY, HIS, ILE, LEU, LYS, MET, PHE, SER, THR, TRP, TYR, VAL |

TABLE 3-continued

| Possible Amino Acids at Residues Relative to Kuma 010 | | |
|---|---|---|
| Full Length | Mature | Amino Acid Possibilities |
| 259 | 70 | GLY |
| 260 | 71 | ALA, ARG, ASN, ASP, CYS, GLN, GLU, GLY, HIS, ILE, LEU, LYS, MET, PHE, SER, THR, TRP, TYR, VAL |
| 261 | 72 | ALA, ARG, ASN, ASP, CYS, GLN, GLU, GLY, HIS, ILE, LEU, LYS, MET, PRO, SER, THR, TRP, TYR, VAL |
| 262 | 73 | ALA, ARG, ASN, ASP, CYS, GLN, GLU, GLY, HIS, ILE, LEU, LYS, MET, PHE, SER, THR, TRP, TYR, VAL |
| 263 | 74 | GLY |
| 264 | 75 | ALA, ASN, ASP, CYS, GLN, GLU, GLY, PRO, SER, THR, TRP |
| 265 | 76 | ALA, ASN, ASP, CYS, GLN, GLU, GLY, SER, THR, VAL |
| 266 | 77 | ALA, CYS, GLY, SER |
| 267 | 78 | GLU |
| 268 | 79 | ALA, ASN, ASP, CYS, GLY, SER, THR, VAL |
| 269 | 80 | ALA, ARG, ASN, ASP, CYS, GLN, GLU, GLY, ILE, LEU, LYS, MET, SER, THR, VAL |
| 270 | 81 | ALA, ARG, ASN, ASP, CYS, GLN, GLU, GLY, ILE, LEU, LYS, SER, THR, VAL |
| 271 | 82 | ASP |
| 272 | 83 | ALA, ASN, ASP, CYS, GLN, GLU, GLY, ILE, MET, SER, THR, VAL |
| 273 | 84 | ALA, ASN, ASP, CYS, GLN, GLU, GLY, SER, THR |
| 274 | 85 | ALA, ASN, ASP, CYS, GLY, ILE, SER, THR, VAL |
| 275 | 86 | ALA, CYS, GLY, SER |
| 276 | 87 | GLY |
| 277 | 88 | ALA, GLY, SER |
| 278 | 89 | ALA, ASN, ASP, CYS, GLN, GLU, GLY, ILE, LEU, MET, SER, THR, VAL |
| 279 | 90 | ALA, GLY, SER |
| 280 | 91 | ALA, ASN, ASP, CYS, GLN, GLU, GLY, HIS, MET, PHE, PRO, SER, TRP, TYR |
| 281 | 92 | GLY |
| 282 | 93 | ALA, GLY, SER |
| 283 | 94 | ALA, ARG, ASN, ASP, CYS, GLN, GLU, GLY, HIS, ILE, LEU, LYS, MET, PHE, SER, THR, TRP, TYR, VAL |
| 284 | 95 | CYS, HIS, ILE, LEU, MET, PHE, THR, TYR, VAL |
| 285 | 96 | ALA, GLY, SER |
| 286 | 97 | ALA, ASN, ASP, CYS, GLY, SER, THR, VAL |
| 287 | 98 | ALA, ASN, ASP, CYS, GLN, HIS, LEU, PHE, SER, TYR |
| 288 | 99 | HIS, PHE |
| 289 | 100 | ALA, GLY, SER |
| 290 | 101 | ALA, ARG, ASN, ASP, CYS, GLN, GLU, GLY, HIS, ILE, LEU, LYS, MET, PHE, PRO, SER, THR, TRP, TYR, VAL |
| 291 | 102 | ALA, ARG, ASN, ASP, CYS, GLN, GLU, GLY, HIS, LEU, LYS, MET, PHE, PRO, SER, THR, TRP, TYR, VAL, |
| 292 | 103 | ALA, ARG, ASN, ASP, CYS, GLN, GLU, GLY, HIS, LEU, LYS, MET, PHE, SER, THR, TRP, TYR, VAL |
| 293 | 104 | ALA, ARG, ASN, ASP, CYS, GLN, GLU, GLY, HIS, ILE, LEU, LYS, MET, PRO, SER, THR, VAL |
| 294 | 105 | ALA, ARG, ASN, ASP, CYS, GLN, GLU, GLY, HIS, ILE, LEU, LYS, MET, PHE, PRO, SER, THR, TRP, TYR, VAL |
| 295 | 106 | GLY |
| 296 | 107 | ALA, ASN, ASP, CYS, GLN, GLU, GLY, HIS, LEU, LYS, MET, PHE, SER, THR, VAL |
| 297 | 108 | ALA, ARG, ASN, ASP, CYS, GLN, GLU, GLY, HIS, LEU, LYS, MET, PHE, SER, THR, TRP, TYR |
| 298 | 109 | ALA, ARG, ASN, ASP, CYS, GLN, GLU, GLY, HIS, ILE, LEU, LYS, MET, PHE, SER, THR, TRP, TYR, VAL, |
| 299 | 110 | ALA, GLY, SER |
| 300 | 111 | ALA, ASN, ASP, CYS, GLN, GLU, GLY, ILE, LEU, LYS, MET, SER, THR, VAL |
| 301 | 112 | ALA, ARG, ASN, ASP, CYS, GLN, GLU, GLY, ILE, LEU, LYS, MET, PHE, SER, THR, VAL |
| 302 | 113 | ALA, ARG, ASN, ASP, CYS, GLN, GLU, GLY, HIS, LYS, MET, SER, THR, TRP, VAL |
| 303 | 114 | ALA, GLY, SER |
| 304 | 115 | ALA, ASN, ASP, CYS, GLN, GLU, GLY, ILE, LEU, SER, THR, VAL |
| 305 | 116 | ALA, ARG, ASN, ASP, CYS, GLN, GLU, GLY, HIS, LEU, LYS, MET, PHE, SER, THR, TRP, TYR, VAL |
| 306 | 117 | ALA, ASN, ASP, SER |
| 307 | 118 | ALA, ARG, ASN, ASP, CYS, GLN, GLU, GLY, HIS, ILE, LEU, LYS, MET, PHE, PRO, SER, THR, TRP, TYR, VAL |
| 308 | 119 | ALA, ARG, ASN, ASP, CYS, GLN, GLU, GLY, HIS, ILE, LEU, LYS, MET, PHE, SER, THR, TRP, TYR, VAL, |
| 309 | 120 | ALA, ARG, ASN, ASP, CYS, GLN, GLU, GLY, HIS, LEU, LYS, MET, PHE, SER, THR, TRP, TYR |
| 310 | 121 | ALA, ARG, ASN, ASP, CYS, GLN, GLU, GLY, HIS, ILE, LEU, LYS, MET, PHE, SER, THR, TRP, TYR, VAL, |
| 311 | 122 | ALA, CYS, GLY, PRO, SER |
| 312 | 123 | ALA, ARG, ASN, ASP, CYS, GLN, GLU, GLY, HIS, LYS, MET, PHE, SER, THR, TRP, TYR |
| 313 | 124 | ALA, CYS, GLY, ILE, SER, THR, VAL |
| 314 | 125 | ALA, ASN, ASP, CYS, GLN, GLU, GLY, ILE, SER, THR, VAL |
| 315 | 126 | ALA, CYS, GLY, SER, THR |
| 316 | 127 | ALA, ASN, ASP, CYS, GLN, GLU, GLY, ILE, LEU, MET, SER, THR, VAL |
| 317 | 128 | ALA, ASN, CYS, GLY, SER, THR, VAL |
| 318 | 129 | ALA, ARG, ASN, ASP, CYS, GLN, GLU, GLY, HIS, LEU, LYS, MET, PHE, SER, THR, TRP, TYR, VAL |
| 319 | 130 | ALA, ASN, ASP, CYS, GLN, GLY, HIS, MET, SER, THR |
| 320 | 131 | ALA, ARG, ASN, ASP, CYS, GLN, GLY, LYS, MET, SER |
| 321 | 132 | ALA, CYS, GLY, PRO, SER |
| 322 | 133 | ALA, ASP, CYS, GLN, GLU, GLY, LEU, SER |
| 323 | 134 | ALA, ARG, ASN, ASP, CYS, GLN, GLU, GLY, HIS, ILE, LEU, LYS, MET, PHE, PRO, SER, THR, TRP, VAL, |
| 324 | 135 | ALA, ARG, ASN, ASP, CYS, GLN, GLU, GLY, HIS, ILE, LEU, LYS, MET, PHE, SER, THR, TRP, TYR, VAL, |
| 325 | 136 | ALA, ARG, ASN, ASP, CYS, GLN, GLU, GLY, HIS, LYS, MET, PHE, SER, TRP, TYR |
| 326 | 137 | ALA, ARG, ASN, ASP, CYS, GLN, GLU, GLY, HIS, LEU, LYS, MET, PHE, SER, THR, TRP, TYR |
| 327 | 138 | ALA, ARG, ASN, ASP, CYS, GLN, GLU, GLY, HIS, ILE, LEU, LYS, MET, PHE, PRO, SER, THR, TRP, TYR, VAL |
| 328 | 139 | ALA, ARG, ASN, ASP, CYS, GLN, GLU, GLY, HIS, ILE, LEU, LYS, MET, PHE, SER, THR, TRP, TYR, VAL, |
| 329 | 140 | ALA, ASP, CYS, GLY, SER |
| 330 | 141 | ALA, ARG, ASN, ASP, CYS, GLN, GLU, GLY, ILE, LEU, LYS, MET, SER, THR, VAL |
| 331 | 142 | ALA, ARG, ASN, ASP, CYS, GLN, GLU, GLY, HIS, ILE, LEU, LYS, MET, PHE, SER, THR, TRP, TYR, VAL, |
| 332 | 143 | ALA, ARG, ASN, ASP, CYS, GLN, GLU, GLY, HIS, ILE, LEU, LYS, MET, PHE, SER, THR, TRP, TYR, VAL, |
| 333 | 144 | ALA, ASN, ASP, CYS, GLN, GLU, GLY, HIS, ILE, LEU, LYS, MET, SER, THR, VAL |

TABLE 3-continued

Possible Amino Acids at Residues Relative to Kuma 010

| Full Length | Mature | Amino Acid Possibilities |
|---|---|---|
| 334 | 145 | ALA, ARG, ASN, ASP, CYS, GLU, GLY, MET, SER, THR, VAL |
| 335 | 146 | ALA, ARG, ASN, ASP, CYS, GLN, GLU, GLY, HIS, ILE, LEU, LYS, MET, PHE, SER, THR, TRP, TYR, VAL, |
| 336 | 147 | ALA, ARG, CYS, GLN, GLU, GLY, MET, SER |
| 337 | 148 | ALA, ARG, ASN, ASP, CYS, GLN, GLU, GLY, HIS, LEU, LYS, MET, PHE, SER, THR, TRP, TYR, VAL |
| 338 | 149 | ALA, ARG, ASN, ASP, CYS, GLN, GLU, GLY, HIS, ILE, LEU, LYS, MET, PHE, SER, THR, TRP, TYR, VAL, |
| 339 | 150 | ALA, ARG, ASN, ASP, CYS, GLN, GLU, GLY, HIS, ILE, LEU, LYS, MET, PHE, SER, THR, TRP, TYR, VAL, |
| 340 | 151 | ALA, ASN, ASP, GLY, SER |
| 341 | 152 | ALA, ARG, ASN, ASP, CYS, GLN, GLU, GLY, HIS, ILE, LYS, MET, SER, THR, VAL |
| 342 | 153 | ALA, ARG, ASN, ASP, CYS, GLN, GLU, GLY, HIS, ILE, LEU, LYS, MET, PHE, SER, THR, TRP, TYR, VAL, |
| 343 | 154 | ALA, ARG, ASN, ASP, CYS, GLN, GLU, GLY, HIS, ILE, LEU, LYS, MET, PHE, SER, THR, TRP, TYR, VAL, |
| 344 | 155 | ALA, ARG, ASN, ASP, CYS, GLN, GLU, GLY, HIS, LEU, LYS, MET, PHE, SER, THR, TRP, TYR |
| 345 | 156 | ALA, ARG, ASN, ASP, CYS, GLN, GLU, GLY, HIS, ILE, LEU, LYS, MET, PHE, SER, THR, TYR, VAL |
| 346 | 157 | ALA, ASN, ASP, CYS, GLN, GLU, GLY, HIS, LYS, MET, PHE, SER, THR |
| 347 | 158 | ALA, ASN, ASP, CYS, GLN, GLU, GLY, ILE, LYS, MET, PRO, SER, THR, VAL |
| 348 | 159 | ALA, ASN, ASP, CYS, GLN, GLU, GLY, LEU, SER, THR, VAL |
| 349 | 160 | ALA, CYS, GLY, SER, THR |
| 350 | 161 | ALA, ASN, ASP, CYS, GLY, SER, THR |
| 351 | 162 | ALA, GLY, SER |
| 352 | 163 | GLY |
| 353 | 164 | ALA, ARG, ASN, ASP, CYS, GLN, GLU, GLY, ILE, LYS, MET, SER, THR, VAL |
| 354 | 165 | ALA, ARG, ASN, ASP, CYS, GLN, GLU, GLY, HIS, LEU, LYS, MET, PHE, SER, THR, TRP, TYR |
| 355 | 166 | GLY |
| 356 | 167 | ALA, GLY, SER |
| 357 | 168 | ALA, ARG, ASN, ASP, CYS, GLN, GLU, GLY, ILE, MET, SER, THR, VAL |
| 358 | 169 | ALA, GLY, SER |
| 359 | 170 | ASN, GLY |
| 360 | 171 | ALA, ARG, ASN, ASP, CYS, GLN, GLU, GLY, ILE, LEU, LYS, MET, SER, THR, VAL |
| 361 | 172 | ALA, ARG, ASN, ASP, CYS, GLN, GLU, GLY, HIS, ILE, LEU, LYS, MET, PHE, SER, THR, TRP, TYR, VAL, |
| 362 | 173 | ALA, ARG, ASN, ASP, CYS, GLN, GLU, GLY, HIS, ILE, LEU, LYS, MET, PHE, SER, THR, TRP, TYR, VAL, |
| 363 | 174 | ASN, ASP, GLY, SER |
| 364 | 175 | ALA, ARG, ASN, ASP, CYS, GLN, GLU, GLY, HIS, LEU, LYS, MET, PHE, SER, THR, TRP, TYR |
| 365 | 176 | ALA, ARG, ASN, ASP, CYS, GLY, HIS, MET, PHE, SER, THR, TRP, TYR |
| 366 | 177 | ALA, ASN, ASP, CYS, HIS, LYS, SER |
| 367 | 178 | ALA, ASP, CYS, GLY, SER, THR, VAL |
| 368 | 179 | ALA, ARG, ASN, ASP, CYS, GLN, GLU, GLY, HIS, LYS, MET, PHE, SER, THR, TRP, TYR |
| 369 | 180 | ALA, CYS, HIS, PHE, SER, TYR |
| 370 | 181 | ALA, ASP, CYS, GLY, PRO, SER |
| 371 | 182 | ALA, GLY, SER |
| 372 | 183 | ALA, CYS, GLY, SER |
| 373 | 184 | ALA, GLY, SER |
| 374 | 185 | ALA, ARG, ASN, ASP, CYS, GLN, GLU, GLY, HIS, ILE, LEU, LYS, MET, PRO, SER, THR, TRP, VAL |
| 375 | 186 | ALA, ARG, ASN, ASP, CYS, GLN, GLU, GLY, HIS, LEU, LYS, MET, PHE, SER, THR, TRP, TYR, VAL |
| 376 | 187 | ALA, ASN, ASP, CYS, GLY, HIS, ILE, LEU, SER, THR, VAL |
| 377 | 188 | ALA, ARG, ASN, ASP, CYS, GLN, GLU, GLY, HIS, ILE, LEU, LYS, MET, SER, THR, VAL |
| 378 | 189 | ALA, GLY, SER |
| 379 | 190 | ALA, ASP, CYS, GLY, SER, THR |
| 380 | 191 | GLY |
| 381 | 192 | GLY |
| 382 | 193 | ALA, CYS, GLY, SER, THR |
| 383 | 194 | ALA, ARG, ASN, ASP, CYS, GLN, GLU, GLY, ILE, LEU, LYS, MET, SER, THR, VAL |
| 384 | 195 | ALA, ASN, ASP, CYS, GLN, GLU, GLY, LEU, SER, THR |
| 385 | 196 | ALA, ARG, ASN, ASP, CYS, GLN, GLU, GLY, HIS, ILE, LEU, LYS, MET, SER, THR, TRP, VAL |
| 386 | 197 | ALA, CYS, GLY, MET, SER, THR |
| 387 | 198 | ALA, ARG, ASN, ASP, CYS, GLN, GLU, GLY, HIS, ILE, LEU, LYS, MET, PHE, SER, THR, TRP, TYR, VAL, |
| 388 | 199 | ASN, ASP, GLY, LYS, SER |
| 389 | 200 | GLY |
| 390 | 201 | ALA, ARG, ASN, ASP, CYS, GLN, GLU, GLY, HIS, ILE, LEU, LYS, MET, PHE, SER, THR, TRP, TYR, VAL, |
| 391 | 202 | ALA, ASN, ASP, CYS, GLN, GLY, ILE, MET, PRO, SER, THR, VAL |
| 392 | 203 | ALA, ARG, ASN, ASP, CYS, GLN, GLU, GLY, HIS, LEU, LYS, MET, PHE, SER, THR, TRP, TYR |
| 393 | 204 | ALA, ARG, ASN, ASP, CYS, GLN, GLU, GLY, HIS, LEU, LYS, MET, PHE, SER, THR, TRP, TYR |
| 394 | 205 | ALA, CYS, GLN, GLU, GLY, SER, THR |
| 395 | 206 | ALA, ARG, ASN, ASP, CYS, GLN, GLU, GLY, ILE, LYS, MET, SER, THR, VAL |
| 396 | 207 | ALA, CYS, GLY, SER, THR, VAL |
| 397 | 208 | ALA, CYS, PHE, TRP, TYR |
| 398 | 209 | ARG, ASN, ASP, CYS, GLN, MET, SER |
| 399 | 210 | ALA, ARG, ASN, ASP, CYS, GLN, GLU, GLY, LEU, LYS, MET, SER |
| 400 | 211 | GLY |
| 401 | 212 | ALA, ARG, ASN, ASP, CYS, GLN, GLU, GLY, HIS, ILE, LEU, LYS, MET, PHE, PRO, SER, THR, TRP, TYR, VAL |
| 402 | 213 | ALA, ARG, ASN, ASP, CYS, GLN, GLU, GLY, HIS, ILE, LEU, LYS, MET, PHE, SER, THR, TRP, TYR, VAL, |
| 403 | 214 | GLY |
| 404 | 215 | GLY |
| 405 | 216 | ALA, GLY, SER |
| 406 | 217 | ALA, CYS, GLY, SER, THR |
| 407 | 218 | GLY |
| 408 | 219 | GLY |

TABLE 3-continued

| Possible Amino Acids at Residues Relative to Kuma 010 | | |
|---|---|---|
| Full Length | Mature | Amino Acid Possibilities |
| 409 | 220 | GLY |
| 410 | 221 | ALA, ASN, CYS, GLY, ILE, SER, THR, VAL |
| 411 | 222 | ALA, GLY, SER |
| 412 | 223 | ALA, ARG, ASN, ASP, CYS, GLN, GLU, GLY, HIS, ILE, LEU, LYS, MET, SER, THR, VAL |
| 413 | 224 | ALA, ARG, ASN, ASP, CYS, GLN, GLU, GLY, ILE, LYS, MET, PHE, SER, THR, TYR, VAL |
| 414 | 225 | ALA, ASN, CYS, GLN, GLU, HIS, ILE, LEU, LYS, MET, PHE, SER, THR, TYR, VAL |
| 415 | 226 | ALA, ARG, ASN, ASP, CYS, GLN, GLU, GLY, HIS, ILE, LEU, LYS, MET, PHE, PRO, SER, THR, TRP, TYR, VAL |
| 416 | 227 | ALA, ARG, ASN, ASP, CYS, GLN, GLU, GLY, ILE, LEU, LYS, MET, PRO, SER, THR, VAL |
| 417 | 228 | ALA, CYS, GLN, GLU, GLY, MET, PRO, SER, THR |
| 418 | 229 | ALA, ARG, ASN, ASP, CYS, GLN, GLU, GLY, HIS, ILE, LEU, LYS, MET, PHE, PRO, SER, THR, TRP, TYR, VAL |
| 419 | 230 | ALA, ASN, ASP, CYS, GLN, GLU, GLY, HIS, LEU, PHE, SER, TRP, TYR |
| 420 | 231 | GLN, GLU |
| 421 | 232 | ALA, ARG, ASN, ASP, CYS, GLN, GLU, GLY, HIS, ILE, LEU, LYS, MET, PHE, SER, THR, TRP, TYR, VAL, |
| 422 | 233 | ALA, ARG, ASN, ASP, CYS, GLN, GLU, GLY, HIS, ILE, LEU, LYS, MET, PHE, PRO, SER, THR, TRP, TYR, VAL |
| 423 | 234 | ALA, GLY, SER |
| 424 | 235 | ALA, ARG, ASN, ASP, CYS, GLN, GLU, GLY, HIS, ILE, LEU, LYS, MET, PHE, SER, THR, TRP, TYR, VAL, |
| 425 | 236 | ALA, CYS, GLY, PRO, SER, THR, VAL |
| 426 | 237 | ALA, ARG, ASN, ASP, CYS, GLN, GLU, GLY, HIS, ILE, LEU, LYS, MET, PHE, PRO, SER, THR, TRP, TYR, VAL |
| 427 | 238 | ALA, ARG, ASN, ASP, CYS, GLN, GLU, GLY, HIS, LYS, MET, PHE, PRO, SER, THR, TRP, TYR, VAL |
| 428 | 239 | ALA, ASN, ASP, CYS, GLN, GLU, GLY, SER, THR, VAL |
| 429 | 240 | ALA, ASN, ASP, CYS, GLY, SER |
| 430 | 241 | ALA, ASN, ASP, CYS, GLY, SER, THR |
| 431 | 242 | ALA, ARG, ASN, ASP, CYS, GLN, GLU, GLY, HIS, ILE, LEU, LYS, MET, PHE, PRO, SER, THR, TRP, TYR, VAL |
| 432 | 243 | ALA, ARG, ASN, ASP, CYS, GLN, GLU, GLY, HIS, ILE, LEU, LYS, MET, PHE, PRO, SER, THR, TRP, TYR, VAL |
| 433 | 244 | ALA, ARG, ASN, ASP, CYS, GLN, GLU, GLY, HIS, ILE, LEU, LYS, MET, PHE, SER, THR, TRP, TYR, VAL, |
| 434 | 245 | ALA, ARG, ASN, ASP, CYS, GLN, GLU, GLY, HIS, ILE, LEU, LYS, MET, PHE, PRO, SER, THR, TRP, TYR, VAL |
| 435 | 246 | ALA, ARG, ASN, ASP, CYS, GLN, GLU, GLY, HIS, ILE, LEU, LYS, MET, PHE, PRO, SER, THR, TRP, TYR, VAL |
| 436 | 247 | GLY |
| 437 | 248 | ALA, ARG, ASN, CYS, GLN, SER, THR |
| 438 | 249 | GLY |
| 439 | 250 | ALA, ASN, ASP, CYS, GLN, GLU, GLY, ILE, MET, SER, THR, VAL |
| 440 | 251 | ALA, GLY, PRO, SER |
| 441 | 252 | ASP |
| 442 | 253 | ALA, ASN, ASP, CYS, GLN, GLU, GLY, LEU, MET, SER, THR |
| 443 | 254 | ALA, GLY, SER |
| 444 | 255 | ALA, GLY |
| 445 | 256 | ALA, ASN, ASP, CYS, GLY, SER |
| 446 | 257 | ALA, GLY, SER |
| 447 | 258 | ALA, ASN, ASP, CYS, GLY, SER, THR |
| 448 | 259 | ALA, ARG, ASN, ASP, CYS, GLN, GLU, GLY, HIS, ILE, LEU, LYS, MET, PHE, PRO, SER, THR, TRP, TYR, VAL |
| 449 | 260 | ALA, ARG, ASN, ASP, CYS, GLN, GLU, GLY, HIS, ILE, LEU, LYS, MET, PHE, SER, THR, TRP, TYR, VAL, |
| 450 | 261 | ALA, ASN, ASP, CYS, GLY, HIS, SER, THR |
| 451 | 262 | GLY |
| 452 | 263 | ALA, ASN, CYS, GLN, HIS, ILE, LEU, PHE, SER, THR, TYR, VAL |
| 453 | 264 | ALA, ARG, ASN, ASP, CYS, GLN, GLU, GLY, HIS, ILE, LEU, LYS, MET, PHE, SER, THR, TRP, TYR, VAL, |
| 454 | 265 | ALA, ASN, ASP, CYS, GLY, SER, THR, VAL |
| 455 | 266 | ALA, ARG, ASN, ASP, CYS, GLU, GLY, HIS, ILE, MET, PHE, SER, THR, TRP, TYR, VAL |
| 456 | 267 | ALA, ASN, ASP, CYS, GLN, GLU, GLY, HIS, ILE, LEU, SER, THR, VAL |
| 457 | 268 | ALA, ASN, ASP, CYS, GLY, ILE, MET, SER, THR, TRP, VAL |
| 458 | 269 | ALA, ARG, ASN, ASP, CYS, GLN, GLU, GLY, LYS, MET, SER |
| 459 | 270 | ALA, ARG, ASN, ASP, CYS, GLN, GLU, GLY, HIS, ILE, LEU, LYS, MET, PHE, SER, THR, TRP, TYR, VAL, |
| 460 | 271 | ALA, ARG, ASN, ASP, CYS, GLN, GLU, GLY, HIS, ILE, LEU, LYS, MET, PHE, PRO, SER, THR, TYR, VAL, |
| 461 | 272 | ALA, ASN, ASP, CYS, GLN, GLY, HIS, LYS, MET, SER, THR |
| 462 | 273 | ALA, ARG, ASN, ASP, CYS, GLN, GLY, HIS, ILE, LYS, MET, PHE, SER, THR, TRP, TYR, VAL |
| 463 | 274 | ALA, ARG, ASN, ASP, CYS, GLN, GLU, GLY, HIS, ILE, LEU, LYS, MET, PHE, SER, THR, TRP, TYR, VAL, |
| 464 | 275 | GLY |
| 465 | 276 | GLY |
| 466 | 277 | ALA, ASN, ASP, CYS, GLY, SER, THR |
| 467 | 278 | SER |
| 468 | 279 | ALA, ASP, CYS, GLY, SER |
| 469 | 280 | ALA, ASN, ASP, CYS, GLY, SER, THR, VAL |
| 470 | 281 | ALA, GLY, SER |
| 471 | 282 | ALA, CYS, GLY, PRO, SER |
| 472 | 283 | ALA, ASN, ASP, CYS, GLN, GLU, GLY, HIS, LEU, MET, SER, THR, VAL |
| 473 | 284 | ALA, ASN, ASP, CYS, GLN, GLU, GLY, HIS, ILE, LEU, LYS, MET, PHE, SER, THR, TRP, TYR, VAL |
| 474 | 285 | ALA, GLY, SER |
| 475 | 286 | ALA, GLY, SER |
| 476 | 287 | ALA, ARG, ASN, ASP, CYS, GLN, GLU, GLY, HIS, LEU, LYS, MET, SER, THR, VAL |
| 477 | 288 | ALA, ASN, ASP, CYS, GLN, GLU, GLY, HIS, ILE, LYS, MET, SER, THR, VAL |
| 478 | 289 | ALA, GLY, SER |
| 479 | 290 | ALA, ARG, ASN, ASP, CYS, GLN, GLU, GLY, HIS, ILE, LEU, LYS, MET, SER, THR, TRP, TYR |
| 480 | 291 | ALA, ARG, ASN, ASP, CYS, GLU, GLY, ILE, LEU, LYS, MET, SER, THR, VAL |
| 481 | 292 | ALA, ASN, ASP, CYS, GLN, GLU, GLY, MET, SER |
| 482 | 293 | ALA, GLN, GLU, HIS, LYS, THR |
| 483 | 294 | ALA, ARG, ASN, ASP, CYS, GLN, GLU, GLY, HIS, LYS, MET, PHE, SER, TRP, TYR |

TABLE 3-continued

Possible Amino Acids at Residues Relative to Kuma 010

| Full Length | Mature | Amino Acid Possibilities |
|---|---|---|
| 484 | 295 | ALA, ARG, ASN, ASP, CYS, GLN, GLU, GLY, ILE, LEU, LYS, MET, SER, THR, VAL |
| 485 | 296 | ALA, ARG, ASN, ASP, CYS, GLN, GLU, GLY, HIS, ILE, LEU, LYS, MET, PHE, SER, TRP, TYR, VAL |
| 486 | 297 | ALA, ARG, ASN, ASP, CYS, GLN, GLU, GLY, HIS, ILE, LEU, LYS, MET, PHE, SER, THR, TRP, TYR, VAL |
| 487 | 298 | ALA, ARG, ASN, ASP, CYS, GLN, GLU, GLY, HIS, LEU, LYS, MET, PRO, SER, THR, TRP, VAL |
| 488 | 299 | ALA, ARG, ASN, ASP, CYS, GLN, GLU, GLY, ILE, LEU, LYS, MET, SER, THR, VAL |
| 489 | 300 | GLY |
| 490 | 301 | ALA, ARG, ASN, ASP, CYS, GLN, GLU, GLY, HIS, LEU, LYS, MET, PHE, PRO, SER, THR, TRP, TYR, VAL |
| 491 | 302 | ALA, ARG, ASN, ASP, CYS, GLN, GLU, GLY, HIS, ILE, LEU, LYS, MET, PHE, PRO, SER, THR, VAL |
| 492 | 303 | ALA, ARG, ASN, ASP, CYS, GLN, GLU, GLY, HIS, ILE, LEU, LYS, MET, PRO, SER, THR, VAL |
| 493 | 304 | ALA, ARG, ASN, ASP, CYS, GLN, GLU, GLY, HIS, ILE, LYS, MET, PHE, PRO, SER, THR, TRP, TYR, VAL |
| 494 | 305 | ALA, ARG, ASN, ASP, CYS, GLN, GLU, GLY, HIS, ILE, LEU, LYS, MET, PHE, PRO, SER, THR, TRP, TYR, VAL |
| 495 | 306 | ALA, ASN, ASP, CYS, GLN, GLU, GLY, HIS, LEU, MET, SER, THR |
| 496 | 307 | ALA, HIS, PHE, SER, THR, TYR |
| 497 | 308 | ALA, ARG, ASN, ASP, CYS, GLN, GLU, GLY, HIS, ILE, LEU, LYS, MET, PHE, SER, THR, TRP, TYR |
| 498 | 309 | ALA, ARG, ASN, ASP, CYS, GLN, GLU, GLY, LEU, MET, SER, THR |
| 499 | 310 | ALA, ARG, ASN, ASP, CYS, GLN, GLU, GLY, HIS, LEU, LYS, MET, PHE, PRO, SER, THR, TRP, TYR |
| 500 | 311 | ALA, ARG, ASN, ASP, CYS, GLN, GLU, GLY, HIS, ILE, LEU, LYS, MET, PHE, PRO, SER, THR, TRP, TYR, VAL |
| 501 | 312 | ALA, ARG, ASN, ASP, CYS, GLN, GLU, GLY, HIS, ILE, LEU, LYS, MET, PHE, SER, THR, TRP, TYR, VAL |
| 502 | 313 | ALA, ASN, ASP, CYS, GLY, ILE, MET, SER, THR, VAL |
| 503 | 314 | ALA, ASN, ASP, CYS, HIS, LEU, MET, PHE, SER, THR, TYR, VAL |
| 504 | 315 | ALA, ARG, ASN, ASP, CYS, GLN, GLU, GLY, HIS, ILE, LEU, LYS, MET, PHE, SER, THR, TRP, TYR, VAL |
| 505 | 316 | ALA, ARG, ASN, ASP, CYS, GLN, GLU, GLY, HIS, ILE, LEU, LYS, MET, PRO, SER, THR, VAL |
| 506 | 317 | ALA, ASN, ASP, CYS, GLN, GLY, ILE, SER, THR, VAL |
| 507 | 318 | ALA, ARG, ASN, ASP, CYS, GLN, GLU, GLY, HIS, ILE, LYS, MET, PHE, SER, THR, TRP, TYR, VAL |
| 508 | 319 | ALA, ARG, ASN, ASP, CYS, GLN, GLU, GLY, HIS, ILE, LEU, LYS, MET, PHE, SER, THR, TRP, TYR, VAL |
| 509 | 320 | GLY |
| 510 | 321 | ALA, ARG, ASN, ASP, CYS, GLN, GLU, GLY, HIS, LYS, MET, SER, THR, TRP, TYR |
| 511 | 322 | ALA, ASN, ASP, CYS, GLY, SER |
| 512 | 323 | ALA, ASN, ASP, CYS |
| 513 | 324 | ALA, ASN, ASP, CYS, GLN, GLU, GLY, ILE, LYS, MET, SER, THR, VAL |
| 514 | 325 | ALA, ARG, ASN, ASP, CYS, GLN, GLU, GLY, HIS, ILE, LYS, MET, PHE, SER, THR, TRP, TYR, VAL |
| 515 | 326 | ALA, ARG, ASN, ASP, CYS, GLN, GLU, GLY, HIS, LYS, MET, SER |
| 516 | 327 | ALA, ARG, ASN, ASP, CYS, GLN, GLU, GLY, HIS, ILE, LEU, LYS, MET, PHE, PRO, SER, THR, TRP, TYR, VAL |
| 517 | 328 | ALA, ARG, ASN, ASP, CYS, GLN, GLU, GLY, HIS, ILE, LEU, LYS, MET, PHE, SER, THR, TRP, TYR, VAL |
| 518 | 329 | ALA, ARG, ASN, ASP, CYS, GLN, GLU, GLY, HIS, LEU, LYS, MET, PHE, SER, THR, TRP, TYR |
| 519 | 330 | ALA, ARG, ASN, ASP, CYS, GLN, GLU, GLY, HIS, ILE, LEU, LYS, MET, PHE, SER, THR, TRP, TYR, VAL |
| 520 | 331 | HIS, PHE, THR, TRP, TYR |
| 521 | 332 | ALA, ARG, ASN, ASP, CYS, GLN, GLU, GLY, HIS, ILE, LEU, LYS, MET, PHE, SER, THR, TYR, VAL |
| 522 | 333 | ALA, GLY, SER |
| 523 | 334 | CYS, GLY, HIS, LYS, MET, PHE, SER, TYR |
| 524 | 335 | ALA, ARG, ASN, ASP, CYS, GLN, GLU, GLY, HIS, ILE, LEU, LYS, MET, PHE, PRO, SER, THR, TRP, TYR, VAL |
| 525 | 336 | GLY |
| 526 | 337 | HIS, PHE, TRP |
| 527 | 338 | ALA, ASN, ASP, CYS, SER |
| 528 | 339 | ALA, GLY, PRO, SER |
| 529 | 340 | ALA, ASP, CYS, GLY, SER, THR |
| 530 | 341 | ALA, ASN, CYS, GLY, SER, THR, VAL |
| 531 | 342 | GLY |
| 532 | 343 | ALA, ARG, ASN, ASP, CYS, GLN, GLU, GLY, LEU, LYS, MET, SER |
| 533 | 344 | GLY |
| 534 | 345 | ALA, CYS, GLY, SER, THR |
| 535 | 346 | ALA, CYS, GLY, PRO, SER, THR |
| 536 | 347 | ALA, ARG, ASN, ASP, CYS, GLN, GLU, GLY, ILE, LEU, LYS, MET, PHE, SER, THR, TYR, VAL |
| 537 | 348 | GLY |
| 538 | 349 | ALA, ARG, ASN, ASP, CYS, GLN, GLU, GLY, HIS, ILE, LEU, LYS, MET, PHE, SER, THR, TRP, TYR, VAL |
| 539 | 350 | ALA, ARG, ASN, ASP, CYS, GLN, GLU, GLY, HIS, LEU, LYS, MET, PHE, SER, THR, TRP, TYR |
| 540 | 351 | ALA, ASN, ASP, CYS, GLN, GLU, GLY, LEU, LYS, SER, THR, VAL |
| 541 | 352 | ALA, ARG, ASN, ASP, CYS, GLN, GLU, GLY, LEU, LYS, MET, SER, THR |
| 542 | 353 | ALA, ARG, ASN, ASP, CYS, GLN, GLU, GLY, HIS, ILE, LEU, LYS, MET, PHE, SER, THR, TRP, TYR, VAL |
| 543 | 354 | ALA, ARG, CYS, GLN, GLU, GLY, MET, SER, THR |
| 544 | 355 | ALA, ASN, ASP, CYS, GLN, GLU, GLY, LEU, MET, SER, THR |
| 545 | 356 | ALA, ARG, ASN, ASP, CYS, GLN, GLU, GLY, HIS, ILE, LEU, LYS, MET, PHE, SER, THR, TRP |
| 546 | 357 | Any residue |
| 547 | 358 | Any residue |
| 548 | 359 | Any residue |
| 549 | 360 | Any residue |
| 550 | 361 | Any residue |
| 551 | 362 | Any residue |
| 552 | 363 | Any residue |
| 553 | 364 | Any residue |

In a further embodiment, the polypeptides of the invention comprise or consist of the amino acid sequence selected from the group consisting of SEQ ID NOs: 2-42, 44-60 and 72-112, and 114-130 and 150-155, shown below. These polypeptides have increased activity relative to Kuma010, as shown in the examples that follow, or provide for improved production of the polypeptides. In one embodiment, the polypeptides comprise or consist of the amino acid sequence selected from the group consisting of SEQ ID NOs: 2-42, 55-60 and 72-112, and 125-130 and 150-155; these polypeptides all show improved activity to Kuma010.

The N-terminal domain is in bold font, and changes relative to Kuma 011 are noted next to the polypeptide name. In all cases, the polypeptides described below may further comprise a histidine tag at the C-terminus. Any suitable histidine tag can be used; Any suitable histidine tag can be used; in one embodiment the tag is linked to a TEV protease cut sit (ENLYFQS) (SEQ ID NO: 149) to allow for its efficient removal with TEV protease after purification, for example, the tag may comprise or consist of the amino acid sequence GSTENLYFQSGALEHHHHHH (SEQ ID NO: 139). In another embodiment, a cleavable histidine tag may be incorporated at the C-terminus, comprising the amino acid sequence $X_N$PQ(L/Q)PX$_N$HHHHHH (SEQ ID NO: 131), wherein $X_N$ is an linker of between 1-25 amino acid residues. In one non-limiting example, the cleavable histidine tag may comprise the amino acid sequence GSSGSSGSQPQLPYGSSGSSGSHHHHHH (SEQ ID NO: 132).

```
Kuma011-K262E
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPEGPDGEVELDIEVAGALAPGAKFAVYFAPDTTAGFLDAITTAI

HDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 2 (unprocessed),

SEQ ID NO: 72 (processed))

Kuma011-V268A
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEAELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 3 (unprocessed),

SEQ ID NO: 73 (processed))

Kuma011-V268S
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGESELDIEVAGALAPGAKFAVYFAPDTTAGFLDAITTAI
```

HDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 4 (unprocessed),

SEQ ID NO: 74 (processed))

Kuma011-V268T
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGETELDIEVAGALAPGAKFAVYFAPDTTAGFLDAITTAI

HDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 5 (unprocessed),

SEQ ID NO: 75 (processed))

Kuma011-E269L
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVLLDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 6 (unprocessed),

SEQ ID NO: 76 (processed))

Kuma011-E269T
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVTLDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

-continued

FAALVARINQKLGKAVGYLNPTLYQLPADVFHDITEGNNDIANRAQIYQAGPGWDP

CTGLGSPIGVRLLQALLPSASQPQP (SEQ ID NO: 7 (unprocessed),

SEQ ID NO: 77 (processed))

Kuma011-L270A
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVEADIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 8 (unprocessed),

SEQ ID NO: 78 (processed))

Kuma011-L270T
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVETDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 9 (unprocessed),

SEQ ID NO: 79 (processed))

Kuma011-L270V
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVEVDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 10 (unprocessed),

SEQ ID NO: 80 (processed))

-continued

Kuma011-G319A
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWAGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 11 (unprocessed),

SEQ ID NO: 81 (processed))

Kuma011-S354A
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDAGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 12 (unprocessed),

SEQ ID NO: 82 (processed))

Kuma011-S354E
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDEGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 13 (unprocessed),

SEQ ID NO: 83 (processed))

Kuma011-S354Q
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDQGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 14 (unprocessed),

SEQ ID NO: 84 (processed))

Kuma011-S354R
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDRGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 15 (unprocessed),

SEQ ID NO: 85 (processed))

Kuma011-S354Y
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDYGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 16 (unprocessed),

SEQ ID NO: 86 (processed))

Kuma011-G358N
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

-continued

```
SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTNGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP      (SEQ ID NO: 17 (unprocessed),

SEQ ID NO: 87 (processed))
```

Kuma011-G358S

MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

```
AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTSGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP      (SEQ ID NO: 18 (unprocessed),

SEQ ID NO: 88 (processed))
```

Kuma011-G358Q

MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

```
AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTQGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP      (SEQ ID NO: 19 (unprocessed),

SEQ ID NO: 89 (processed))
```

Kuma011-G358T

MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

```
AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTTGE

QDGLYHVHFPAASPYVLACGGTRLVASGGRIAQETVWNDGPDGGATGGGVSRIFPL
```

-continued

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 20 (unprocessed),

SEQ ID NO: 90 (processed))

Kuma011-H368F
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVFFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 21 (unprocessed),

SEQ ID NO: 91 (processed))

Kuma011-H368Q
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVQFPAASPYVLACGGTRLVASGGRIAQETVWNDGPDGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 22 (unprocessed),

SEQ ID NO: 92 (processed))

Kuma011-D399Q
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNQGPDGGATGGGVSRIFPL

PAWQEHANVPPSANPGASSGRGVPDLAGNADPATGYEVVIDGEATVIGGTSAVAPL

-continued

FAALVARINQKLGKAVGYLNPTLYQLPADVFHDITEGNNDIANRAQIYQAGPGWDP

CTGLGSPIGVRLLQALLPSASQPQP (SEQ ID NO: 23 (unprocessed),

SEQ ID NO: 93 (processed))

Kuma011-D402S
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNQGPSGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 24 (unprocessed),

SEQ ID NO: 94 (processed))

Kuma011-D402Q
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNQGPQGGATGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 25 (unprocessed),

SEQ ID NO: 95 (processed))

Kuma011-T406S
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNQGPQGGASGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 26 (unprocessed),

SEQ ID NO: 96 (processed))

Kuma011-N424K

MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNQGPQGGASGGGVSRIFPL

PAWQEHANVPPSANPGASSGRGVPDLAGNADPATGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 27 (unprocessed),

SEQ ID NO: 97 (processed))

Kuma011-A449E

MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPETGYEVVIDGEATVIGGTSAVAPLF

AALVARINQKLGKAVGYLNPTLYQLPADVFHDITEGNNDIANRAQIYQAGPGWDPC

TGLGSPIGVRLLQALLPSASQPQP (SEQ ID NO: 28 (unprocessed),

SEQ ID NO: 98 (processed))

Kuma011-A449Q

MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPQTGYEVVIDGEATVIGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 29 (unprocessed),

SEQ ID NO: 99 (processed))

Kuma011-I456V

MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

-continued

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVVDGEATVTGGTSAVAP

LFAALVARINQKLGKAVGYLNPTLYQLPADVFHDITEGNNDIANRAQIYQAGPGWD

PCTGLGSPIGVRLLQALLPSASQPQP (SEQ ID NO: 30 (unprocessed),

SEQ ID NO: 100 (processed))

Kuma011-T461R

MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEARVTGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 31 (unprocessed),

SEQ ID NO: 101 (processed))

Kuma011-I463A

MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVAGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 32 (unprocessed),

SEQ ID NO: 102 (processed))

Kuma011-I463L

MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

```
AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVLGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 33 (unprocessed),

SEQ ID NO: 103 (processed))
```

Kuma011-I463M
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

```
AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVMGGTSAVAP

LFAALVARINQKLGKAVGYLNPTLYQLPADVFHDITEGNNDIANRAQIYQAGPGWD

PCTGLGSPIGVRLLQALLPSASQPQP (SEQ ID NO: 34 (unprocessed),

SEQ ID NO: 104 (processed))
```

Kuma011-I463Q
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

```
AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVQGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 35 (unprocessed),

SEQ ID NO: 105 (processed))
```

Kuma011-I463R
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

```
AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE
```

-continued

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVRGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 36 (unprocessed),

SEQ ID NO: 106 (processed))

Kuma011-I463T
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVTGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 37 (unprocessed),

SEQ ID NO: 107 (processed))

Kuma011-I463V
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTGGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVVGGTSAVAPL

FAALVARINQKLGKAVGYLNPTLYQLPADVFHDITEGNNDIANRAQIYQAGPGWDP

CTGLGSPIGVRLLQALLPSASQPQP (SEQ ID NO: 38 (unprocessed),

SEQ ID NO: 108 (processed))

Kuma023: G368S; I463T
MSDMEKPWKEGEEARAVLQGHARAQAPQAVDKGPVAGDERMAVTVVLRRQR

AGELAAHVERQAAIAPHAREHLKREAFAASHGASLDDFAELRRFADAHGLALD

RANVAAGTAVLSGPDDAINRAFGVELRHFDHPDGSYRSYLGEVTVPASIAPMIEA

VLGLDTRPVARPHFRMQRRAEGGFEARSQA

AAPTAYTPLDVAQAYQFPEGLDGQGQCIAIIELGGGYDEASLAQYFASLGVPAPQVV

SVSVDGASNQPTGDPKGPDGEVELDIEVAGALAPGAKFAVYFAPDTTAGFLDAITTA

IHDPTLKPSVVSISWSGPEDSWTSAAIAAMNRAFLDAAALGVTVLAAAGDSGSTSGE

QDGLYHVHFPAASPYVLACGGTRLVASGGRIAQETVWNDGPDGGATGGGVSRIFPL

PAWQEHANVPPSANPGASSGRGVPDLAGNADPATGYEVVIDGEATVTGGTSAVAPL

-continued
FAALVARINQKLGKAVGYLNPTLYQLPADVFHDITEGNNDIANRAQIYQAGPGWDP

CTGLGSPIGVRLLQALLPSASQPQP (SEQ ID NO: 39 (unprocessed),

SEQ ID NO: 109 (processed))

Kuma 020 as referenced in the examples is the Kuma023 polypeptide that includes the following C-terminal histidine tag: GSTENLYFQSGALEHHHHHH (SEQ ID NO: 139).

Kuma021: G368S; D399Q; A449Q; I463T
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARPHFRMQRRAEGGFEARSQA

AAPTAYTPLDVAQAYQFPEGLDGQGQCIAIIELGGGYDEASLAQYFASLG

VPAPQVVSVSVDGASNQPTGDPKGPDGEVELDIEVAGALAPGAKFAVYFA

PDTTAGFLDAITTAIHDPTLKPSVVSISWSGPEDSWTSAAIAAMNRAFLD

AAALGVTVLAAAGDSGSTSGEQDGLYHVFFPAASPYVLACGGTRLVASGG

RIAQETVWNQGPDGGATGGGVSRIFPLPAWQEHANVPPSANPGASSGRGV

PDLAGNADPQTGYEVVIDGEATVTGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 154 (unprocessed),

SEQ ID NO: 155 (processed))

Kuma031: K262E; E269T; S354Q; G358S; D399Q; A449Q; I463T
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARPHFRMQRRAEGGFEARSQA

AAPTAYTPLDVAQAYQFPEGLDGQGQCIAIIELGGGYDEASLAQYFASLG

VPAPQVVSVSVDGASNQPTGDPEGPDGEVTLDIEVAGALAPGAKFAVYFA

PDTTAGFLDAITTAIHDPTLKPSVVSISWSGPEDSWTSAAIAAMNRAFLD

AAALGVTVLAAAGDQGSTSGEQDGLYHVFPAASPYVLACGGTRLVASGG

RIAQETVWNQGPDGGATGGGVSRIFPLPAWQEHANVPPSANPGASSGRGV

PDLAGNADPQTGYEVVIDGEATVTGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 40 (unprocessed),

SEQ ID NO: 110 (processed))

Kuma 030 as referenced in the examples is the Kuma031 polypeptide that includes the following C-terminal histidine tag: GSTENLYFQSGALEHHHHHH (SEQ ID NO: 139).

Kuma041: S319A; H368F; D399Q; A449Q; I463T
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARPHFRMQRRAEGGFEARSQA

AAPTAYTPLDVAQAYQFPEGLDGQGQCIAIIELGGGYDEASLAQYFASLG

VPAPQVVSVSVDGASNQPTGDPKGPDGEVTLDIEVAGALAPGAKFAVYFA

PDTTAGFLDAITTAIHDPTLKPSVVSISWAGPEDSWTSAAIAAMNRAFLD

AAALGVTVLAAAGDSGSTGGEQDGLYHVFFPAASPYVLACGGTRLVASGG

RIAQETVWNQGPDGGATGGGVSRIFPLPAWQEHANVPPSANPGASSGRGV

PDLAGNADPQTGYEVVIDGEATVTGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 41 (unprocessed),

SEQ ID NO: 111 (processed))

Kuma 040 as referenced in the examples is the Kuma041 polypeptide that includes the following C-terminal histidine tag: GSTENLYFQSGALEHHHHHH (SEQ ID NO: 139).

Kuma051: K262E; E269T; L270V; S354Q; G358S; D399Q; A449Q
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARPHFRMQRRAEGGFEARSQA

AAPTAYTPLDVAQAYQFPEGLDGQGQCIAIIELGGGYDEASLAQYFASLG

VPAPQVVSVSVDGASNQPTGDPEGPDGEVTVDIEVAGALAPGAKFAVYFA

PDTTAGFLDAITTAIHDPTLKPSVVSISWSGPEDSWTSAAIAAMNRAFLD

AAALGVTVLAAAGDQGSTSGEQDGLYHVHFPAASPYVLACGGTRLVASGG

RIAQETVWNQGPDGGATGGGVSRIFPLPAWQEHANVPPSANPGASSGRGV

PDLAGNADPQTGYEVVIDGEATVIGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 42 (unprocessed),

SEQ ID NO: 112 (processed))

Kuma 050 as referenced in the examples is the Kuma051 polypeptide that includes the following C-terminal histidine tag: GSTENLYFQSGALEHHHHHH (SEQ ID NO: 139).

Kuma022: P171R; H172R; G368S; I463T
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARRRFRMQRRAEGGFEARSQA

-continued

AAPTAYTPLDVAQAYQFPEGLDGQGQCIAIIELGGGYDEASLAQYFASLG

VPAPQVVSVSVDGASNQPTGDPKGPDGEVELDIEVAGALAPGAKFAVYFA

PDTTAGFLDAITTAIHDPTLKPSVVSISWSGPEDSWTSAAIAAMNRAFLD

AAALGVTVLAAAGDSGSTSGEQDGLYHVHFPAASPYVLACGGTRLVASGG

RIAQETVWNDGPDGGATGGVSRIFPLPAWQEHANVPPSANPGASSGRGV

PDLAGNADPATGYEVVIDGEATVTGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 55 (unprocessed),

SEQ ID NO: 125 (processed))

Kuma032: P171R; H172R; K262E; E269T;
S354Q; G358S; D399Q; A449Q; I463T
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARRRFRMQRRAEGGFEARSQA

AAPTAYTPLDVAQAYQFPEGLDGQGQCIAIIELGGGYDEASLAQYFASLG

VPAPQVVSVSVDGASNQPTGDPEGPDGEVTLDIEVAGALAPGAKFAVYFA

PDTTAGFLDAITTAIHDPTLKPSVVSISWSGPEDSWTSAAIAAMNRAFLD

AAALGVTVLAAAGDQGSTSGEQDGLYHVHFPAASPYVLACGGTRLVASGG

RIAQETVWNQGPDGGATGGVSRIFPLPAWQEHANVPPSANPGASSGRGV

PDLAGNADPQTGYEVVIDGEATVTGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 56 (unprocessed),

SEQ ID NO: 126 (processed))

Kuma042: P171R; H172R; S319A; H368F;
D399Q; A449Q; I463T
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARRRFRMQRRAEGGFEARSQA

AAPTAYTPLDVAQAYQFPEGLDGQGQCIAIIELGGGYDEASLAQYFASLG

VPAPQVVSVSVDGASNQPTGDPKGPDGEVTLDIEVAGALAPGAKFAVYFA

PDTTAGFLDAITTAIHDPTLKPSVVSISWAGPEDSWTSAAIAAMNRAFLD

AAALGVTVLAAAGDSGSTGGEQDGLYHVFFPAASPYVLACGGTRLVASGG

RIAQETVWNQGPDGGATGGVSRIFPLPAWQEHANVPPSANPGASSGRGV

PDLAGNADPQTGYEVVIDGEATVTGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 57 (unprocessed),

SEQ ID NO: 127 (processed))

Kuma052: P171R; H172R; K262E; E269T;
L270V; S354Q; G358S; D399Q; A449Q
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARRRFRMQRRAEGGFEARSQA

AAPTAYTPLDVAQAYQFPEGLDGQGQCIAIIELGGGYDEASLAQYFASLG

VPAPQVVSVSVDGASNQPTGDPEGPDGEVTVDIEVAGALAPGAKFAVYFA

PDTTAGFLDAITTAIHDPTLKPSVVSISWSGPEDSWTSAAIAAMNRAFLD

AAALGVTVLAAAGDQGSTSGEQDGLYHVHFPAASPYVLACGGTRLVASGG

RIAQETVWNQGPDGGATGGVSRIFPLPAWQEHANVPPSANPGASSGRGV

PDLAGNADPQTGYEVVIDGEATVIGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 58 (unprocessed),

SEQ ID NO: 128 (processed))

Kuma061: K262E; E269T; S354Q; G358S;
D399Q; A449Q; I463T
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARPHFRMQRRAEGGFEARSQA

AAPTAYTPLDVAQAYQFPEGLDGQGQCIAIIELGGGYDEASLAQYFASLG

VPAPQVVSVSVDGASNQPTGDPEGPDGEVTLDIEVAGALAPGAKFAVYF

APDTTAGFLDAITTAIHDPTLKPSVVSISWSMPEDSWTSAAIAAMNRAF

LDAAALGVTVLAAAGDQGSTSGEQDGLYHVHFPAASPYVLACGGTRLVA

SGGRIAQETVWNQGPDGGATGGVSRIFPLPAWQEHANVPPSANPGASS

GRGVPDLAGNADPQTGYEVVIDGEATVTGGTSAVAPLFAALVARINQKL

GKAVGYLNPTLYQLPADVFHDITEGNNDIANRAQIYQAGPGWDPCTGLG

SPIGVRLLQALLPSASQPQP (SEQ ID NO: 150

(unprocessed), SEQ ID NO: 151 (processed))

Kuma 060 as referenced in the examples is the Kuma061 polypeptide that includes the following C-terminal histidine tag: GSTENLYFQSGALEHHHHHH (SEQ ID NO: 139).

Kuma062: P171R; H172R; K262E; E269T;
S354Q; G358S; D399Q; A449Q; I463T
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARRRFRMQRRAEGGFEARSQA

AAPTAYTPLDVAQAYQFPEGLDGQGQCIAIIELGGGYDEASLAQYFASLG

VPAPQVVSVSVDGASNQPTGDPEGPDGEVTLDIEVAGALAPGAKFAVYFA

PDTTAGFLDAITTAIHDPTLKPSVVSISWSMPEDSWTSAAIAAMNRAFLD

AAALGVTVLAAAGDQGSTSGEQDGLYHVHFPAASPYVLACGGTRLVASGG

RIAQETVWNQGPDGGATGGVSRIFPLPAWQEHANVPPSANPGASSGRGV

-continued
PDLAGNADPQTGYEVVIDGEATVTGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 59 (unprocessed),

SEQ ID NO: 129 (processed))

Kuma071: S319A; H368F; D399Q; A449Q;
I463T
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARPHFRMQRRAEGGFEARSQA

AAPTAYTPLDVAQAYQFPEGLDGQGQCIAIIELGGGYDEASLAQYFASLG

VPAPQVVSVSVDGASNQPTGDPKGPDGEVTLDIEVAGALAPGAKFAVYFA

PDTTAGFLDAITTAIHDPTLKPSVVSISWAMPEDSWTSAAIAAMNRAFLD

AAALGVTVLAAAGDSGSTGGEQDGLYHVFFPAASPYVLACGGTRLVASGG

RIAQETVWNQGPDGGATGGGVSRIFPLPAWQEHANVPPSANPGASSGRGV

PDLAGNADPQTGYEVVIDGEATVTGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 152 (unprocessed),

SEQ ID NO: 153 (processed))

Kuma 070 as referenced in the examples is the Kuma071 polypeptide that includes the following C-terminal histidine tag: GSTENLYFQSGALEHHHHHH (SEQ ID NO: 139).

Kuma072: P171R; H172R; S319A; H368F;
D399Q; A449Q; I463T
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARRRFRMQRRAEGGFEARSQA

AAPTAYTPLDVAQAYQFPEGLDGQGQCIAIIELGGGYDEASLAQYFASLG

VPAPQVVSVSVDGASNQPTGDPKGPDGEVTLDIEVAGALAPGAKFAVYFA

PDTTAGFLDAITTAIHDPTLKPSVVSISWAMPEDSWTSAAIAAMNRAFLD

AAALGVTVLAAAGDSGSTGGEQDGLYHVFFPAASPYVLACGGTRLVASGG

RIAQETVWNQGPDGGATGGGVSRIFPLPAWQEHANVPPSANPGASSGRGV

PDLAGNADPQTGYEVVIDGEATVTGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 60 (unprocessed),

SEQ ID NO: 130 (processed))

As described in Table 5, the changes made to Kuma010/011 have significant effect on the catalytic activity of the design proteins. Table 5 lists the effectiveness of individual mutations in catalyzing the degradation of various gliadin peptide sequences. The examples provide further data regarding specific individual and combination mutants.

TABLE 5

| Position (Full Length) | Position (Truncated) | Kuma010 A.A. | A.A. relative to Kuma010/011 | % Improvement on PFPQPQLPY (SEQ ID NO: 67) | % Improvement on PFPQPQQPF (SEQ ID NO: 68) |
| --- | --- | --- | --- | --- | --- |
| 221 | 32 | E | D, N, Q, H | 105% | ND |
| 262 | 73 | K | E | 109% | 110% |
| 268 | 79 | V | A | 107% | 89% |
| 268 | 79 | V | S | 104% | 83% |
| 268 | 79 | V | T | 127% | 105% |
| 269 | 80 | E | L | 113% | 84% |
| 269 | 80 | E | T | 263% | 191% |
| 270 | 81 | L | A | 203% | 92% |
| 270 | 81 | L | T | 307% | 29% |
| 270 | 81 | L | V | 474% | 61% |
| 319 | 130 | S | A | 154% | 184% |
| 354 | 165 | S | A | 152% | 140% |
| 354 | 165 | S | E | 124% | 120% |
| 354 | 165 | S | Q | 145% | 141% |
| 354 | 165 | S | R | 109% | 82% |
| 354 | 165 | S | Y | 46% | 105% |
| 358 | 169 | G | N | 120% | 99% |
| 358 | 169 | G | S | 331% | 224% |
| 358 | 169 | G | Q | 147% | 149% |
| 358 | 169 | G | T | 283% | 128% |
| 368 | 179 | H | F | 334% | 104% |
| 368 | 179 | H | Q | 199% | 195% |
| 399 | 210 | D | Q | 149% | 208% |
| 402 | 213 | D | S | 94% | 108% |
| 402 | 213 | D | Q | 164% | 111% |
| 406 | 217 | T | S | 84% | 101% |
| 424 | 235 | N | K | 285% | ND |
| 449 | 260 | A | E | 149% | 208% |
| 449 | 260 | A | N | 119% | 118% |
| 461 | 272 | T | R | 120% | 86% |

TABLE 5-continued

| Position (Full Length) | Position (Truncated) | Kuma010 A.A. | A.A. relative to Kuma010/011 | % Improvement on PFPQPQLPY (SEQ ID NO: 67) | % Improvement on PFPQPQQPF (SEQ ID NO: 68) |
|---|---|---|---|---|---|
| 463 | 274 | I | A | 51% | 234% |
| 463 | 274 | I | L | 124% | 22% |
| 463 | 274 | I | M | 123% | 53% |
| 463 | 274 | I | Q | 129% | 69% |
| 463 | 274 | I | R | 29% | 110% |
| 463 | 274 | I | T | 130% | 239% |
| 463 | 274 | I | V | 256% | 141% |

Improved Production Mutations

Mutations that improve production may provide improvements in one of three categories: 1. Altering purification method; 2. increase in yield; and 3. decreasing the probability that enzymatic self-processing would occur during purification, thereby simplifying analysis. Addition of a His tag that is removable by the proteolytic activity of the polypeptides disclosed herein falls into category 1; R105H mutant appears to improve yield by ~2-fold, placing this mutation into category 2; and mutations in positions 171-174 place these mutants into category 3.

```
Kuma010 with Kuma010-Cleavable His Tag
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARPHFRMQRRAEGGFEARSQA

AAPTAYTPLDVAQAYQFPEGLDGQGQCIAIIELGGGYDEASLAQYFASLG

VPAPQVVSVSVDGASNQPTGDPKGPDGEVELDIEVAGALAPGAKFAVYFA

PDTTAGFLDAITTAIHDPTLKPSVVSISWSGPEDSWTSAAIAAMNRAFLD

AAALGVTVLAAAGDSGSTGGEQDGLYHVHFPAASPYVLACGGTRLVASGG

RIAQETVWNDGPDGGATGGGVSRIFPLPAWQEHANVPPSANPGASSGRGV

PDLAGNADPATGYEVVIDGEATVIGGTSAVAPLFAALVARINQKLGKAVG

YLNPTLYQLPADVFHDITEGNNDIANRAQIYQAGPGWDPCTGLGSPIGVR

LLQALLPSASQPQPGSSGSSGSQPQLPYGSSGSSGSHHHHHH (SEQ ID

NO: 43 (unprocessed), SEQ ID NO: 113 (processed))

Kuma011-R105H
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARPHFRMQRRAEGGFEARSQA

AAPTAYTPLDVAQAYQFPEGLDGQGQCIAIIELGGGYDEASLAQYFASLG

VPAPQVVSVSVDGASNQPTGDPEGPDGEVELDIEVAGALAPGAKFAVYFA

PDTTAGFLDAITTAIHDPTLKPSVVSISWSGPEDSWTSAAIAAMNRAFLD

AAALGVTVLAAAGDSGSTGGEQDGLYHVHFPAASPYVLACGGTRLVASGG

RIAQETVWNDGPDGGATGGGVSRIFPLPAWQEHANVPPSANPGASSGRGV

PDLAGNADPATGYEVVIDGEATVIGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 44 (unprocessed),

SEQ ID NO: 114 (processed))

Kuma011-P171A
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARAHFRMQRRAEGGFEARSQA

AAPTAYTPLDVAQAYQFPEGLDGQGQCIAIIELGGGYDEASLAQYFASLG

VPAPQVVSVSVDGASNQPTGDPEGPDGEVELDIEVAGALAPGAKFAVYFA

PDTTAGFLDAITTAIHDPTLKPSVVSISWSGPEDSWTSAAIAAMNRAFLD

AAALGVTVLAAAGDSGSTGGEQDGLYHVHFPAASPYVLACGGTRLVASGG

RIAQETVWNDGPDGGATGGGVSRIFPLPAWQEHANVPPSANPGASSGRGV

PDLAGNADPATGYEVVIDGEATVIGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 45 (unprocessed),

SEQ ID NO: 115 (processed))

Kuma011-P171R
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARRHFRMQRRAEGGFEARSQA

AAPTAYTPLDVAQAYQFPEGLDGQGQCIAIIELGGGYDEASLAQYFASLG

VPAPQVVSVSVDGASNQPTGDPEGPDGEVELDIEVAGALAPGAKFAVYFA

PDTTAGFLDAITTAIHDPTLKPSVVSISWSGPEDSWTSAAIAAMNRAFLD

AAALGVTVLAAAGDSGSTGGEQDGLYHVHFPAASPYVLACGGTRLVASGG

RIAQETVWNDGPDGGATGGGVSRIFPLPAWQEHANVPPSANPGASSGRGV

PDLAGNADPATGYEVVIDGEATVIGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 46 (unprocessed),

SEQ ID NO: 116 (processed))
```

Kuma011-P171S
MSDMEKPWKEGEEARAVLQGHARAQAPQAVDKGPVAGDERMAVTVVLRRQ
RAGELAAHVERQAAIAPHAREHLKREAFAASHGASLDDFAELRRFADAHG
LALDRANVAAGTAVLSGPDDAINRAFGVELRHFDHPDGSYRSYLGEVTVP
ASIAPMIEAVLGLDTRPVARSHFRMQRRAEGGFEARSQA
AAPTAYTPLDVAQAYQFPEGLDGQGQCIAIIELGGGYDEASLAQYFASLG
VPAPQVVSVSVDGASNQPTGDPEGPDGEVELDIEVAGALAPGAKFAVYFA
PDTTAGFLDAITTAIHDPTLKPSVVSISWSGPEDSWTSAAIAAMNRAFL
DAAALGVTVLAAAGDSGSTGGEQDGLYHVHFPAASPYVLACGGTRLVAS
GGRIAQETVWNDGPDGGATGGGVSRIFPLPAWQEHANVPPSANPGASSG
RGVPDLAGNADPATGYEVVIDGEATVIGGTSAVAPLFAALVARINQKLG
KAVGYLNPTLYQLPADVFHDITEGNNDIANRAQIYQAGPGWDPCTGLGS
PIGVRLLQALLPSASQPQP (SEQ ID NO: 47 (unprocessed),
SEQ ID NO: 117 (processed))

Kuma011-H172A
MSDMEKPWKEGEEARAVLQGHARAQAPQAVDKGPVAGDERMAVTVVLRRQ
RAGELAAHVERQAAIAPHAREHLKREAFAASHGASLDDFAELRRFADAHG
LALDRANVAAGTAVLSGPDDAINRAFGVELRHFDHPDGSYRSYLGEVTVP
ASIAPMIEAVLGLDTRPVARPAFRMQRRAEGGFEARSQA
AAPTAYTPLDVAQAYQFPEGLDGQGQCIAIIELGGGYDEASLAQYFASLG
VPAPQVVSVSVDGASNQPTGDPEGPDGEVELDIEVAGALAPGAKFAVYFA
PDTTAGFLDAITTAIHDPTLKPSVVSISWSGPEDSWTSAAIAAMNRAFLD
AAALGVTVLAAAGDSGSTGGEQDGLYHVHFPAASPYVLACGGTRLVASGG
RIAQETVWNDGPDGGATGGGVSRIFPLPAWQEHANVPPSANPGASSGRGV
PDLAGNADPATGYEVVIDGEATVIGGTSAVAPLFAALVARINQKLGKAVG
YLNPTLYQLPADVFHDITEGNNDIANRAQIYQAGPGWDPCTGLGSPIGVR
LLQALLPSASQPQP (SEQ ID NO: 48 (unprocessed),
SEQ ID NO: 118 (processed))

Kuma011-H172R
MSDMEKPWKEGEEARAVLQGHARAQAPQAVDKGPVAGDERMAVTVVLRRQ
RAGELAAHVERQAAIAPHAREHLKREAFAASHGASLDDFAELRRFADAHG
LALDRANVAAGTAVLSGPDDAINRAFGVELRHFDHPDGSYRSYLGEVTVP
ASIAPMIEAVLGLDTRPVARPRFRMQRRAEGGFEARSQA
AAPTAYTPLDVAQAYQFPEGLDGQGQCIAIIELGGGYDEASLAQYFASLG
VPAPQVVSVSVDGASNQPTGDPEGPDGEVELDIEVAGALAPGAKFAVYFA
PDTTAGFLDAITTAIHDPTLKPSVVSISWSGPEDSWTSAAIAAMNRAFLD
AAALGVTVLAAAGDSGSTGGEQDGLYHVHFPAASPYVLACGGTRLVASGG
RIAQETVWNDGPDGGATGGGVSRIFPLPAWQEHANVPPSANPGASSGRGV
PDLAGNADPATGYEVVIDGEATVIGGTSAVAPLFAALVARINQKLGKAVG
YLNPTLYQLPADVFHDITEGNNDIANRAQIYQAGPGWDPCTGLGSPIGVR
LLQALLPSASQPQP (SEQ ID NO: 49 (unprocessed),
SEQ ID NO: 119 (processed))

Kuma011-H172S
MSDMEKPWKEGEEARAVLQGHARAQAPQAVDKGPVAGDERMAVTVVLRRQ
RAGELAAHVERQAAIAPHAREHLKREAFAASHGASLDDFAELRRFADAHG
LALDRANVAAGTAVLSGPDDAINRAFGVELRHFDHPDGSYRSYLGEVTVP
ASIAPMIEAVLGLDTRPVARPSFRMQRRAEGGFEARSQA
AAPTAYTPLDVAQAYQFPEGLDGQGQCIAIIELGGGYDEASLAQYFASLG
VPAPQVVSVSVDGASNQPTGDPEGPDGEVELDIEVAGALAPGAKFAVYFA
PDTTAGFLDAITTAIHDPTLKPSVVSISWSGPEDSWTSAAIAAMNRAFLD
AAALGVTVLAAAGDSGSTGGEQDGLYHVHFPAASPYVLACGGTRLVASGG
RIAQETVWNDGPDGGATGGGVSRIFPLPAWQEHANVPPSANPGASSGRGV
PDLAGNADPATGYEVVIDGEATVIGGTSAVAPLFAALVARINQKLGKAVG
YLNPTLYQLPADVFHDITEGNNDIANRAQIYQAGPGWDPCTGLGSPIGVR
LLQALLPSASQPQP (SEQ ID NO: 50 (unprocessed),
SEQ ID NO: 120 (processed))

Kuma011-F173R
MSDMEKPWKEGEEARAVLQGHARAQAPQAVDKGPVAGDERMAVTVVLRRQ
RAGELAAHVERQAAIAPHAREHLKREAFAASHGASLDDFAELRRFADAHG
LALDRANVAAGTAVLSGPDDAINRAFGVELRHFDHPDGSYRSYLGEVTVP
ASIAPMIEAVLGLDTRPVARPHRRMQRRAEGGFEARSQA
AAPTAYTPLDVAQAYQFPEGLDGQGQCIAIIELGGGYDEASLAQYFASLG
VPAPQVVSVSVDGASNQPTGDPEGPDGEVELDIEVAGALAPGAKFAVYFA
PDTTAGFLDAITTAIHDPTLKPSVVSISWSGPEDSWTSAAIAAMNRAFLD
AAALGVTVLAAAGDSGSTGGEQDGLYHVHFPAASPYVLACGGTRLVASGG
RIAQETVWNDGPDGGATGGGVSRIFPLPAWQEHANVPPSANPGASSGRGV
PDLAGNADPATGYEVVIDGEATVIGGTSAVAPLFAALVARINQKLGKAVG
YLNPTLYQLPADVFHDITEGNNDIANRAQIYQAGPGWDPCTGLGSPIGVR
LLQALLPSASQPQP (SEQ ID NO: 51 (unprocessed),
SEQ ID NO: 121 (processed))

Kuma011-F173S
MSDMEKPWKEGEEARAVLQGHARAQAPQAVDKGPVAGDERMAVTVVLRRQ
RAGELAAHVERQAAIAPHAREHLKREAFAASHGASLDDFAELRRFADAHG
LALDRANVAAGTAVLSGPDDAINRAFGVELRHFDHPDGSYRSYLGEVTVP
ASIAPMIEAVLGLDTRPVARPHSRMQRRAEGGFEARSQA
AAPTAYTPLDVAQAYQFPEGLDGQGQCIAIIELGGGYDEASLAQYFASLG
VPAPQVVSVSVDGASNQPTGDPEGPDGEVELDIEVAGALAPGAKFAVYFA
PDTTAGFLDAITTAIHDPTLKPSVVSISWSGPEDSWTSAAIAAMNRAFLD
AAALGVTVLAAAGDSGSTGGEQDGLYHVHFPAASPYVLACGGTRLVASGG
RIAQETVWNDGPDGGATGGGVSRIFPLPAWQEHANVPPSANPGASSGRGV
PDLAGNADPATGYEVVIDGEATVIGGTSAVAPLFAALVARINQKLGKAVG
YLNPTLYQLPADVFHDITEGNNDIANRAQIYQAGPGWDPCTGLGSPIGVR
LLQALLPSASQPQP (SEQ ID NO: 52 (unprocessed),
SEQ ID NO: 122 (processed))

-continued

Kuma011-R174S
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARPHFSMQRRAEGGFEARSQA

AAPTAYTPLDVAQAYQFPEGLDGQGQCIAIIELGGGYDEASLAQYFASLG

VPAPQVVSVSVDGASNQPTGDPEGPDGEVELDIEVAGALAPGAKFAVYFA

PDTTAGFLDAITTAIHDPTLKPSVVSISWSGPEDSWTSAAIAAMNRAFLD

AAALGVTVLAAAGDSGSTGGEQDGLYHVHFPAASPYVLACGGTRLVASGG

RIAQETVWNDGPDGGATGGGVSRIFPLPAWQEHANVPPSANPGASSGRGV

PDLAGNADPATGYEVVIDGEATVIGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 53 (unprocessed),

SEQ ID NO: 123 (processed))

Kuma012: P171R; H172R
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARRRFRMQRRAEGGFEARSQA

AAPTAYTPLDVAQAYQFPEGLDGQGQCIAIIELGGGYDEASLAQYFASLG

VPAPQVVSVSVDGASNQPTGDPKGPDGEVELDIEVAGALAPGAKFAVYFA

PDTTAGFLDAITTAIHDPTLKPSVVSISWSGPEDSWTSAAIAAMNRAFLD

AAALGVTVLAAAGDSGSTGGEQDGLYHVHFPAASPYVLACGGTRLVASGG

RIAQETVWNDGPDGGATGGGVSRIFPLPAWQEHANVPPSANPGASSGRGV

PDLAGNADPATGYEVVIDGEATVIGGTSAVAPLFAALVARINQKLGKAVG

YLNPTLYQLPADVFHDITEGNNDIANRAQIYQAGPGWDPCTGLGSPIGVR

LLQALLPSASQPQP (SEQ ID NO: 54 (unprocessed),

SEQ ID NO: 124 (processed))

As used throughout the present application, the term "polypeptide" is used in its broadest sense to refer to a sequence of subunit amino acids, whether naturally occurring or of synthetic origin. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, or glycosylation. Such linkage can be covalent or non-covalent as is understood by those of skill in the art. The polypeptides may be linked to any other suitable linkers, including but not limited to any linkers that can be used for purification or detection (such as FLAG or His tags).

In another aspect, the present invention provides isolated nucleic acids encoding the polypeptide of any aspect or embodiment of the invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In a further aspect, the present invention provides nucleic acid expression vectors comprising the isolated nucleic acid of any embodiment of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In another aspect, the present invention provides recombinant host cells comprising the nucleic acid expression vectors of the invention. The host cells can be either prokaryotic or eukaryotic. The cells can be transiently or stably transfected or transduced. Such transfection and transduction of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, 2$^{nd}$ Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, cell pellet, or recovered from the culture medium. Methods to purify recombinantly expressed polypeptides are well known to the man skilled in the art.

In a further aspect, the present invention provides pharmaceutical compositions, comprising the polypeptide, nucleic acid, nucleic acid expression vector, and/or the recombinant host cell of any aspect or embodiment of the invention, and a pharmaceutically acceptable carrier. The pharmaceutical compositions of the invention can be used, for example, in the methods of the invention described below. The pharmaceutical composition may comprise in addition to the polypeptides, nucleic acids, etc. of the invention (a) a lyoprotectant, (b) a surfactant: (c) a bulking agent; (d.) atonicity adjusting agent; (e) stabilizer; (f) a preservative and/or (g) a buffer.

In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, Jia-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosinotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides, nucleic acids, etc. of the invention may be the sole active agent in the pharmaceutical composition, or the composition may further comprise one or more other active agents suitable for an intended use.

The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

The compositions described herein could also be provided as a dietary supplement as described by the US regulatory agencies.

These compositions can be prepared in a manner well known in the pharmaceutical art, and can be administered by any suitable route. In a preferred embodiment, the pharmaceutical compositions and formulations are designed for oral administration. Conventional pharmaceutical carriers, aqueous, powder or oily bases, thickeners and the like may be necessary or desirable.

The pharmaceutical compositions can be in any suitable form, including but not limited to tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

In another aspect, the present invention provides methods for treating celiac sprue or non-celiac gluten sensitivity (NCGS), comprising administering to an individual with celiac sprue or NCGS an amount effective to treat the celiac sprue or NCGS of one or more polypeptides selected from the group consisting of the polypeptides of the of the invention, or using one or more of these polypeptides to process food for consumption by individuals with celiac sprue or NCGS The inventors of the present invention have discovered that the polypeptides of the invention are capable of degrading proline (P)- and glutamine (Q)-rich components of gluten known as 'gliadins' believed responsible for the bulk of the immune response in most celiac sprue patients. The polypeptides of the present invention show superior activity in degrading peptides having a PQLP (SEQ ID NO: 65) or PQQP (SEQ ID NO: 66) motif (such as PFPQPQLPY (SEQ ID NO: 67) and/or PFPQPQQPF (SEQ ID NO: 68)), which are substrates representative of gliadin) at pH 4 compared to Kuma010/011 and other polypeptides disclosed as useful for treating celiac sprue (WO2015/023728). Thus, the polypeptides of the invention constitute significantly improved therapeutics for treating celiac sprue and NCGS.

Celiac sprue (also known as celiac disease or gluten intolerance) is a highly prevalent disease in which dietary proteins found in wheat, barley, and rye products known as 'glutens' evoke an immune response in the small intestine of genetically predisposed individuals. The resulting inflammation can lead to the degradation of the villi of the small intestine, impeding the absorption of nutrients. Symptoms can appear in early childhood or later in life, and range widely in severity, from diarrhea, fatigue, weight loss, abdominal pain, bloating, excessive gas, indigestion, constipation, abdominal distension, nausea/vomiting, anemia, bruising easily, depression, anxiety, growth delay in children, hair loss, dermatitis, missed menstrual periods, mouth ulcers, muscle cramps, joint pain, nosebleeds, seizures, tingling or numbness in hands or feet, delayed puberty, defects in tooth enamel, and neurological symptoms such as ataxia or paresthesia. There are currently no effective therapies for this lifelong disease except the total elimination of glutens from the diet. Although celiac sprue remains largely underdiagnosed, its' prevalence in the US and Europe is estimated at 0.5-1.0% of the population. In addition to celiac sprue, a significant fraction of the population is thought to suffer from the condition of non-celiac gluten sensitivity (NCGS), which is caused by the ingestion of gluten but is mechanistically distinct from celiac disease, though the symptoms are frequently indistinguishable from those of celiac sprue.

As used herein, "treating celiac sprue or NCGS" means accomplishing one or more of the following: (a) reducing the severity of celiac sprue or NCGS; (b) limiting or preventing development of symptoms characteristic of celiac sprue or NCGS; (c) inhibiting worsening of symptoms characteristic of celiac sprue or NCGS; (d) limiting or preventing recurrence of celiac sprue or NCGS in patients that have previously had the disorder; (e) limiting or preventing recurrence of symptoms in patients that were previously symptomatic for celiac sprue or NCGS; and (f) limiting development of celiac sprue or NCGS in a subject at risk of developing celiac sprue or NCGS, or not yet showing the clinical effects of celiac sprue or NCGS.

The individual to be treated according to the methods of the invention may be any individual suffering from celiac sprue or NCGS, including human subjects. The individual may be one already suffering from symptoms or one who is asymptomatic.

As used herein, an "amount effective" refers to an amount of the polypeptide that is effective for treating celiac sprue. The polypeptides are typically formulated as a pharmaceutical composition, such as those disclosed above, and can be administered via any suitable route, including orally, parentally, by inhalation spray, or topically in dosage unit formulations containing conventional pharmaceutically acceptable carriers, adjuvants, and vehicles. In a preferred embodiment, the pharmaceutical compositions and formulations are orally administered, such as by tablets, pills, lozenges, elixirs, suspensions, emulsions, solutions, or syrups.

Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The polypeptides can be delivered in a single bolus, or may be administered more than once (e.g., 2, 3, 4, 5, or more times) as determined by an attending physician.

EXAMPLE 1

Gliadin is highly enriched in proline (P) and glutamine (Q), which renders it recalcitrant to degradation by human digestive enzymes. PQ-rich peptide fragments derived from partial digestion of gliadin are deamidated in the intestinal lumen, thereby allowing binding to HLA-DQ2 or DQ8, and stimulation of a Th1 inflammatory response in people with CD[3]. The gliadin endopeptidase KUMAMAX™ (hereafter referred to as Kuma011, or Kuma 010 if referring to Kuma011 including the C-terminal histidine tag: GSTEN-LYFQSGALEHHHHHH (SEQ ID NO: 139)), which demonstrates stability and functionality in gastric conditions, was previously engineered to break down peptides containing the PQ dipeptide motif. Based on the crystal structure of Kuma010 (PDB ID 4NE7), we redesigned the active site of Kuma010 selecting for mutations to increase activity against immunogenic gliadin peptides. Designed mutants were then screened for increased activity against the highly immunogenic 33mer (LQLQPFPQPQLPYPQPQLPYPQPQLPYPQPQPF (SEQ ID NO: 69)) and 26mer (FLQPQQPFPQQPQQPYPQQPQQPFPQ (SEQ ID NO: 70)) gliadin peptides[6,7]. These peptides harbor either the PQL or PQQ tripeptide motif, representative of all gliadin T cell epitopes shown to be toxic for the vast majority of celiac patients[8]. In this manner, the variant Kuma030 was built. Kuma030 is 44-fold more active against peptides containing PQQ, and 11-fold more active against peptides containing PQL, than Kuma010.

Based on the molecular modeling, the putative S1' peptide binding interface of Kuma010 consists of entirely hydrophobic residues, and should therefore prefer hydrophobic residues such as leucine, and not polar residues such as glutamine, at P1'. The S1' binding pocket of Kuma030 introduces an isoleucine to threonine mutation (I463T), which is predicted to provide a hydrogen bond with a P1' glutamine, enabling this enzyme to accommodate both leucine and glutamine in the S1' subsite and thereby target both PQL and PQQ tripeptides. Kuma030 also incorporates six additional mutations (K262E, E269T, S354Q, G358S, D399Q, A449Q) that provide enhanced catalytic efficiency on the 26mer and 33mer peptides. G358S is predicted to stabilize the loop containing an engineered histidine introduced in Kuma010 which is predicted to hydrogen bond to the P1 glutamine residue. The remaining mutations are predicted to stabilize the protein structure as modeled.

While dozens of PQ-rich epitopes have been linked to CD, several peptides derived from gliadin (wheat), hordein (barley), and secalin (rye) have been shown to account for the vast majority of the immune response in CD and have thus been classified as immunodominant[8]. In wheat, these include the peptides W02-E07 (LQPFPQPQLPYPQPQ (SEQ ID NO: 133)), W03-E07 (QPFPQPQQPFPWQP (SEQ ID NO: 134)), and the 33mer peptide, which contains the W02-E07 sequence[6,9]. These peptides harbor several epitopes shown to be highly immunogenic[9-11]. To evaluate the ability of Kuma030 to destroy these epitopes throughout gluten, purified whole gluten was incubated with Kuma030 under simulated gastric conditions (pH 4.0 at 37° C. with 0.6 mg mL$^{-1}$ pepsin)[12]. The gluten fraction remaining after degradation was quantified using ELISA assays based on either the R5 or G12 antibodies recognizing the amino acid motifs QQPFP (SEQ ID NO: 135) and QPQLPY (SEQ ID NO: 136), respectively, which encompass all of the immunodominant epitopes in the above peptides[13,14]. To compare the activity of Kuma030 to that of published glutenases, we also examined the glutenases EPB2 and SCPEP, which are currently being pioneered at a 1:1 ratio as a combination enzyme therapeutic for CD[15]. The EPB2 and SCPEP enzymes generated in this work were verified to have activities consistent with that of published values[16,17]. Upon incubation with gluten, we observed a dose-dependent reduction in the QQPFP (SEQ ID NO: 135) or QPQLPY (SEQ ID NO: 136) load using either Kuma030, Kuma010, or a 1:1 combination of EPB2 and SCPEP (FIG. 1A). At a 1:25 w:w ratio of enzyme:gluten, EPB2 and SCPEP broke down 84.8% of the gluten present, consistent with previously published reports of this enzyme combination[18,19]. Kuma030 was highly effective at eliminating these peptide epitopes throughout gluten, with a 1:400 w:w ratio of enzyme:gluten being sufficient to reduce the immunogenic gluten present by over 99.5% at 60 minutes, as quantified by both methods used (FIG. 1A). Kuma030-dependent reduction in immunogenic gluten load is rapid, with >98% degradation achieved by 5 minutes at a w:w ratio of 1:25 (FIG. 1B). Mass spectroscopy of the Kuma030 cleavage products revealed that Kuma030 cleaved each peptide after the PQ dipeptide motif in the immunodominant epitopes from wheat (33mer, W02-E07, and W03-E07), and also those from barley B08-E2E7 (PQQPIPQQPQPYPQQ (SEQ ID NO: 61)) and rye R11-E2E7 (QPFPQQPEQIIPQQP)[9] (SEQ ID NO: 62) (FIG. 1C). While these intact peptides are highly immunostimulatory, the peptide breakdown products are not predicted to stimulate the immune system, since Kuma030 action results in elimination of the core 9mer epitope thought to trigger the immune response[20]. The ability of Kuma030 to cleave these peptides containing either a PQL or a PQQ tripeptide motif, and to reduce the gliadin load as measured by both G12 and R5 antibodies, are consistent with the hypothesis that Kuma030 can bind and cleave peptides with either a leucine or a glutamine in the S1' binding pocket.

The ability of Kuma030 to efficiently degrade immunogenic gliadin epitopes suggests that incubation of gliadin with Kuma030 might reduce its capacity to stimulate a T-cell mediated immune response. T cell assays utilizing cells derived from the intestinal biopsies of celiac patients represent the gold standard for this evaluation. To directly evaluate the hypothesis that incubation with Kuma030 would decrease or eliminate the immunostimulatory capacity of gliadin, we performed T cell assays in which cells were exposed to Kuma030-treated gliadin and the resulting T cell reaction was assessed. The highly gliadin-reactive intestinal CD4$^+$ T cell lines used in this study were previously generated from intestinal mucosa and have been shown to react to a diversity of epitopes across different gliadin families[21]. Kuma030 and pepsin were incubated with purified wheat gliadin in laboratory-simulated gastric conditions for 60 minutes. In order to mimic transit into the intestinal compartment, the pH levels of the samples were then increased, and the samples were treated with chymotrypsin and deamidated with TG2 to unmask the immunogenic epitopes. The resulting gliadin samples were presented to T cell lines, and stimulation was assessed by measuring IFN-γ production (FIGS. 2A-E) and T cell proliferation (FIG. 3A-D). Exposure of T cell lines to pepsin-treated gliadin resulted in stimulation of production of IFN-γ, and co-treatment of gliadin with pepsin and Kuma030 reduced this response, eliminating it at higher concentrations. The decreases observed in IFN-γ production were not due to Kuma030 toxicity. Importantly, Kuma030 eliminated the T cell response to gliadin in every T cell line tested regardless of T cell epitope specificity, indicating that Kuma030 is effective against all epitopes recognized by the T cell lines used in this assay. Since these epitopes span the three major gliadin families: α-, ω-, and γ-gliadin, this suggests that Kuma030 is capable of degrading immunogenic epitopes within all relevant regions of gliadin.

Figure 4:
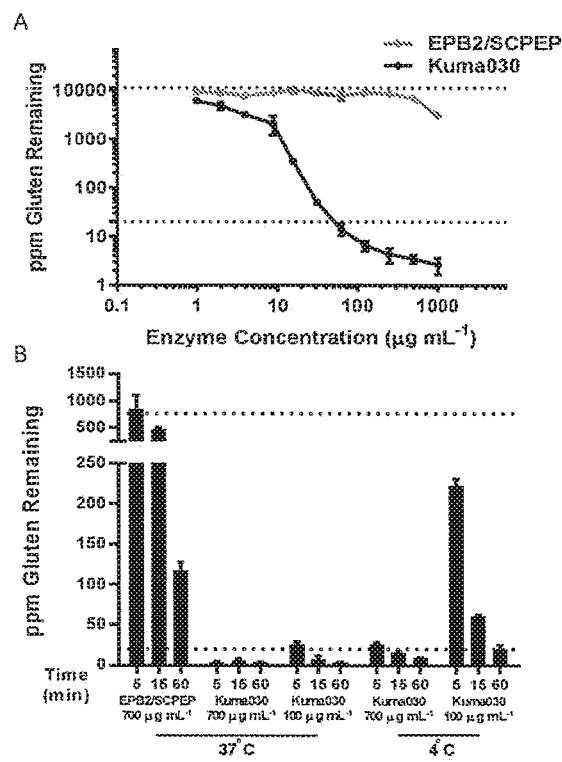
FIG. 4. Kuma030 efficiently degrades gluten in complex food matrices. (A) The amount of gluten remaining in whole wheat bread after a 30 minute incubation with either Kuma030 or a 1:1 combination of EPB2:SCPEP at the indicated enzyme concentrations. The starting concentration of gluten was 10,000 ppm. Note both axes are plotted on a logarithmic scale. (B) The amount of gluten remaining in a wheat beer after incubation with the indicated concentrations of either a 1:1 ratio of EPB2:SCPEP, or Kuma030, at 37° C. or 4° C., at 5, 15, or 60 minutes. Gluten was detected using the G12 ELISA method.

The experiments above demonstrate the ability of Kuma030 to degrade immunogenic gliadin epitopes in the context of purified whole gluten or gliadin. However, to assess practical application, it is important to evaluate Kuma030 effectiveness in physiologically relevant food and beverage matrices. To assess the activity of Kuma030 in gastric digestion scenarios, we tested the ability of Kuma030 to break down gluten in an acidified bread slurry and in a wheat beer. Whole-wheat bread was mashed in artificial saliva to simulate mastication at a bread concentration representative of that in the stomach after ingestion of one slice of bread. The mixture was then acidified by the addition of HCl and pepsin, and glutenases at various concentrations were added. The amount of gluten remaining was then quantified after 30 minutes of digestion, which represents the average lag time of food in the stomach before the commencement of ingesta release into the duodenum through the pyloric opening[22]. At the highest concentration of glutenase tested (1000 μg mL$^{-1}$), treatment with EPB2 and SCPEP resulted in 84.4% gluten degradation (FIG. 4A). This is comparable to published results from a Phase I study showing that EPB2 and SCPEP eliminate 70-79% of gluten in a test meal at a 1:10 enzyme:gluten ratio in the human stomach after a 30 minute incubation time[23]. At a concentration of 62.5 μg mL$^{-1}$ (a 1:160 w:w ratio), Kuma030 reduced the level of gluten in the bread to below 20 ppm (the FDA threshold for "gluten free" labeling). Finally, the gluten-degrading ability of Kuma030 was tested directly in a wheat beer, since wheat beers demonstrate comparatively high gluten levels[24]. Beer was incubated with Kuma030 at 37° C. or 4° C. at two enzyme concentrations. Samples were taken at various timepoints and the concentration of remaining gluten was quantified. We found that incubation of beer, which demonstrated a gluten concentration of ~764 ppm, with Kuma030 decreased the gluten level to below 20 ppm by only 5 minutes (FIG. 4B). The rapidity of this effect is particularly important since liquids empty through the stomach considerably faster than solids[25]. Surprisingly, Kuma030 significantly reduced the gluten load of wheat beer even at 4° C., as incubation with the Kuma030 at 700 μg mL$^{-1}$ reduced the gluten levels to below 20 ppm by 5 minutes.

At this time, the only therapy for celiac disease is a lifelong strict gluten free diet. Oral enzyme therapy has been considered an attractive treatment option for CD since the identification of PQ-rich immunogenic gliadin epitopes that stimulate the immune response[3]. A useful characteristic of any oral enzyme therapeutic for CD is the ability to break down immunogenic peptides in gastric conditions, since the inflammatory immune response to gliadin occurs immediately upon entering the intestine[26]. Gluten challenge studies in CD patients have shown that the ingested gluten load must be kept at 10 mg or less in order to prevent intestinal damage[27,28]. Indeed, the FDA currently mandates that any food labeled as "gluten free" must demonstrate less than 20 ppm gluten, since strict adherence to this standard is predicted to result in a daily ingestion of 10 mg or less. Thus, the accidental ingestion of 1 g of gluten (approximately the amount of gluten present in a crouton) must be reduced by 99% or greater in the gastric compartment in order to prevent the intestinal damage and symptoms that would arise from gluten exposure. There is therefore a clear need for glutenases that can rapidly destroy immunogenic gliadin epitopes in gastric conditions. In a bread slurry model representing ingestion of 4 g of gluten, Kuma030 was found to degrade >99.8% of the gliadin load in 30 minutes at a 1:160 w:w ratio. Additionally Kuma030 specifically destroys peptides with the PQ dipeptide motif, which is commonly found throughout the immunogenic regions of gluten. Indeed, Kuma030 is capable of degrading all immunodominant peptides tested, and gliadin treated with Kuma030 failed to stimulate IFN-γ production by all T cell lines tested, which is significant since CD patients demonstrate a myriad of responses to different immunogenic epitopes.

REFERENCES FOR EXAMPLE 1

1. Rubio-Tapia, A., Ludvigsson, J. F., Brantner, T. L., Murray, J. A. & Everhart, J. E. The prevalence of celiac disease in the United States. Am J Gastroenterol 107, 1538-1544; quiz 1537, 1545 (2012).
2. Catassi, C., Gatti, S. & Lionetti, E. World perspective and celiac disease epidemiology. Dig Dis 33, 141-146 (2015).

3. Sollid, L. M. Coeliac disease: dissecting a complex inflammatory disorder. Nat Rev Immunol 2, 647-655 (2002).
4. Gordon, S. R., et al. COMPUTATIONAL DESIGN OF AN alpha-GLIADIN PEPTIDASE. J Am Chem Soc (2012).
5. Richter, F., Leaver-Fay, A., Khare, S. D., Bjelic, S. & Baker, D. De novo enzyme design using Rosetta3. PLoS One 6, e19230 (2011).
6. Shan, L., et al. Structural basis for gluten intolerance in celiac sprue. Science 297, 2275-2279 (2002).
7. Shan, L. Identification and analysis of multivalent proteolytically resistant peptides from gluten: implications for celiac sprue. Journal of Proteome Research (2005).
8. Sollid, L. M., Qiao, S. W., Anderson, R. P., Gianfrani, C. & Koning, F. Nomenclature and listing of celiac disease relevant gluten T-cell epitopes restricted by HLA-DQ molecules. Immunogenetics 64, 455-460 (2012).
9. Tye-Din, J. A., et al. Comprehensive, quantitative mapping of T cell epitopes in gluten in celiac disease. Sci Transl Med 2, 41ra51 (2010).
10. Arentz-Hansen, H., et al. The intestinal T cell response to alpha-gliadin in adult celiac disease is focused on a single deamidated glutamine targeted by tissue transglutaminase. J Exp Med 191, 603-612 (2000).
11. Arentz-Hansen, H., et al. Celiac lesion T cells recognize epitopes that cluster in regions of gliadins rich in proline residues. Gastroenterology 123, 803-809 (2002).
12. Chang, J. H., et al. A novel placement method of the Bravo wireless pH monitoring capsule for measuring intragastric pH. Dig Dis Sci 54, 578-585 (2009).
13. Lupo, A., Roebuck, C., Walsh, A., Mozola, M. & Abouzied, M. Validation study of the Veratox R5 rapid ELISA for detection of gliadin. J AOAC Int 96, 121-132 (2013).
14. Moron, B., et al. Sensitive detection of cereal fractions that are toxic to celiac disease patients by using monoclonal antibodies to a main immunogenic wheat peptide. Am J Clin Nutr 87, 405-414 (2008).
15. Landeaho, M. L., et al. The Glutenase ALV003 Attenuates Gluten-Induced Mucosal Injury in Patients with Celiac Disease. Gastroenterology (2014).
16. Bethune, M. T., Strop, P., Tang, Y., Sollid, L. M. & Khosla, C. Heterologous expression, purification, refolding, and structural-functional characterization of EP-B2, a self-activating barley cysteine endoprotease. Chem Biol 13, 637-647 (2006).
17. Ehren, J., Govindarajan, S., Moron, B., Minshull, J. & Khosla, C. Protein engineering of improved prolyl endopeptidases for celiac sprue therapy. Protein Eng Des Sel 21, 699-707 (2008).
18. Siegel, M., et al. Rational design of combination enzyme therapy for celiac sprue. Chem Biol 13, 649-658 (2006).
19. Gass, J., Bethune, M. T., Siegel, M., Spencer, A. & Khosla, C. Combination enzyme therapy for gastric digestion of dietary gluten in patients with celiac sprue. Gastroenterology 133, 472-480 (2007).
20. Petersen, J., et al. T-cell receptor recognition of HLA-DQ2-gliadin complexes associated with celiac disease. Nat Struct Mol Biol 21, 480-488 (2014).
21. Camarca, A., et al. Intestinal T cell responses to gluten peptides are largely heterogeneous: implications for a peptide-based therapy in celiac disease. J Immunol 182, 4158-4166 (2009).
22. Pera, P., et al. Influence of mastication on gastric emptying. J Dent Res 81, 179-181 (2002).
23. Siegel, M., et al. Safety, tolerability, and activity of ALV003: results from two phase 1 single, escalating-dose clinical trials. Dig Dis Sci 57, 440-450 (2012).
24. Picariello, G., et al. Proteomics, peptidomics, and immunogenic potential of wheat beer (weissbier). J Agric Food Chem 63, 3579-3586 (2015).
25. Houghton, L. A., et al. Relationship of the motor activity of the antrum, pylorus, and duodenum to gastric emptying of a solid-liquid mixed meal. Gastroenterology 94, 1285-1291 (1988).
26. Castillo, N. E., Theethira, T. G. & Leffler, D. A. The present and the future in the diagnosis and management of celiac disease. Gastroenterol Rep (Oxf) 3, 3-11 (2015).
27. Catassi, C., et al. A prospective, double-blind, placebo-controlled trial to establish a safe gluten threshold for patients with celiac disease. Am J Clin Nutr 85, 160-166 (2007).
28. Akobeng, A. K. & Thomas, A. G. Systematic review: tolerable amount of gluten for people with coeliac disease. Aliment Pharmacol Ther 27, 1044-1052 (2008).

EXAMPLE 2

Computationally designed enzymes were then produced and tested for their ability to break down immunogenic gliadin peptides. Mutations that were shown to improve the ability of the enzyme to target relevant peptides were then combined and tested in an iterative process to further increase activity. More recently, design has been extended to the S1' binding pocket to prefer either L or Q amino acids. This engineering effort has greatly increased activity on peptides containing a PQL or PQQ tripeptide, which are located within the core epitope of virtually all immunogenic gliadin peptides.

Several Kuma010 variants are used. The specific mutational differences, and their relative effects on activity, are listed in Table 6 below.

TABLE 6

| Variant | Background[a] | Mutation[b] | Activity Improvement over Background[c] |
|---|---|---|---|
| Kuma010 | Kumamolisin-As | V119D | 116x |
| | | S262K | |
| | | N291D | |
| | | D293T | |
| | | G319S | |
| | | D358G | |
| | | D368H | |

TABLE 6-continued

| Variant | Background[a] | Mutation[b] | Activity Improvement over Background[c] |
|---|---|---|---|
| Kuma020 | Kuma010 | G358S<br>I463T | 7-19x (PQL)<br>15-35x (PQQ) |
| Kuma021 | Kuma020 | D399Q<br>A449Q | 1-2x (PQL)<br>1.2-2.5x (PQQ) |
| Kuma030 | Kuma021 | K262E<br>E267T<br>S354Q | 1.2-2x (PQL)<br>1.2-2x (PQQ) |
| Kuma031 | Kuma030 | GSTENLYFQSGALEHHHHHH (SEQ ID NO: 139) Deleted from C-terminus | No change (PQL); production mutant |
| Kuma032 | Kuma031 | P171R<br>H172R | No change (PQL)); production mutant |
| Kuma040 | Kuma010 | S319A<br>H368F<br>D399Q<br>A449Q<br>I463T | 35-50x (PQL)<br>30-40x (PQQ); Kuma030 is 2-fold more active on PQQ, and 2-fold less active on PQL, than Kuma040 |
| Kuma041 | Kuma040 | GSTENLYFQSGALEHHHHHH (SEQ ID NO: 139) Deleted from C-terminus | 1.0-1.2x (PQL) |
| Kuma042 | Kuma041 | P171R<br>H172R | 1.2-1.5x (PQL) |
| Kuma050 | Kuma021 | K262E<br>E267T<br>S354Q<br>L270V<br>T463I | 1.5-2x (PQL)<br>0.01-0.2x (PQQ) |
| Kuma060 | Kuma030 | G320M | In bread assays. Kuma060 is about twice as active as Kuma030 |
| Kuma061 | Kuma060 | GSTENLYFQSGALEHHHHHH (SEQ ID NO: 139) Deleted from C-terminus | about same activity as Kuma060. |
| Kuma062 | Kuma061 | P171R<br>H172R | ND[d]; about same activity as Kuma060. |
| Kuma070 | Kuma040 | G320M | 2-3x (PQL)<br>2-4x (PQQ) |
| Kuma071 | Kuma070 | GSTENLYFQSGALEHHHHHH (SEQ ID NO: 139) Deleted from C-terminus | ND[d]; about 0.2X as active as Kuma 070 |

TABLE 6-continued

| Variant | Background[a] | Mutation[b] | Activity Improvement over Background[c] |
|---|---|---|---|
| Kuma072 | Kuma070 | GSTENLYFQSGALEHHHHHH (SEQ ID NO: 139) Deleted from C-terminus P171R H172R | about 0.7X as active as Kuma 070; |

[a]The specific Kuma010 variant that served as a background upon which the listed mutations were made.
[b]Mutational positions are denoted relative to the full-length Kuma010 enzyme.
[c]Activity Improvement was calculated for each variant as a fold increase in activity relative to that of the "background" enzyme, the template enzyme used to make that variant. Activity was measured on one or more of the following substrates: a fluorescent-labeled PQPQLP (SEQ ID NO: 156) substrate, the 33mer[5] (contains PQL) or 26mer[6] (contains PQQ) peptides, or DQ2.5-glia-α1a (contains PQL) or DQ2.5-glia-ω1 (contains PQQ)[7]. It is important to note that since hundreds of Kuma010 variants were testes, it would have been impractical to obtain kinetic constants for each mutant, thus the fold improvement numbers shown here are estimates instead of definitive numbers. The fold improvement numbers presented here are calculated from the amount of peptide degradation product detected in the degradation assay by LC-MS.
[d]ND: not determined. The activities of leads Kuma060, Kuma061, and Kuma062; and Kuma070, Kuma071, and Kuma072; were compared directly to each other in bread or meal degradation assays instead of by assessment of individual peptide degradation in order to confirm that no decrease in enzymatic activity occurred upon loss of the His tag. The ability of Kuma070 to break down PQL- and PQQ-containing peptides was compared to Kuma040 as discussed below.

Kuma020, Kuma021, and Kuma030

The active site of Kuma010 underwent further design effort to improve activity against substrates containing either PQL or PQQ tripeptides. Engineering efforts identified the mutations G358S and I463T as important contributors to increased activity. The G358S mutation was a refinement to a previous mutation made at this site in Kuma010. The I463T mutation eliminated the steric hindrance encountered in the P1' binding pocket when targeting PQL tripeptide motifs, and introduced a new predicted hydrogen bond when PQQ was the substrate[4]. The Kuma010 variant harboring these two mutations demonstrated a very large improvement over the original Kuma010 and was named Kuma020.

Additional mutations were made to this Kuma020 enzyme. D399Q and A449Q were mutations that were located outside of the active site, and so are not predicted to affect binding to the substrate. Instead, these two mutations resulted in new predicted intramolecular hydrogen bonds and were thus predicted to stabilize the enzyme. The resulting variant, Kuma021, showed a further increase in activity.

Three other refinements contributed to the generation of Kuma030 from Kuma021. Kuma030 is described in detail above.

Kuma040 and Kuma050

As an alternative to the mutations listed above, a different set of mutations on the Kuma010 background, S319A and H368F, led to a different active site architecture than the one found in Kuma030. Together these mutations, along with D399Q, A449Q, and I463T, (mutations that also increased activity in Kuma030) make up the Kuma040 variant. Kuma041, Kuma042, Kuma070, Kuma071, and Kuma072 have Kuma040-like active sites, while Kuma031, Kuma032, Kuma060, Kuma061, and Kuma062 have Kuma030-like active sites.

Kuma050 is a Kuma010 variant built on the Kuma021 background with an active site architecture that has more in common with Kuma030 than Kuma040. However, Kuma050 lacks the I463T mutation, and instead harbors a L270V mutation which is predicted to increase its activity against PQL-containing peptides but is predicted to hinder glutamine from accessing the P1' binding pocket, thereby decreasing activity on PQQ-containing substrates. Accordingly, Kuma050 specifically demonstrates a high level of activity against substrates containing PQL, but not against substrates containing PQQ. The specificity profile of Kuma050 was desired due to the fact that several studies have indicated that the immunodominant 33mer peptide from α-gliadin, which contains several PQL motifs and no PQQ motifs, may be the peptide responsible for the vast majority of the disease in a subset of patients.

Figure 5:
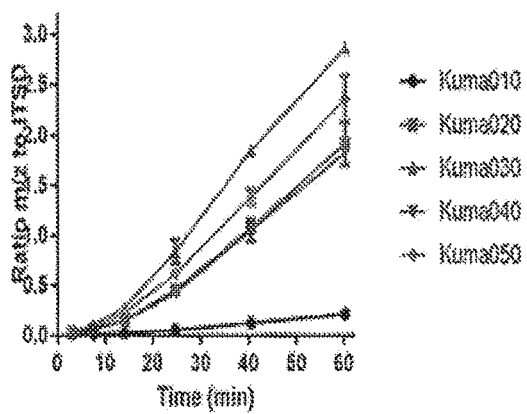
FIG. 5. Comparison of 26-mer and 33-mer degradative abilities of Kuma010, Kuma020, Kuma030, Kuma040, and Kuma050. Enzymes were incubated at 2 µg mL$^{-1}$ with 1 mg mL$^{-1}$ of either the 33mer peptide (FIG. 5a) or the 26mer peptide (FIG. 5b) for 60 minutes. Samples were taken at the indicated timepoints, and the concentrations of peptide breakdown products were measured. Breakdown products were: from the 33mer peptide (SEQ ID NO: 69), LPYPQPQF (SEQ ID NO: 137); from the 26mer peptide (SEQ ID NO: 70), QPYPQ (SEQ ID NO: 147). Activities are graphed as the ratio of the appropriate m/z signal to that of the internal standard.
Figure 5:
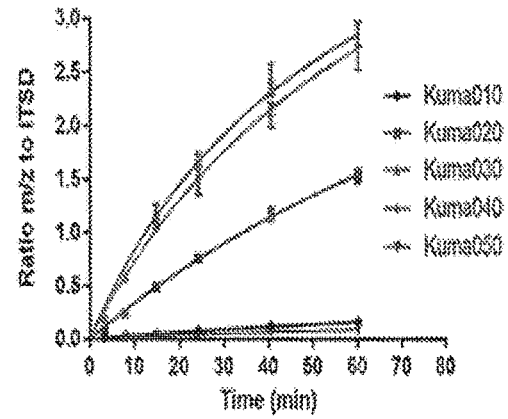

The activities of Kuma010, Kuma020, Kuma030, Kuma040, and Kuma050 are shown below for the highly immunogenic 33mer peptide of α-gliadin (LQLQPFPQPQLPYPQPQLPYPQPQLPYPQPQPF (SEQ ID NO: 69)) and the 26mer peptide of γ-gliadin (FLQPQQPFPQQPQQPYPQQPQQPFPQ (SEQ ID NO: 70)), which represent PQL- and PQQ-containing peptides, respectively. The appearance of breakdown products over time (LPYPQPQPF (SEQ ID NO: 137) for 33mer peptide; FLQPQ (SEQ ID NO: 138) for 26mer peptide) are shown in FIGS. 5A-B.

In both cases, Kuma030 was the dominant enzyme tested, though Kuma040 demonstrated activity almost as potent as Kuma030 especially against the 26mer peptide. As expected, Kuma050 demonstrated good activity on the 33mer peptide, but very poor activity on the 26mer peptide. Compared to Kuma030 and Kuma040, Kuma020 demonstrated a moderate amount of activity on both peptides, consistent with it being a design intermediate as shown above. All variants demonstrate a marked improvement on the original Kuma010 enzyme.

Kuma060 and Kuma070

An additional designed mutation was the mutation G320M. This mutation did not appear particularly promising as it was not predicted to greatly improve activity, and indeed, this residue, while in the active site, does not appear to make direct contact with the gliadin substrate. However, mutation at this position improved activity by 2-4 fold on both substrates. This could be due to slight changes in the Kuma010 backbone incurred by incorporation of the methionine, rendering it into a confirmation that is even more favorable for catalysis. The G320M mutation was incorporated into the Kuma030 and Kuma040 backgrounds to generate enzymes Kuma060 and Kuma070, respectively.

Figure 6:
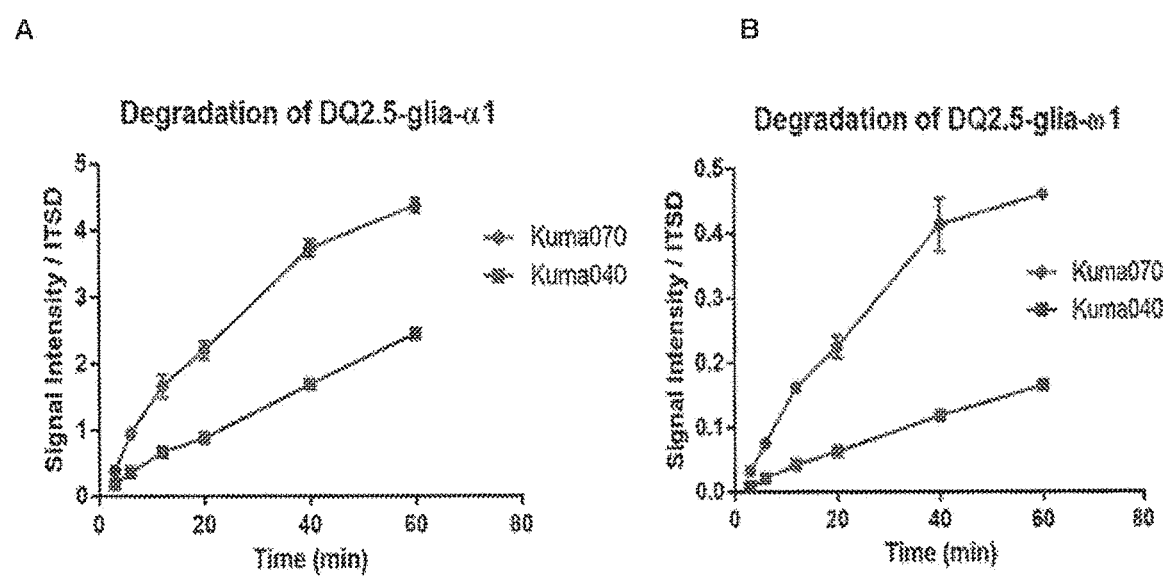
FIG. 6. The G320M mutation improves activity by 2-4 fold. Shown is activity in degradation of immunogenic epitopes DQ2.5-glia-α1a (contains PQL) (FIG. 6a), and DQ2.5-glia-ω1 (contains PQQ) (FIG. 6b). Samples were taken at the indicated timepoints, and the concentration of peptide breakdown product PFPQPQ (SEQ ID NO: 148) was measured. Activities are graphed as the ratio of the appropriate m/z signal to that of the internal standard.

FIGS. 6A-B show the improvement in activity attributed to the G320M mutation on the Kuma040 background in degradation of both immunogenic epitopes DQ2.5-glia-α1a (contains PQL), and DQ2.5-glia-ω1 (contains PQQ).
The KumaXX1 and KumaXX2 Series With the exception of Kuma021, Kuma010 variants labeled KumaXX1 (ex. Kuma031) correspond to the KumaXX0 variant (ex. Kuma030) in which the C-terminal TEV protease cut site and 6×His tag have been genetically deleted (GSTENLYFQSGALEHHHHHH (SEQ ID NO: 139)). This tag, which was originally added to the Kuma-molisin-As enzyme for high-throughput, easy purification of Kuma010 variants, was removed in certain Kuma010 lead variants as the 6× His tag is not preferable on biologic pharmaceuticals. In general, the removal of this tag did not affect the activity of the enzyme, though His tag removal did appear to result in a slight decrease in the ability of the Kuma070 enzyme (but not the Kuma060 enzyme) to degrade gliadin in a gastric digestion of whole wheat bread.

Kuma010 variants labeled KumaXX2 (ex Kuma032) also lack the His tag, and contain the following additional mutations: P171R and H172R. These mutations don't affect activity of the enzyme, but were incorporated to simplify the purification process. These mutations were introduced into the propeptide domain in the N-terminal region of Kuma010. Since these mutations lie within the propeptide domain, they are not present in the mature, active enzyme. These two mutations fall within the N-terminal region of the protein that sits in the enzyme's active site before cleavage upon exposure to low pH. Since this region is in proximity of the catalytic residues, it is hypothesized that this is the region that undergoes the initial cleavage event upon purification of the Kuma010 enzyme during standard purification procedures. The partially cleaved enzyme N-terminus remains tightly associated with the mature enzyme until the enzyme is exposed to acid. While this initial self-processing during protein purification does not negatively affect activity, it can complicate interpretation of SDS-PAGE analysis by individuals unfamiliar with the Kuma010 enzyme. Thus, in order to simplify the SDS-PAGE profile of purified enzyme, the P171R and H172R mutations were incorporated to reduce the amount of initial N-terminal cleavage that occurs during the protein purification process.

Figure 7:
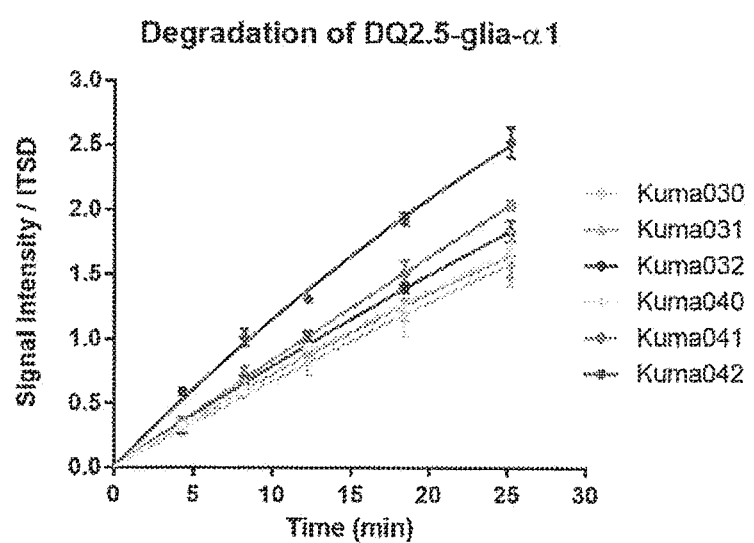
FIG. 7. P171R and H172R mutations do not appear to negatively affect activity. Enzymatic activities are shown for enzyme variants Kuma030, Kuma031, Kuma032, Kuma040, Kuma041, and Kuma042 on the immunogenic gliadin epitope DQ2.5-glia-α1a. Samples were taken at the indicated timepoints, and the concentration of peptide breakdown product PFPQPQ (SEQ ID NO: 148) was measured. Activities are graphed as the ratio of the appropriate m/z signal to that of the internal standard. All enzymes were purified by anion exchange.

Since KumaXX1 and KumaXX2 variants lack a His tag, they are not purified by Ni affinity chromatography. Instead, these variants are purified by anion exchange chromatography. The following graph demonstrates activity of variants Kuma030, Kuma031, Kuma032, Kuma040, Kuma041, and Kuma042 on immunogenic gliadin peptide DQ2.5-glia-α1a. In this case, all proteins were purified by anion exchange chromatography (even Kuma030 and Kuma040 which harbor an intact 6× Histidine tag), for the sake of comparison. As shown in FIG. 7, P171R and H172R mutations do not appear to negatively affect activity as Kuma032 and Kuma042 demonstrate comparable activity as Kuma030 and Kuma040 (Kuma042 even shows a slight increase in activity against this substrate compared to Kuma040).

Figure 8:
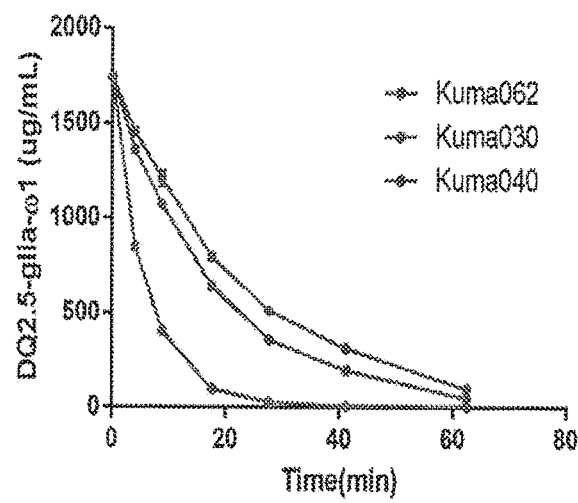
FIG. 8. Kuma062 demonstrates a higher level of enzymatic activity than Kuma030 or Kuma040. Shown is activity on the immunogenic gliadin epitope DQ2.5-glia-ω1.
Figure 8:
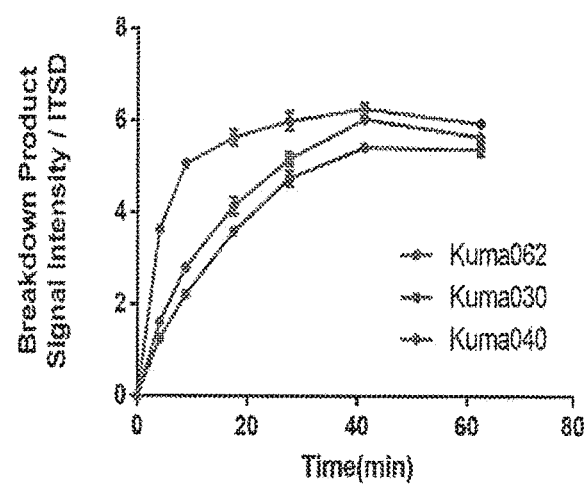

Kuma010 variant Kuma062 demonstrates a high amount of activity and it lacks a His tag. A comparison of Kuma062 with Kuma030 and Kuma040 is shown in FIGS. 8A-B (left, detection of full-length DQ2.5-glia-ω1; right, detection of breakdown product):

Enzyme Kinetics

Biochemical parameters were estimated for: Kuma010, Kuma030, Kuma040, and Kuma050. These were estimated using immunogenic gliadin epitopes DQ2.5-glia-α1a and DQ2.5-glia-ω1. Degradation assays were performed with 100 nM enzyme at 37° C. in 100 mM NaOAc pH 4.0 buffer. The below table shows the initial velocity of the degradation reaction as a function of substrate concentration. $k_{cat}$ and $K_M$ were calculated from this using the Michaelis-Menten equation.

The biochemical parameters of all tested enzymes are shown in Table 7 below.

TABLE 7

| Enzyme | [Enzyme] | Substrate | Vmax (M s$^{-1}$) | Km (mM) | Kcat (s$^{-1}$) | kcat/Km (M$^{-1}$ s$^{-1}$) |
|---|---|---|---|---|---|---|
| Kuma010 | 100 nM | Glia_α1 | 3.70E−07 | 4 6 mM | 3.7 | 819 |
| Kuma030 | 100 nM | Glia_α1 | 1.74E−06 | 1.9 mM | 17.4 | 9034 |
| Kuma040 | 100 nM | Glia_α1 | 1.49E−06 | 0.86 mM | 16.3 | 19109 |
| Kuma050 | 100 nM | Glia_α1 | 1.42E−06 | 2.5 mM | 14.2 | 5613 |
| Kuma010 | 100 nM | Glia_α1 | 1.22E−07 | 16.4 mM | 1.2 | 74 |
| Kuma030 | 100 nM | Glia_α1 | 2.73E−06 | 8.4 mM | 27.3 | 3268 |
| Kuma040 | 100 nM | Glia_α1 | 2.46E−06 | 15.3 mM | 24.6 | 1603 |
| Kuma050 | 100 nM | Glia_α1 | 2.78E−06 | 5.0 mM | 27.8 | 56 |

The mutations made to Kuma030 and Kuma040 greatly increase activity against these peptides, which is promising for their use in detoxifying peptides that are linked to celiac disease. As predicted, the mutations made to Kuma050 increased activity on the DQ2.5-glia-α1a peptide, but not on the DQ2.5-glia-ω1 peptide.

REFERENCES FOR EXAMPLE 2

(1) Gordon, S. R.; Stanley, E. J.; Wolf, S.; Toland, A.; Wu, S. J.; Hadidi, D.; Mills, J. H.; Baker, D.; Pultz, I. S.; Siegel, J. B. *Journal of the American Chemical Society* 2012.

(2) Wlodawer, A.; Li, M.; Gustchina, A.; Tsuruoka, N.; Ashida, M.; Minakata, H.; Oyama, H.; Oda, K.; Nishino, T.; Nakayama, T. *J Biol Chem* 2004, 279, 21500.

(3) Leaver-Fay, A.; Tyka, M.; Lewis, S. M.; Lange, O. F.; Thompson, J.; Jacak, R.; Kaufman, K.; Renfrew, P. D.; Smith, C. A.; Sheffler, W.; Davis, I. W.; Cooper, S.; Treuille, A.; Mandell, D. J.; Richter, F.; Ban, Y. E.; Fleishman, S. J.; Corn, J. E.; Kim, D. E.; Lyskov, S.; Berrondo, M.; Mentzer, S.; Popovic, Z.; Havranek, J. J.; Karanicolas, J.; Das, R.; Meiler, J.; Kortemme, T.; Gray, J. J.; Kuhlman, B.; Baker, D.; Bradley, P. *Methods Enzymol* 2011, 487, 545.

(4) Wolf, C.; Siegel, J. B.; Tinberg, C.; Camarca, A.; Gianfrani, C.; Paski, S.; Guan, R.; Monteleone, G.; Baker, D.; Pultz, I. S. *Journal of the American Chemical Society* 2015, 137, 13106.

(5) Shan, L.; Molberg, O.; Parrot, I.; Hausch, F.; Filiz, F.; Gray, G. M.; Sollid, L. M.; Khosla, C. *Science* 2002, 297, 2275.

(6) Shan, L. *Journal of Proteome Research* 2005.

(7) Sollid, L. M.; Qiao, S. W.; Anderson, R. P.; Gianfrani, C.; Koning, F. *Immunogenetics* 2012, 64, 455.

(8) Arentz-Hansen, H.; Korner, R.; Molberg, O.; Quarsten, H.; Vader, W.; Kooy, Y. M.; Lundin, K. E.; Koning, F.; Roepstorff, P.; Sollid, L. M.; McAdam, S. N. *J Exp Med* 2000, 191, 603.

We claim:

1. A polypeptide comprising the amino acid sequence set forth in SEQ ID NO:129.

2. A pharmaceutical composition, comprising the polypeptide of claim 1, and a pharmaceutically acceptable carrier.

* * * * *

SEQUENCE LISTING

<160> NUMBER OF SEQ ID NOS: 156

<210> SEQ ID NO 1
<211> LENGTH: 553
<212> TYPE: PRT
<213> ORGANISM: Artificial Sequence
<220> FEATURE:
<223> OTHER INFORMATION: Synthetic

<400> SEQUENCE: 1

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
                100                 105                 110

Ala Val Leu Ser Gly Pro Asp Asp Ala Ile Asn Arg Ala Phe Gly Val
            115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
    195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
    275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
```

-continued

```
                355                 360                 365
Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Gly Val Ser Arg Ile Phe Pro Leu
                405                 410                 415

Pro Ala Trp Gln Glu His Ala Asn Val Pro Ser Ala Asn Pro Gly
                420                 425                 430

Ala Ser Ser Gly Arg Gly Val Pro Asp Leu Ala Gly Asn Ala Asp Pro
                435                 440                 445

Ala Thr Gly Tyr Glu Val Val Ile Asp Gly Glu Ala Thr Val Ile Gly
                450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
                515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro
545                 550

<210> SEQ ID NO 2
<211> LENGTH: 553
<212> TYPE: PRT
<213> ORGANISM: Artificial Sequence
<220> FEATURE:
<223> OTHER INFORMATION: Synthetic

<400> SEQUENCE: 2

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
                35                  40                  45

Arg Gln Arg Ala Gly Glu Leu Ala Ala His Val Glu Arg Gln Ala Ala
50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
                100                 105                 110

Ala Val Leu Ser Gly Pro Asp Ala Ile Asn Arg Ala Phe Gly Val
                115                 120                 125

Glu Leu Arg His Phe Asp His Pro Asp Gly Ser Tyr Arg Ser Tyr Leu
                130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
```

```
            165                 170                 175
Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
            210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
            245                 250                 255

Pro Thr Gly Asp Pro Glu Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
            290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
            325                 330                 335

Phe Leu Asp Ala Ala Leu Gly Val Thr Val Leu Ala Ala Ala Ala Gly
            340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
            370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
            530                 535                 540

Leu Pro Ser Ala Ser Gln Pro Gln Pro
545                 550

<210> SEQ ID NO 3
<211> LENGTH: 553
<212> TYPE: PRT
<213> ORGANISM: Artificial Sequence
```

<220> FEATURE:
<223> OTHER INFORMATION: Synthetic

<400> SEQUENCE: 3

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Ala Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

```
Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
        420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
        500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro
545                 550
```

<210> SEQ ID NO 4
<211> LENGTH: 553
<212> TYPE: PRT
<213> ORGANISM: Artificial Sequence
<220> FEATURE:
<223> OTHER INFORMATION: Synthetic

<400> SEQUENCE: 4

```
Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
            85                  90                  95

Asp Ala His Gly Leu Ala Leu Asp Arg Ala Asn Val Ala Ala Gly Thr
        100                 105                 110

Ala Val Leu Ser Gly Pro Asp Asp Ala Ile Asn Arg Ala Phe Gly Val
    115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
            165                 170                 175

Arg Arg Ala Glu Gly Gly Phe Glu Ala Arg Ser Gln Ala Ala Ala Pro
        180                 185                 190

Thr Ala Tyr Thr Pro Leu Asp Val Ala Gln Ala Tyr Gln Phe Pro Glu
    195                 200                 205
```

Gly Leu Asp Gly Gln Gly Gln Cys Ile Ala Ile Ile Glu Leu Gly Gly
        210                 215                 220

Gly Tyr Asp Glu Ala Ser Leu Ala Gln Tyr Phe Ala Ser Leu Gly Val
225                 230                 235                 240

Pro Ala Pro Gln Val Ser Val Ser Val Asp Gly Ala Ser Asn Gln
            245                 250                 255

Pro Thr Gly Asp Pro Lys Gly Pro Asp Gly Glu Ser Glu Leu Asp Ile
        260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
        290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
                340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro
545                 550

<210> SEQ ID NO 5
<211> LENGTH: 553
<212> TYPE: PRT
<213> ORGANISM: Artificial Sequence
<220> FEATURE:
<223> OTHER INFORMATION: Synthetic

<400> SEQUENCE: 5

Met Ser Asp Met Glu Lys Pro Trp Lys Glu Gly Glu Glu Ala Arg Ala
1               5                   10                  15

-continued

```
Val Leu Gln Gly His Ala Arg Ala Gln Ala Pro Gln Ala Val Asp Lys
         20                  25                  30

Gly Pro Val Ala Gly Asp Glu Arg Met Ala Val Thr Val Leu Arg
             35                  40                  45

Arg Gln Arg Ala Gly Glu Leu Ala Ala His Val Glu Arg Gln Ala Ala
 50                  55                  60

Ile Ala Pro His Ala Arg Glu His Leu Lys Arg Glu Ala Phe Ala Ala
 65                  70                  75                  80

Ser His Gly Ala Ser Leu Asp Asp Phe Ala Glu Leu Arg Arg Phe Ala
                 85                  90                  95

Asp Ala His Gly Leu Ala Leu Asp Arg Ala Asn Val Ala Gly Thr
             100                 105                 110

Ala Val Leu Ser Gly Pro Asp Asp Ala Ile Asn Arg Ala Phe Gly Val
         115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                 165                 170                 175

Arg Arg Ala Glu Gly Gly Phe Glu Ala Arg Ser Gln Ala Ala Ala Pro
             180                 185                 190

Thr Ala Tyr Thr Pro Leu Asp Val Ala Gln Ala Tyr Gln Phe Pro Glu
         195                 200                 205

Gly Leu Asp Gly Gln Gly Gln Cys Ile Ala Ile Ile Glu Leu Gly Gly
         210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                 245                 250                 255

Pro Thr Gly Asp Pro Lys Gly Pro Asp Gly Glu Thr Glu Leu Asp Ile
             260                 265                 270

Glu Val Ala Gly Ala Leu Ala Pro Gly Ala Lys Phe Ala Val Tyr Phe
         275                 280                 285

Ala Pro Asp Thr Thr Ala Gly Phe Leu Asp Ala Ile Thr Thr Ala Ile
         290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                 325                 330                 335

Phe Leu Asp Ala Ala Leu Gly Val Thr Val Leu Ala Ala Ala Gly
             340                 345                 350

Asp Ser Gly Ser Thr Gly Gly Glu Gln Asp Gly Leu Tyr His Val His
         355                 360                 365

Phe Pro Ala Ala Ser Pro Tyr Val Leu Ala Cys Gly Gly Thr Arg Leu
     370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                 405                 410                 415

Pro Ala Trp Gln Glu His Ala Asn Val Pro Ser Ala Asn Pro Gly
             420                 425                 430
```

```
Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
530                 535                 540

Leu Pro Ser Ala Ser Gln Pro Gln
545                 550

<210> SEQ ID NO 6
<211> LENGTH: 553
<212> TYPE: PRT
<213> ORGANISM: Artificial Sequence
<220> FEATURE:
<223> OTHER INFORMATION: Synthetic

<400> SEQUENCE: 6

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240
```

```
Pro Ala Pro Gln Val Val Ser Val Ser Val Asp Gly Ala Ser Asn Gln
            245                 250                 255

Pro Thr Gly Asp Pro Lys Gly Pro Asp Gly Glu Val Leu Leu Asp Ile
        260                 265                 270

Glu Val Ala Gly Ala Leu Ala Pro Gly Ala Lys Phe Ala Val Tyr Phe
    275                 280                 285

Ala Pro Asp Thr Thr Ala Gly Phe Leu Asp Ala Ile Thr Thr Ala Ile
290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
            325                 330                 335

Phe Leu Asp Ala Ala Leu Gly Val Thr Val Leu Ala Ala Ala Ala Gly
        340                 345                 350

Asp Ser Gly Ser Thr Gly Gly Glu Gln Asp Gly Leu Tyr His Val His
    355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Ser Ala Asn Pro Gly
        420                 425                 430

Ala Ser Ser Gly Arg Gly Val Pro Asp Leu Ala Gly Asn Ala Asp Pro
    435                 440                 445

Ala Thr Gly Tyr Glu Val Val Ile Asp Gly Glu Ala Thr Val Ile Gly
450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
        500                 505                 510

Ile Ala Asn Arg Ala Gln Ile Tyr Gln Ala Gly Pro Gly Trp Asp Pro
    515                 520                 525

Cys Thr Gly Leu Gly Ser Pro Ile Gly Val Arg Leu Leu Gln Ala Leu
530                 535                 540

Leu Pro Ser Ala Ser Gln Pro Gln
545                 550

<210> SEQ ID NO 7
<211> LENGTH: 553
<212> TYPE: PRT
<213> ORGANISM: Artificial Sequence
<220> FEATURE:
<223> OTHER INFORMATION: Synthetic

<400> SEQUENCE: 7

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45
```

```
Arg Gln Arg Ala Gly Glu Leu Ala Ala His Val Glu Arg Gln Ala Ala
 50                  55                  60

Ile Ala Pro His Ala Arg Glu His Leu Lys Arg Glu Ala Phe Ala Ala
 65                  70                  75                  80

Ser His Gly Ala Ser Leu Asp Asp Phe Ala Glu Leu Arg Arg Phe Ala
                 85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
            115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Thr Leu Asp Ile
            260                 265                 270

Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Ala Gly
            340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
450                 455                 460

Gly Thr Ser Ala Val Ala Pro Leu Phe Ala Ala Leu Val Ala Arg Ile
```

```
465                 470                 475                 480
Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
                515                 520                 525

Cys Thr Gly Leu Gly Ser Pro Ile Gly Val Arg Leu Leu Gln Ala Leu
                530                 535                 540

Leu Pro Ser Ala Ser Gln Pro Gln Pro
545                 550

<210> SEQ ID NO 8
<211> LENGTH: 553
<212> TYPE: PRT
<213> ORGANISM: Artificial Sequence
<220> FEATURE:
<223> OTHER INFORMATION: Synthetic

<400> SEQUENCE: 8

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
                35                  40                  45

Arg Gln Arg Ala Gly Glu Leu Ala Ala His Val Glu Arg Gln Ala Ala
50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
                100                 105                 110

Ala Val Leu Ser Gly Pro Asp Asp Ala Ile Asn Arg Ala Phe Gly Val
                115                 120                 125

Glu Leu Arg His Phe Asp His Pro Asp Gly Ser Tyr Arg Ser Tyr Leu
                130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
                180                 185                 190

Thr Ala Tyr Thr Pro Leu Asp Val Ala Gln Ala Tyr Gln Phe Pro Glu
                195                 200                 205

Gly Leu Asp Gly Gln Gly Gln Cys Ile Ala Ile Ile Glu Leu Gly Gly
                210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Ala Asp Ile
                260                 265                 270

Glu Val Ala Gly Ala Leu Ala Pro Gly Ala Lys Phe Ala Val Tyr Phe
```

```
            275                 280                 285
Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro
545                 550
```

<210> SEQ ID NO 9
<211> LENGTH: 553
<212> TYPE: PRT
<213> ORGANISM: Artificial Sequence
<220> FEATURE:
<223> OTHER INFORMATION: Synthetic

<400> SEQUENCE: 9

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
```

-continued

```
                    85                  90                  95
Asp Ala His Gly Leu Ala Leu Asp Arg Ala Asn Val Ala Ala Gly Thr
                100                 105                 110
Ala Val Leu Ser Gly Pro Asp Ala Ile Asn Arg Ala Phe Gly Val
                115                 120                 125
Glu Leu Arg His Phe Asp His Pro Asp Gly Ser Tyr Arg Ser Tyr Leu
            130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                165                 170                 175
Arg Arg Ala Glu Gly Gly Phe Glu Ala Arg Ser Gln Ala Ala Ala Pro
                180                 185                 190
Thr Ala Tyr Thr Pro Leu Asp Val Ala Gln Ala Tyr Gln Phe Pro Glu
                195                 200                 205
Gly Leu Asp Gly Gln Gly Gln Cys Ile Ala Ile Ile Glu Leu Gly Gly
            210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Lys Gly Pro Asp Gly Glu Val Thr Asp Ile
                260                 265                 270
Glu Val Ala Gly Ala Leu Ala Pro Gly Ala Lys Phe Ala Val Tyr Phe
            275                 280                 285
Ala Pro Asp Thr Thr Ala Gly Phe Leu Asp Ala Ile Thr Thr Ala Ile
290                 295                 300
His Asp Pro Thr Leu Lys Pro Ser Val Val Ser Ile Ser Trp Ser Gly
305                 310                 315                 320
Pro Glu Asp Ser Trp Thr Ser Ala Ala Ile Ala Ala Met Asn Arg Ala
                325                 330                 335
Phe Leu Asp Ala Ala Ala Leu Gly Val Thr Val Leu Ala Ala Ala Gly
            340                 345                 350
Asp Ser Gly Ser Thr Gly Gly Glu Gln Asp Gly Leu Tyr His Val His
            355                 360                 365
Phe Pro Ala Ala Ser Pro Tyr Val Leu Ala Cys Gly Gly Thr Arg Leu
            370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Ser Ala Asn Pro Gly
                420                 425                 430
Ala Ser Ser Gly Arg Gly Val Pro Asp Leu Ala Gly Asn Ala Asp Pro
            435                 440                 445
Ala Thr Gly Tyr Glu Val Val Ile Asp Gly Glu Ala Thr Val Ile Gly
            450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
            485                 490                 495
Gln Leu Pro Ala Asp Val Phe His Asp Ile Thr Glu Gly Asn Asn Asp
            500                 505                 510
```

```
Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
        530                 535                 540

Leu Pro Ser Ala Ser Gln Pro Gln Pro
545                 550

<210> SEQ ID NO 10
<211> LENGTH: 553
<212> TYPE: PRT
<213> ORGANISM: Artificial Sequence
<220> FEATURE:
<223> OTHER INFORMATION: Synthetic

<400> SEQUENCE: 10

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Val Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320
```

Pro Glu Asp Ser Trp Thr Ser Ala Ala Ile Ala Ala Met Asn Arg Ala
            325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
            370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
            530                 535                 540

Leu Pro Ser Ala Ser Gln Pro Gln Pro
545                 550

<210> SEQ ID NO 11
<211> LENGTH: 553
<212> TYPE: PRT
<213> ORGANISM: Artificial Sequence
<220> FEATURE:
<223> OTHER INFORMATION: Synthetic

<400> SEQUENCE: 11

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65              70                  75                  80

Ser His Gly Ala Ser Leu Asp Asp Phe Ala Glu Leu Arg Arg Phe Ala
            85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
            115                 120                 125

```
Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
            165                 170                 175

Arg Arg Ala Glu Gly Gly Phe Glu Ala Arg Ser Gln Ala Ala Ala Pro
        180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
290                 295                 300

His Asp Pro Thr Leu Lys Pro Ser Val Val Ser Ile Ser Trp Ala Gly
305                 310                 315                 320

Pro Glu Asp Ser Trp Thr Ser Ala Ala Ile Ala Ala Met Asn Arg Ala
            325                 330                 335

Phe Leu Asp Ala Ala Leu Gly Val Thr Val Leu Ala Ala Ala Gly
        340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
530                 535                 540
```

Leu Pro Ser Ala Ser Gln Pro Gln Pro
545                 550

<210> SEQ ID NO 12
<211> LENGTH: 553
<212> TYPE: PRT
<213> ORGANISM: Artificial Sequence
<220> FEATURE:
<223> OTHER INFORMATION: Synthetic

<400> SEQUENCE: 12

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
        290                 295                 300

His Asp Pro Thr Leu Lys Pro Ser Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

```
Asp Ala Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
        500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
        530                 535                 540

Leu Pro Ser Ala Ser Gln Pro Gln Pro
545                 550

<210> SEQ ID NO 13
<211> LENGTH: 553
<212> TYPE: PRT
<213> ORGANISM: Artificial Sequence
<220> FEATURE:
<223> OTHER INFORMATION: Synthetic

<400> SEQUENCE: 13

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
            85                  90                  95

Asp Ala His Gly Leu Ala Leu Asp Arg Ala Asn Val Ala Ala Gly Thr
        100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
        130                 135                 140

Gly Glu Val Thr Val Pro Ala Ser Ile Ala Pro Met Ile Glu Ala Val
145                 150                 155                 160
```

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Ala Gly
            340                 345                 350

Asp Glu Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro
545                 550

<210> SEQ ID NO 14
<211> LENGTH: 553
<212> TYPE: PRT

<213> ORGANISM: Artificial Sequence
<220> FEATURE:
<223> OTHER INFORMATION: Synthetic

<400> SEQUENCE: 14

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
                35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
                100                 105                 110

Ala Val Leu Ser Gly Pro Asp Asp Ala Ile Asn Arg Ala Phe Gly Val
                115                 120                 125

Glu Leu Arg His Phe Asp His Pro Asp Gly Ser Tyr Arg Ser Tyr Leu
                130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
                180                 185                 190

Thr Ala Tyr Thr Pro Leu Asp Val Ala Gln Ala Tyr Gln Phe Pro Glu
                195                 200                 205

Gly Leu Asp Gly Gln Gly Gln Cys Ile Ala Ile Glu Leu Gly Gly
                210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
                260                 265                 270

Glu Val Ala Gly Ala Leu Ala Pro Gly Ala Lys Phe Ala Val Tyr Phe
                275                 280                 285

Ala Pro Asp Thr Thr Ala Gly Phe Leu Asp Ala Ile Thr Thr Ala Ile
                290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
                340                 345                 350

Asp Gln Gly Ser Thr Gly Gly Glu Gln Asp Gly Leu Tyr His Val His
                355                 360                 365

Phe Pro Ala Ala Ser Pro Tyr Val Leu Ala Cys Gly Gly Thr Arg Leu
                370                 375                 380

Val Ala Ser Gly Gly Arg Ile Ala Gln Glu Thr Val Trp Asn Asp Gly
```

```
            385                 390                 395                 400
    Pro Asp Gly Gly Ala Thr Gly Gly Val Ser Arg Ile Phe Pro Leu
                    405                 410                 415

Pro Ala Trp Gln Glu His Ala Asn Val Pro Ser Ala Asn Pro Gly
                    420                 425                 430

Ala Ser Ser Gly Arg Gly Val Pro Asp Leu Ala Gly Asn Ala Asp Pro
                    435                 440                 445

Ala Thr Gly Tyr Glu Val Val Ile Asp Gly Glu Ala Thr Val Ile Gly
                    450                 455                 460

Gly Thr Ser Ala Val Ala Pro Leu Phe Ala Ala Leu Val Ala Arg Ile
    465                 470                 475                 480

Asn Gln Lys Leu Gly Lys Ala Val Gly Tyr Leu Asn Pro Thr Leu Tyr
                    485                 490                 495

Gln Leu Pro Ala Asp Val Phe His Asp Ile Thr Glu Gly Asn Asn Asp
                    500                 505                 510

Ile Ala Asn Arg Ala Gln Ile Tyr Gln Ala Gly Pro Gly Trp Asp Pro
                    515                 520                 525

Cys Thr Gly Leu Gly Ser Pro Ile Gly Val Arg Leu Leu Gln Ala Leu
                    530                 535                 540

Leu Pro Ser Ala Ser Gln Pro Gln Pro
    545                 550

<210> SEQ ID NO 15
<211> LENGTH: 553
<212> TYPE: PRT
<213> ORGANISM: Artificial Sequence
<220> FEATURE:
<223> OTHER INFORMATION: Synthetic

<400> SEQUENCE: 15

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
```

```
                195                 200                 205
Gly Leu Asp Gly Gln Gly Gln Cys Ile Ala Ile Ile Glu Leu Gly Gly
    210                 215                 220
Gly Tyr Asp Glu Ala Ser Leu Ala Gln Tyr Phe Ala Ser Leu Gly Val
225                 230                 235                 240
Pro Ala Pro Gln Val Ser Val Ser Val Asp Gly Ala Ser Asn Gln
                245                 250                 255
Pro Thr Gly Asp Pro Lys Gly Pro Asp Gly Glu Val Glu Leu Asp Ile
            260                 265                 270
Glu Val Ala Gly Ala Leu Ala Pro Gly Ala Lys Phe Ala Val Tyr Phe
            275                 280                 285
Ala Pro Asp Thr Thr Ala Gly Phe Leu Asp Ala Ile Thr Thr Ala Ile
        290                 295                 300
His Asp Pro Thr Leu Lys Pro Ser Val Val Ser Ile Ser Trp Ser Gly
305                 310                 315                 320
Pro Glu Asp Ser Trp Thr Ser Ala Ala Ile Ala Ala Met Asn Arg Ala
                325                 330                 335
Phe Leu Asp Ala Ala Ala Leu Gly Val Thr Val Leu Ala Ala Ala Gly
                340                 345                 350
Asp Arg Gly Ser Thr Gly Gly Glu Gln Asp Gly Leu Tyr His Val His
            355                 360                 365
Phe Pro Ala Ala Ser Pro Tyr Val Leu Ala Cys Gly Gly Thr Arg Leu
        370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Pro Ser Ala Asn Pro Gly
                420                 425                 430
Ala Ser Ser Gly Arg Gly Val Pro Asp Leu Ala Gly Asn Ala Asp Pro
            435                 440                 445
Ala Thr Gly Tyr Glu Val Val Ile Asp Gly Glu Ala Thr Val Ile Gly
        450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
                485                 490                 495
Gln Leu Pro Ala Asp Val Phe His Asp Ile Thr Glu Gly Asn Asn Asp
            500                 505                 510
Ile Ala Asn Arg Ala Gln Ile Tyr Gln Ala Gly Pro Gly Trp Asp Pro
        515                 520                 525
Cys Thr Gly Leu Gly Ser Pro Ile Gly Val Arg Leu Leu Gln Ala Leu
    530                 535                 540
Leu Pro Ser Ala Ser Gln Pro Gln
545                 550

<210> SEQ ID NO 16
<211> LENGTH: 553
<212> TYPE: PRT
<213> ORGANISM: Artificial Sequence
<220> FEATURE:
<223> OTHER INFORMATION: Synthetic

<400> SEQUENCE: 16

Met Ser Asp Met Glu Lys Pro Trp Lys Glu Gly Glu Glu Ala Arg Ala
```

-continued

```
1               5                   10                  15
Val Leu Gln Gly His Ala Arg Ala Gln Ala Pro Gln Ala Val Asp Lys
                20                  25                  30
Gly Pro Val Ala Gly Asp Glu Arg Met Ala Val Thr Val Val Leu Arg
                35                  40                  45
Arg Gln Arg Ala Gly Glu Leu Ala Ala His Val Glu Arg Gln Ala Ala
            50                  55                  60
Ile Ala Pro His Ala Arg Glu His Leu Lys Arg Glu Ala Phe Ala Ala
65                  70                  75                  80
Ser His Gly Ala Ser Leu Asp Asp Phe Ala Glu Leu Arg Arg Phe Ala
                85                  90                  95
Asp Ala His Gly Leu Ala Leu Asp Arg Ala Asn Val Ala Ala Gly Thr
                100                 105                 110
Ala Val Leu Ser Gly Pro Asp Asp Ala Ile Asn Arg Ala Phe Gly Val
                115                 120                 125
Glu Leu Arg His Phe Asp His Pro Asp Gly Ser Tyr Arg Ser Tyr Leu
                130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                165                 170                 175
Arg Arg Ala Glu Gly Gly Phe Glu Ala Arg Ser Gln Ala Ala Ala Pro
                180                 185                 190
Thr Ala Tyr Thr Pro Leu Asp Val Ala Gln Ala Tyr Gln Phe Pro Glu
                195                 200                 205
Gly Leu Asp Gly Gln Gly Gln Cys Ile Ala Ile Ile Glu Leu Gly Gly
                210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Lys Gly Pro Asp Gly Glu Val Glu Leu Asp Ile
                260                 265                 270
Glu Val Ala Gly Ala Leu Ala Pro Gly Ala Lys Phe Ala Val Tyr Phe
                275                 280                 285
Ala Pro Asp Thr Thr Ala Gly Phe Leu Asp Ala Ile Thr Thr Ala Ile
                290                 295                 300
His Asp Pro Thr Leu Lys Pro Ser Val Val Ser Ile Ser Trp Ser Gly
305                 310                 315                 320
Pro Glu Asp Ser Trp Thr Ser Ala Ala Ile Ala Ala Met Asn Arg Ala
                325                 330                 335
Phe Leu Asp Ala Ala Leu Gly Val Thr Val Leu Ala Ala Ala Gly
                340                 345                 350
Asp Tyr Gly Ser Thr Gly Gly Glu Gln Asp Gly Leu Tyr His Val His
                355                 360                 365
Phe Pro Ala Ala Ser Pro Tyr Val Leu Ala Cys Gly Gly Thr Arg Leu
                370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Ser Ala Asn Pro Gly
                420                 425                 430
```

```
Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro
545                 550

<210> SEQ ID NO 17
<211> LENGTH: 553
<212> TYPE: PRT
<213> ORGANISM: Artificial Sequence
<220> FEATURE:
<223> OTHER INFORMATION: Synthetic

<400> SEQUENCE: 17

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240
```

```
Pro Ala Pro Gln Val Ser Val Ser Val Asp Gly Ala Ser Asn Gln
            245                 250                 255

Pro Thr Gly Asp Pro Lys Gly Pro Asp Gly Glu Val Glu Leu Asp Ile
        260                 265                 270

Glu Val Ala Gly Ala Leu Ala Pro Gly Ala Lys Phe Val Tyr Phe
            275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
            340                 345                 350

Asp Ser Gly Ser Thr Asn Gly Glu Gln Asp Gly Leu Tyr His Val His
            355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro
545                 550
```

<210> SEQ ID NO 18
<211> LENGTH: 553
<212> TYPE: PRT
<213> ORGANISM: Artificial Sequence
<220> FEATURE:
<223> OTHER INFORMATION: Synthetic

<400> SEQUENCE: 18

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
            35                  40                  45
```

```
Arg Gln Arg Ala Gly Glu Leu Ala Ala His Val Glu Arg Gln Ala Ala
     50                  55                  60

Ile Ala Pro His Ala Arg Glu His Leu Lys Arg Glu Ala Phe Ala Ala
65                   70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
                100                 105                 110

Ala Val Leu Ser Gly Pro Asp Asp Ala Ile Asn Arg Ala Phe Gly Val
            115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
                180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Gly Leu Asp Ile
                260                 265                 270

Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
                340                 345                 350

Asp Ser Gly Ser Thr Ser Gly Glu Gln Asp Gly Leu Tyr His Val His
            355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
    450                 455                 460
```

```
Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
        500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
        530                 535                 540

Leu Pro Ser Ala Ser Gln Pro Gln Pro
545                 550
```

<210> SEQ ID NO 19
<211> LENGTH: 553
<212> TYPE: PRT
<213> ORGANISM: Artificial Sequence
<220> FEATURE:
<223> OTHER INFORMATION: Synthetic

<400> SEQUENCE: 19

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Gly Leu Asp Ile
            260                 265                 270
```

```
Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
        290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Ala Gly
                340                 345                 350

Asp Ser Gly Ser Thr Gln Gly Glu Gln Asp Gly Leu Tyr His Val His
            355                 360                 365

Phe Pro Ala Ala Ser Pro Tyr Val Leu Ala Cys Gly Gly Thr Arg Leu
        370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro
545                 550

<210> SEQ ID NO 20
<211> LENGTH: 553
<212> TYPE: PRT
<213> ORGANISM: Artificial Sequence
<220> FEATURE:
<223> OTHER INFORMATION: Synthetic

<400> SEQUENCE: 20

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80
```

```
Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Phe Glu Ala Arg Ser Gln Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
            340                 345                 350

Asp Ser Gly Ser Thr Thr Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
```

```
                    500                 505                 510
Ile Ala Asn Arg Ala Gln Ile Tyr Gln Ala Gly Pro Gly Trp Asp Pro
                515                 520                 525

Cys Thr Gly Leu Gly Ser Pro Ile Gly Val Arg Leu Leu Gln Ala Leu
                530                 535                 540

Leu Pro Ser Ala Ser Gln Pro Gln Pro
545                 550

<210> SEQ ID NO 21
<211> LENGTH: 553
<212> TYPE: PRT
<213> ORGANISM: Artificial Sequence
<220> FEATURE:
<223> OTHER INFORMATION: Synthetic

<400> SEQUENCE: 21

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Ala Ile Asn Arg Ala Phe Gly Val
        115                 120                 125

Glu Leu Arg His Phe Asp His Pro Asp Gly Ser Tyr Arg Ser Tyr Leu
        130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
```

```
            305                 310                 315                 320
Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
                340                 345                 350

Asp Ser Gly Ser Thr Gly Gly Glu Gln Asp Gly Leu Tyr His Val Phe
                355                 360                 365

Phe Pro Ala Ala Ser Pro Tyr Val Leu Ala Cys Gly Gly Thr Arg Leu
                370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
                435                 440                 445

Ala Thr Gly Tyr Glu Val Val Ile Asp Gly Glu Ala Thr Val Ile Gly
                450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
                515                 520                 525

Cys Thr Gly Leu Gly Ser Pro Ile Gly Val Arg Leu Leu Gln Ala Leu
                530                 535                 540

Leu Pro Ser Ala Ser Gln Pro Gln Pro
545                 550

<210> SEQ ID NO 22
<211> LENGTH: 553
<212> TYPE: PRT
<213> ORGANISM: Artificial Sequence
<220> FEATURE:
<223> OTHER INFORMATION: Synthetic

<400> SEQUENCE: 22

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
                35                  40                  45

Arg Gln Arg Ala Gly Glu Leu Ala Ala His Val Glu Arg Gln Ala Ala
                50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
                100                 105                 110

Ala Val Leu Ser Gly Pro Asp Asp Ala Ile Asn Arg Ala Phe Gly Val
```

-continued

```
            115                 120                 125
Glu Leu Arg His Phe Asp His Pro Asp Gly Ser Tyr Arg Ser Tyr Leu
            130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                    165                 170                 175
Arg Arg Ala Glu Gly Gly Phe Glu Ala Arg Ser Gln Ala Ala Ala Pro
                    180                 185                 190
Thr Ala Tyr Thr Pro Leu Asp Val Ala Gln Ala Tyr Gln Phe Pro Glu
                    195                 200                 205
Gly Leu Asp Gly Gln Gly Gln Cys Ile Ala Ile Ile Glu Leu Gly Gly
            210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                    245                 250                 255
Pro Thr Gly Asp Pro Lys Gly Pro Asp Gly Glu Val Glu Leu Asp Ile
                    260                 265                 270
Glu Val Ala Gly Ala Leu Ala Pro Gly Ala Lys Phe Ala Val Tyr Phe
            275                 280                 285
Ala Pro Asp Thr Thr Ala Gly Phe Leu Asp Ala Ile Thr Thr Ala Ile
290                 295                 300
His Asp Pro Thr Leu Lys Pro Ser Val Val Ser Ile Ser Trp Ser Gly
305                 310                 315                 320
Pro Glu Asp Ser Trp Thr Ser Ala Ala Ile Ala Ala Met Asn Arg Ala
                    325                 330                 335
Phe Leu Asp Ala Ala Ala Leu Gly Val Thr Val Leu Ala Ala Ala Gly
                    340                 345                 350
Asp Ser Gly Ser Thr Gly Gly Glu Gln Asp Gly Leu Tyr His Val Gln
                    355                 360                 365
Phe Pro Ala Ala Ser Pro Tyr Val Leu Ala Cys Gly Gly Thr Arg Leu
            370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                    405                 410                 415
Pro Ala Trp Gln Glu His Ala Asn Val Pro Pro Ser Ala Asn Pro Gly
                    420                 425                 430
Ala Ser Ser Gly Arg Gly Val Pro Asp Leu Ala Gly Asn Ala Asp Pro
                    435                 440                 445
Ala Thr Gly Tyr Glu Val Val Ile Asp Gly Glu Thr Val Ile Gly
            450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
                    485                 490                 495
Gln Leu Pro Ala Asp Val Phe His Asp Ile Thr Glu Gly Asn Asn Asp
                    500                 505                 510
Ile Ala Asn Arg Ala Gln Ile Tyr Gln Ala Gly Pro Gly Trp Asp Pro
                    515                 520                 525
Cys Thr Gly Leu Gly Ser Pro Ile Gly Val Arg Leu Leu Gln Ala Leu
            530                 535                 540
```

Leu Pro Ser Ala Ser Gln Pro Gln Pro
545                 550

<210> SEQ ID NO 23
<211> LENGTH: 553
<212> TYPE: PRT
<213> ORGANISM: Artificial Sequence
<220> FEATURE:
<223> OTHER INFORMATION: Synthetic

<400> SEQUENCE: 23

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Gln Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
        530                 535                 540

Leu Pro Ser Ala Ser Gln Pro Gln Pro
545                 550

<210> SEQ ID NO 24
<211> LENGTH: 553
<212> TYPE: PRT
<213> ORGANISM: Artificial Sequence
<220> FEATURE:
<223> OTHER INFORMATION: Synthetic

<400> SEQUENCE: 24

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Gln Gly
385                 390                 395                 400

Pro Ser Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln
545                 550

<210> SEQ ID NO 25
<211> LENGTH: 553

<212> TYPE: PRT
<213> ORGANISM: Artificial Sequence
<220> FEATURE:
<223> OTHER INFORMATION: Synthetic

<400> SEQUENCE: 25

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
                35                  40                  45

Arg Gln Arg Ala Gly Glu Leu Ala Ala His Val Glu Arg Gln Ala Ala
50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
                100                 105                 110

Ala Val Leu Ser Gly Pro Asp Asp Ala Ile Asn Arg Ala Phe Gly Val
                115                 120                 125

Glu Leu Arg His Phe Asp His Pro Asp Gly Ser Tyr Arg Ser Tyr Leu
                130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
                180                 185                 190

Thr Ala Tyr Thr Pro Leu Asp Val Ala Gln Ala Tyr Gln Phe Pro Glu
                195                 200                 205

Gly Leu Asp Gly Gln Gly Gln Cys Ile Ala Ile Ile Glu Leu Gly Gly
                210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
                260                 265                 270

Glu Val Ala Gly Ala Leu Ala Pro Gly Ala Lys Phe Ala Val Tyr Phe
                275                 280                 285

Ala Pro Asp Thr Thr Ala Gly Phe Leu Asp Ala Ile Thr Thr Ala Ile
                290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
                340                 345                 350

Asp Ser Gly Ser Thr Gly Gly Glu Gln Asp Gly Leu Tyr His Val His
                355                 360                 365

Phe Pro Ala Ala Ser Pro Tyr Val Leu Ala Cys Gly Gly Thr Arg Leu
                370                 375                 380
```

Val Ala Ser Gly Gly Arg Ile Ala Gln Glu Thr Val Trp Asn Gln Gly
385                 390                 395                 400

Pro Gln Gly Gly Ala Thr Gly Gly Val Ser Arg Ile Phe Pro Leu
            405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro
545                 550

<210> SEQ ID NO 26
<211> LENGTH: 553
<212> TYPE: PRT
<213> ORGANISM: Artificial Sequence
<220> FEATURE:
<223> OTHER INFORMATION: Synthetic

<400> SEQUENCE: 26

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
            115                 120                 125

Glu Leu Arg His Phe Asp His Pro Asp Gly Ser Tyr Arg Ser Tyr Leu
            130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Gln Gly
385                 390                 395                 400

Pro Gln Gly Gly Ala Ser Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln
545                 550

<210> SEQ ID NO 27
<211> LENGTH: 553
<212> TYPE: PRT
<213> ORGANISM: Artificial Sequence
<220> FEATURE:
<223> OTHER INFORMATION: Synthetic

<400> SEQUENCE: 27

-continued

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
                35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Ala Ile Asn Arg Ala Phe Gly Val
            115                 120                 125

Glu Leu Arg His Phe Asp His Pro Asp Gly Ser Tyr Arg Ser Tyr Leu
        130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Gln Gly
385                 390                 395                 400

Pro Gln Gly Gly Ala Ser Gly Gly Gly Val Ser Arg Ile Phe Pro Leu
                405                 410                 415

Pro Ala Trp Gln Glu His Ala Asn Val Pro Pro Ser Ala Asn Pro Gly
```

```
                420             425             430
Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro
545                 550

<210> SEQ ID NO 28
<211> LENGTH: 553
<212> TYPE: PRT
<213> ORGANISM: Artificial Sequence
<220> FEATURE:
<223> OTHER INFORMATION: Synthetic

<400> SEQUENCE: 28

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
```

-continued

```
               225                 230                 235                 240
       Pro Ala Pro Gln Val Val Ser Val Ser Val Asp Gly Ala Ser Asn Gln
                           245                 250                 255
       Pro Thr Gly Asp Pro Lys Gly Pro Asp Gly Glu Val Glu Leu Asp Ile
                           260                 265                 270
       Glu Val Ala Gly Ala Leu Ala Pro Gly Ala Lys Phe Ala Val Tyr Phe
                           275                 280                 285
       Ala Pro Asp Thr Thr Ala Gly Phe Leu Asp Ala Ile Thr Thr Ala Ile
                           290                 295                 300
       His Asp Pro Thr Leu Lys Pro Ser Val Val Ser Ile Ser Trp Ser Gly
       305                 310                 315                 320
       Pro Glu Asp Ser Trp Thr Ser Ala Ala Ile Ala Ala Met Asn Arg Ala
                           325                 330                 335
       Phe Leu Asp Ala Ala Ala Leu Gly Val Thr Val Leu Ala Ala Ala Gly
                           340                 345                 350
       Asp Ser Gly Ser Thr Gly Gly Glu Gln Asp Gly Leu Tyr His Val His
                           355                 360                 365
       Phe Pro Ala Ala Ser Pro Tyr Val Leu Ala Cys Gly Gly Thr Arg Leu
                           370                 375                 380
       Val Ala Ser Gly Gly Arg Ile Ala Gln Glu Thr Val Trp Asn Asp Gly
       385                 390                 395                 400
       Pro Asp Gly Gly Ala Thr Gly Gly Val Ser Arg Ile Phe Pro Leu
                           405                 410                 415
       Pro Ala Trp Gln Glu His Ala Asn Val Pro Ser Ala Asn Pro Gly
                           420                 425                 430
       Ala Ser Ser Gly Arg Gly Val Pro Asp Leu Ala Gly Asn Ala Asp Pro
                           435                 440                 445
       Glu Thr Gly Tyr Glu Val Val Ile Asp Gly Glu Ala Thr Val Ile Gly
                           450                 455                 460
       Gly Thr Ser Ala Val Ala Pro Leu Phe Ala Ala Leu Val Ala Arg Ile
       465                 470                 475                 480
       Asn Gln Lys Leu Gly Lys Ala Val Gly Tyr Leu Asn Pro Thr Leu Tyr
                           485                 490                 495
       Gln Leu Pro Ala Asp Val Phe His Asp Ile Thr Glu Gly Asn Asn Asp
                           500                 505                 510
       Ile Ala Asn Arg Ala Gln Ile Tyr Gln Ala Gly Pro Gly Trp Asp Pro
                           515                 520                 525
       Cys Thr Gly Leu Gly Ser Pro Ile Gly Val Arg Leu Leu Gln Ala Leu
                           530                 535                 540
       Leu Pro Ser Ala Ser Gln Pro Gln
       545                 550

<210> SEQ ID NO 29
<211> LENGTH: 553
<212> TYPE: PRT
<213> ORGANISM: Artificial Sequence
<220> FEATURE:
<223> OTHER INFORMATION: Synthetic

<400> SEQUENCE: 29

Met Ser Asp Met Glu Lys Pro Trp Lys Glu Gly Glu Glu Ala Arg Ala
       1               5                   10                  15
       Val Leu Gln Gly His Ala Arg Ala Gln Ala Pro Gln Ala Val Asp Lys
                       20                  25                  30
       Gly Pro Val Ala Gly Asp Glu Arg Met Ala Val Thr Val Val Leu Arg
```

-continued

```
            35                  40                  45
Arg Gln Arg Ala Gly Glu Leu Ala Ala His Val Glu Arg Gln Ala Ala
 50                  55                  60
Ile Ala Pro His Ala Arg Glu His Leu Lys Arg Glu Ala Phe Ala Ala
 65                  70                  75                  80
Ser His Gly Ala Ser Leu Asp Asp Phe Ala Glu Leu Arg Arg Phe Ala
                     85                  90                  95
Asp Ala His Gly Leu Ala Leu Asp Arg Ala Asn Val Ala Ala Gly Thr
                100                 105                 110
Ala Val Leu Ser Gly Pro Asp Ala Ile Asn Arg Ala Phe Gly Val
                115                 120                 125
Glu Leu Arg His Phe Asp His Pro Asp Gly Ser Tyr Arg Ser Tyr Leu
                130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                    165                 170                 175
Arg Arg Ala Glu Gly Phe Glu Ala Arg Ser Gln Ala Ala Ala Pro
                180                 185                 190
Thr Ala Tyr Thr Pro Leu Asp Val Ala Gln Ala Tyr Gln Phe Pro Glu
                    195                 200                 205
Gly Leu Asp Gly Gln Gly Gln Cys Ile Ala Ile Ile Glu Leu Gly Gly
                210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                    245                 250                 255
Pro Thr Gly Asp Pro Lys Gly Pro Asp Gly Glu Val Glu Leu Asp Ile
                260                 265                 270
Glu Val Ala Gly Ala Leu Ala Pro Gly Ala Lys Phe Ala Val Tyr Phe
                275                 280                 285
Ala Pro Asp Thr Thr Ala Gly Phe Leu Asp Ala Ile Thr Thr Ala Ile
                290                 295                 300
His Asp Pro Thr Leu Lys Pro Ser Val Val Ser Ile Ser Trp Ser Gly
305                 310                 315                 320
Pro Glu Asp Ser Trp Thr Ser Ala Ala Ile Ala Ala Met Asn Arg Ala
                    325                 330                 335
Phe Leu Asp Ala Ala Leu Gly Val Thr Val Leu Ala Ala Ala Gly
                340                 345                 350
Asp Ser Gly Ser Thr Gly Gly Glu Gln Asp Gly Leu Tyr His Val His
                355                 360                 365
Phe Pro Ala Ala Ser Pro Tyr Val Leu Ala Cys Gly Gly Thr Arg Leu
                370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                    405                 410                 415
Pro Ala Trp Gln Glu His Ala Asn Val Pro Pro Ser Ala Asn Pro Gly
                420                 425                 430
Ala Ser Ser Gly Arg Gly Val Pro Asp Leu Ala Gly Asn Ala Asp Pro
                435                 440                 445
Gln Thr Gly Tyr Glu Val Val Ile Asp Gly Glu Ala Thr Val Ile Gly
                450                 455                 460
```

```
Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
            530                 535                 540

Leu Pro Ser Ala Ser Gln Pro Gln Pro
545                 550

<210> SEQ ID NO 30
<211> LENGTH: 553
<212> TYPE: PRT
<213> ORGANISM: Artificial Sequence
<220> FEATURE:
<223> OTHER INFORMATION: Synthetic

<400> SEQUENCE: 30

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
            115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
        210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270
```

```
Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
                340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
        370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
            435                 440                 445

Ala Thr Gly Tyr Glu Val Val Asp Gly Glu Ala Thr Val Thr Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro
545                 550

<210> SEQ ID NO 31
<211> LENGTH: 553
<212> TYPE: PRT
<213> ORGANISM: Artificial Sequence
<220> FEATURE:
<223> OTHER INFORMATION: Synthetic

<400> SEQUENCE: 31

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80
```

```
Ser His Gly Ala Ser Leu Asp Asp Phe Ala Glu Leu Arg Arg Phe Ala
                 85                  90                  95

Asp Ala His Gly Leu Ala Leu Asp Arg Ala Asn Val Ala Ala Gly Thr
            100                 105                 110

Ala Val Leu Ser Gly Pro Asp Ala Ile Asn Arg Ala Phe Gly Val
        115                 120                 125

Glu Leu Arg His Phe Asp His Pro Asp Gly Ser Tyr Arg Ser Tyr Leu
        130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Phe Glu Ala Arg Ser Gln Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
        210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
        290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
        370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Arg Val Thr Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495
```

-continued

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
        530                 535                 540

Leu Pro Ser Ala Ser Gln Pro Gln Pro
545                 550

<210> SEQ ID NO 32
<211> LENGTH: 553
<212> TYPE: PRT
<213> ORGANISM: Artificial Sequence
<220> FEATURE:
<223> OTHER INFORMATION: Synthetic

<400> SEQUENCE: 32

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Ala Ile Asn Arg Ala Phe Gly Val
        115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300

-continued

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
            325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
            370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ala Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln
545                 550

<210> SEQ ID NO 33
<211> LENGTH: 553
<212> TYPE: PRT
<213> ORGANISM: Artificial Sequence
<220> FEATURE:
<223> OTHER INFORMATION: Synthetic

<400> SEQUENCE: 33

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
            85                  90                  95

Asp Ala His Gly Leu Ala Leu Asp Arg Ala Asn Val Ala Ala Gly Thr
            100                 105                 110

```
Ala Val Leu Ser Gly Pro Asp Asp Ala Ile Asn Arg Ala Phe Gly Val
            115                 120                 125

Glu Leu Arg His Phe Asp His Pro Asp Gly Ser Tyr Arg Ser Tyr Leu
        130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
        290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Leu Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
```

```
                530                 535                 540
Leu Pro Ser Ala Ser Gln Pro Gln Pro
545                 550

<210> SEQ ID NO 34
<211> LENGTH: 553
<212> TYPE: PRT
<213> ORGANISM: Artificial Sequence
<220> FEATURE:
<223> OTHER INFORMATION: Synthetic

<400> SEQUENCE: 34

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
                35                  40                  45

Arg Gln Arg Ala Gly Glu Leu Ala Ala His Val Glu Arg Gln Ala Ala
            50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
                100                 105                 110

Ala Val Leu Ser Gly Pro Asp Asp Ala Ile Asn Arg Ala Phe Gly Val
                115                 120                 125

Glu Leu Arg His Phe Asp His Pro Asp Gly Ser Tyr Arg Ser Tyr Leu
                130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
                180                 185                 190

Thr Ala Tyr Thr Pro Leu Asp Val Ala Gln Ala Tyr Gln Phe Pro Glu
                195                 200                 205

Gly Leu Asp Gly Gln Gly Gln Cys Ile Ala Ile Ile Glu Leu Gly Gly
                210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
                260                 265                 270

Glu Val Ala Gly Ala Leu Ala Pro Gly Ala Lys Phe Ala Val Tyr Phe
                275                 280                 285

Ala Pro Asp Thr Thr Ala Gly Phe Leu Asp Ala Ile Thr Thr Ala Ile
                290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
```

```
            340                 345                 350
Asp Ser Gly Ser Thr Gly Gly Glu Gln Asp Gly Leu Tyr His Val His
        355                 360                 365
Phe Pro Ala Ala Ser Pro Tyr Val Leu Ala Cys Gly Gly Thr Arg Leu
    370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Ser Ala Asn Pro Gly
            420                 425                 430
Ala Ser Ser Gly Arg Gly Val Pro Asp Leu Ala Gly Asn Ala Asp Pro
        435                 440                 445
Ala Thr Gly Tyr Glu Val Val Ile Asp Gly Ala Thr Val Met Gly
    450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
                485                 490                 495
Gln Leu Pro Ala Asp Val Phe His Asp Ile Thr Glu Gly Asn Asn Asp
            500                 505                 510
Ile Ala Asn Arg Ala Gln Ile Tyr Gln Ala Gly Pro Gly Trp Asp Pro
        515                 520                 525
Cys Thr Gly Leu Gly Ser Pro Ile Gly Val Arg Leu Leu Gln Ala Leu
    530                 535                 540
Leu Pro Ser Ala Ser Gln Pro Gln Pro
545                 550

<210> SEQ ID NO 35
<211> LENGTH: 553
<212> TYPE: PRT
<213> ORGANISM: Artificial Sequence
<220> FEATURE:
<223> OTHER INFORMATION: Synthetic

<400> SEQUENCE: 35

Met Ser Asp Met Glu Lys Pro Trp Lys Glu Gly Glu Ala Arg Ala
1               5                   10                  15
Val Leu Gln Gly His Ala Arg Ala Gln Ala Pro Gln Ala Val Asp Lys
            20                  25                  30
Gly Pro Val Ala Gly Asp Glu Arg Met Ala Val Thr Val Leu Arg
        35                  40                  45
Arg Gln Arg Ala Gly Glu Leu Ala Ala His Val Glu Arg Gln Ala Ala
50                  55                  60
Ile Ala Pro His Ala Arg Glu His Leu Lys Arg Glu Ala Phe Ala Ala
65                  70                  75                  80
Ser His Gly Ala Ser Leu Asp Asp Phe Ala Glu Leu Arg Arg Phe Ala
                85                  90                  95
Asp Ala His Gly Leu Ala Leu Asp Arg Ala Asn Val Ala Ala Gly Thr
            100                 105                 110
Ala Val Leu Ser Gly Pro Asp Asp Ala Ile Asn Arg Ala Phe Gly Val
        115                 120                 125
Glu Leu Arg His Phe Asp His Pro Asp Gly Ser Tyr Arg Ser Tyr Leu
    130                 135                 140
Gly Glu Val Thr Val Pro Ala Ser Ile Ala Pro Met Ile Glu Ala Val
```

```
145                 150                 155                 160
Leu Gly Leu Asp Thr Arg Pro Val Ala Arg Pro His Phe Arg Met Gln
                165                 170                 175
Arg Arg Ala Glu Gly Gly Phe Glu Ala Arg Ser Gln Ala Ala Ala Pro
                180                 185                 190
Thr Ala Tyr Thr Pro Leu Asp Val Ala Gln Ala Tyr Gln Phe Pro Glu
                195                 200                 205
Gly Leu Asp Gly Gln Gly Gln Cys Ile Ala Ile Ile Glu Leu Gly Gly
                210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Lys Gly Pro Asp Gly Glu Val Glu Leu Asp Ile
                260                 265                 270
Glu Val Ala Gly Ala Leu Ala Pro Gly Ala Lys Phe Ala Val Tyr Phe
                275                 280                 285
Ala Pro Asp Thr Thr Ala Gly Phe Leu Asp Ala Ile Thr Thr Ala Ile
                290                 295                 300
His Asp Pro Thr Leu Lys Pro Ser Val Val Ser Ile Ser Trp Ser Gly
305                 310                 315                 320
Pro Glu Asp Ser Trp Thr Ser Ala Ala Ile Ala Ala Met Asn Arg Ala
                325                 330                 335
Phe Leu Asp Ala Ala Ala Leu Gly Val Thr Val Leu Ala Ala Ala Gly
                340                 345                 350
Asp Ser Gly Ser Thr Gly Gly Glu Gln Asp Gly Leu Tyr His Val His
                355                 360                 365
Phe Pro Ala Ala Ser Pro Tyr Val Leu Ala Cys Gly Gly Thr Arg Leu
                370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Pro Ser Ala Asn Pro Gly
                420                 425                 430
Ala Ser Ser Gly Arg Gly Val Pro Asp Leu Ala Gly Asn Ala Asp Pro
                435                 440                 445
Ala Thr Gly Tyr Glu Val Val Ile Asp Gly Glu Ala Thr Val Gln Gly
                450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
                485                 490                 495
Gln Leu Pro Ala Asp Val Phe His Asp Ile Thr Glu Gly Asn Asn Asp
                500                 505                 510
Ile Ala Asn Arg Ala Gln Ile Tyr Gln Ala Gly Pro Gly Trp Asp Pro
                515                 520                 525
Cys Thr Gly Leu Gly Ser Pro Ile Gly Val Arg Leu Leu Gln Ala Leu
                530                 535                 540
Leu Pro Ser Ala Ser Gln Pro Gln
545                 550
```

<210> SEQ ID NO 36

```
<211> LENGTH: 553
<212> TYPE: PRT
<213> ORGANISM: Artificial Sequence
<220> FEATURE:
<223> OTHER INFORMATION: Synthetic

<400> SEQUENCE: 36
```

Met Ser Asp Met Glu Lys Pro Trp Lys Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Ala Ile Asn Arg Ala Phe Gly Val
            115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
370                 375                 380

```
Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Arg Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro
545                 550

<210> SEQ ID NO 37
<211> LENGTH: 553
<212> TYPE: PRT
<213> ORGANISM: Artificial Sequence
<220> FEATURE:
<223> OTHER INFORMATION: Synthetic

<400> SEQUENCE: 37

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
            85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
            115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
            165                 170                 175

Arg Arg Ala Glu Gly Gly Phe Glu Ala Arg Ser Gln Ala Ala Ala Pro
            180                 185                 190
```

```
Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
            210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
            290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
            370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Thr Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro
545                 550

<210> SEQ ID NO 38
<211> LENGTH: 553
<212> TYPE: PRT
<213> ORGANISM: Artificial Sequence
<220> FEATURE:
<223> OTHER INFORMATION: Synthetic

<400> SEQUENCE: 38
```

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
            115                 120                 125

Glu Leu Arg His Phe Asp His Pro Asp Gly Ser Tyr Arg Ser Tyr Leu
        130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
        210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
            290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
            340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
        370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Gly Val Ser Arg Ile Phe Pro Leu
                405                 410                 415
```

```
Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Val Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro
545                 550
```

<210> SEQ ID NO 39
<211> LENGTH: 553
<212> TYPE: PRT
<213> ORGANISM: Artificial Sequence
<220> FEATURE:
<223> OTHER INFORMATION: Synthetic

<400> SEQUENCE: 39

```
Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220
```

Gly Tyr Asp Glu Ala Ser Leu Ala Gln Tyr Phe Ala Ser Leu Gly Val
225                 230                 235                 240

Pro Ala Pro Gln Val Ser Val Ser Val Asp Gly Ala Ser Asn Gln
            245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
            290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
                340                 345                 350

Asp Ser Gly Ser Thr Ser Gly Glu Gln Asp Gly Leu Tyr His Val His
            355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Thr Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro
545                 550

<210> SEQ ID NO 40
<211> LENGTH: 553
<212> TYPE: PRT
<213> ORGANISM: Artificial Sequence
<220> FEATURE:
<223> OTHER INFORMATION: Synthetic

<400> SEQUENCE: 40

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

```
Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
 50                  55                  60

Ile Ala Pro His Ala Arg Glu His Leu Lys Arg Glu Ala Phe Ala Ala
 65                  70                  75                  80

Ser His Gly Ala Ser Leu Asp Asp Phe Ala Glu Leu Arg Arg Phe Ala
                 85                  90                  95

Asp Ala His Gly Leu Ala Leu Asp Arg Ala Asn Val Ala Ala Gly Thr
            100                 105                 110

Ala Val Leu Ser Gly Pro Asp Ala Ile Asn Arg Ala Phe Gly Val
            115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Glu Gly Pro Asp Gly Glu Val Thr Leu Asp Ile
            260                 265                 270

Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Gly
            340                 345                 350

Asp Gln Gly Ser Thr Ser Gly Glu Gln Asp Gly Leu Tyr His Val His
            355                 360                 365

Phe Pro Ala Ala Ser Pro Tyr Val Leu Ala Cys Gly Thr Arg Leu
370                 375                 380

Val Ala Ser Gly Gly Arg Ile Ala Gln Glu Thr Val Trp Asn Gln Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
            435                 440                 445

Gln Thr Gly Tyr Glu Val Val Ile Asp Gly Glu Ala Thr Val Thr Gly
```

```
                    450                 455                 460
Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln
545                 550

<210> SEQ ID NO 41
<211> LENGTH: 553
<212> TYPE: PRT
<213> ORGANISM: Artificial Sequence
<220> FEATURE:
<223> OTHER INFORMATION: Synthetic

<400> SEQUENCE: 41

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Thr Leu Asp Ile
```

```
                260             265             270
Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
        290                 295                 300

His Asp Pro Thr Leu Lys Pro Ser Val Val Ser Ile Ser Trp Ala Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val Phe
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Gln Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Gln Thr Gly Tyr Glu Val Val Ile Asp Gly Glu Ala Thr Val Thr Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln
545                 550

<210> SEQ ID NO 42
<211> LENGTH: 553
<212> TYPE: PRT
<213> ORGANISM: Artificial Sequence
<220> FEATURE:
<223> OTHER INFORMATION: Synthetic

<400> SEQUENCE: 42

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
```

```
                65                  70                  75                  80
        Ser His Gly Ala Ser Leu Asp Asp Phe Ala Glu Leu Arg Arg Phe Ala
                            85                  90                  95

Asp Ala His Gly Leu Ala Leu Asp Arg Ala Asn Val Ala Ala Gly Thr
                        100                 105                 110

Ala Val Leu Ser Gly Pro Asp Ala Ile Asn Arg Ala Phe Gly Val
                    115                 120                 125

Glu Leu Arg His Phe Asp His Pro Asp Gly Ser Tyr Arg Ser Tyr Leu
                130                 135                 140

Gly Glu Val Thr Val Pro Ala Ser Ile Ala Pro Met Ile Glu Ala Val
        145                 150                 155                 160

Leu Gly Leu Asp Thr Arg Pro Val Ala Arg Pro His Phe Arg Met Gln
                        165                 170                 175

Arg Arg Ala Glu Gly Gly Phe Glu Ala Arg Ser Gln Ala Ala Pro
                    180                 185                 190

Thr Ala Tyr Thr Pro Leu Asp Val Ala Gln Ala Tyr Gln Phe Pro Glu
                        195                 200                 205

Gly Leu Asp Gly Gln Gly Gln Cys Ile Ala Ile Ile Glu Leu Gly Gly
                    210                 215                 220

Gly Tyr Asp Glu Ala Ser Leu Ala Gln Tyr Phe Ala Ser Leu Gly Val
        225                 230                 235                 240

Pro Ala Pro Gln Val Val Ser Val Ser Val Asp Gly Ala Ser Asn Gln
                        245                 250                 255

Pro Thr Gly Asp Pro Glu Gly Pro Asp Gly Glu Val Thr Val Asp Ile
                    260                 265                 270

Glu Val Ala Gly Ala Leu Ala Pro Gly Ala Lys Phe Ala Val Tyr Phe
                    275                 280                 285

Ala Pro Asp Thr Thr Ala Gly Phe Leu Asp Ala Ile Thr Thr Ala Ile
                    290                 295                 300

His Asp Pro Thr Leu Lys Pro Ser Val Val Ser Ile Ser Trp Ser Gly
        305                 310                 315                 320

Pro Glu Asp Ser Trp Thr Ser Ala Ala Ile Ala Ala Met Asn Arg Ala
                        325                 330                 335

Phe Leu Asp Ala Ala Ala Leu Gly Val Thr Val Leu Ala Ala Ala Gly
                    340                 345                 350

Asp Gln Gly Ser Thr Ser Gly Glu Gln Asp Gly Leu Tyr His Val His
                    355                 360                 365

Phe Pro Ala Ala Ser Pro Tyr Val Leu Ala Cys Gly Gly Thr Arg Leu
                370                 375                 380

Val Ala Ser Gly Gly Arg Ile Ala Gln Glu Thr Val Trp Asn Gln Gly
        385                 390                 395                 400

Pro Asp Gly Gly Ala Thr Gly Gly Val Ser Arg Ile Phe Pro Leu
                    405                 410                 415

Pro Ala Trp Gln Glu His Ala Asn Val Pro Ser Ala Asn Pro Gly
                        420                 425                 430

Ala Ser Ser Gly Arg Gly Val Pro Asp Leu Ala Gly Asn Ala Asp Pro
                    435                 440                 445

Gln Thr Gly Tyr Glu Val Val Ile Asp Gly Glu Ala Thr Val Ile Gly
                    450                 455                 460

Gly Thr Ser Ala Val Ala Pro Leu Phe Ala Ala Leu Val Ala Arg Ile
        465                 470                 475                 480

Asn Gln Lys Leu Gly Lys Ala Val Gly Tyr Leu Asn Pro Thr Leu Tyr
                        485                 490                 495
```

```
Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
        530                 535                 540

Leu Pro Ser Ala Ser Gln Pro Gln Pro
545                 550

<210> SEQ ID NO 43
<211> LENGTH: 581
<212> TYPE: PRT
<213> ORGANISM: Artificial Sequence
<220> FEATURE:
<223> OTHER INFORMATION: Synthetic

<400> SEQUENCE: 43

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Gly Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Ala Ile
    290                 295                 300
```

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
            325                 330                 335

Phe Leu Asp Ala Ala Leu Gly Val Thr Val Leu Ala Ala Gly
        340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Ser Ala Asn Pro Gly
        420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
    515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Ser Gly Ser Ser Gly
545                 550                 555                 560

Ser Gln Pro Gln Leu Pro Tyr Gly Ser Ser Gly Ser Ser Gly Ser His
                565                 570                 575

His His His His His
        580

<210> SEQ ID NO 44
<211> LENGTH: 553
<212> TYPE: PRT
<213> ORGANISM: Artificial Sequence
<220> FEATURE:
<223> OTHER INFORMATION: Synthetic

<400> SEQUENCE: 44

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

```
Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Phe Glu Ala Arg Ser Gln Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Glu Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495
```

```
Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
        530                 535                 540

Leu Pro Ser Ala Ser Gln Pro Gln Pro
545                 550

<210> SEQ ID NO 45
<211> LENGTH: 553
<212> TYPE: PRT
<213> ORGANISM: Artificial Sequence
<220> FEATURE:
<223> OTHER INFORMATION: Synthetic

<400> SEQUENCE: 45

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Ala His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Glu Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300
```

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
            325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
            370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln
545                 550

<210> SEQ ID NO 46
<211> LENGTH: 553
<212> TYPE: PRT
<213> ORGANISM: Artificial Sequence
<220> FEATURE:
<223> OTHER INFORMATION: Synthetic

<400> SEQUENCE: 46

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

```
Ala Val Leu Ser Gly Pro Asp Asp Ala Ile Asn Arg Ala Phe Gly Val
            115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Arg His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
            210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Glu Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
            290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
```

```
                    530                 535                 540
Leu Pro Ser Ala Ser Gln Pro Gln Pro
545                 550

<210> SEQ ID NO 47
<211> LENGTH: 553
<212> TYPE: PRT
<213> ORGANISM: Artificial Sequence
<220> FEATURE:
<223> OTHER INFORMATION: Synthetic

<400> SEQUENCE: 47

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
                35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
                100                 105                 110

Ala Val Leu Ser Gly Pro Asp Asp Ala Ile Asn Arg Ala Phe Gly Val
                115                 120                 125

Glu Leu Arg His Phe Asp His Pro Asp Gly Ser Tyr Arg Ser Tyr Leu
        130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Ser His Phe Arg Met Gln
                165                 170                 175

Arg Arg Ala Glu Gly Gly Phe Glu Ala Arg Ser Gln Ala Ala Ala Pro
                180                 185                 190

Thr Ala Tyr Thr Pro Leu Asp Val Ala Gln Ala Tyr Gln Phe Pro Glu
                195                 200                 205

Gly Leu Asp Gly Gln Gly Gln Cys Ile Ala Ile Ile Glu Leu Gly Gly
        210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Glu Gly Pro Asp Gly Glu Val Glu Leu Asp Ile
                260                 265                 270

Glu Val Ala Gly Ala Leu Ala Pro Gly Ala Lys Phe Ala Val Tyr Phe
                275                 280                 285

Ala Pro Asp Thr Thr Ala Gly Phe Leu Asp Ala Ile Thr Thr Ala Ile
                290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
```

```
                        340                 345                 350
Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
        370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Ser Ala Asn Pro Gly
        420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
        500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
        530                 535                 540

Leu Pro Ser Ala Ser Gln Pro Gln Pro
545                 550

<210> SEQ ID NO 48
<211> LENGTH: 553
<212> TYPE: PRT
<213> ORGANISM: Artificial Sequence
<220> FEATURE:
<223> OTHER INFORMATION: Synthetic

<400> SEQUENCE: 48

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
            85                  90                  95

Asp Ala His Gly Leu Ala Leu Asp Arg Ala Asn Val Ala Ala Gly Thr
        100                 105                 110

Ala Val Leu Ser Gly Pro Asp Asp Ala Ile Asn Arg Ala Phe Gly Val
            115                 120                 125

Glu Leu Arg His Phe Asp His Pro Asp Gly Ser Tyr Arg Ser Tyr Leu
        130                 135                 140

Gly Glu Val Thr Val Pro Ala Ser Ile Ala Pro Met Ile Glu Ala Val
```

```
            145                 150                 155                 160
Leu Gly Leu Asp Thr Arg Pro Val Ala Arg Pro Ala Phe Arg Met Gln
                165                 170                 175

Arg Arg Ala Glu Gly Gly Phe Glu Ala Arg Ser Gln Ala Ala Ala Pro
                180                 185                 190

Thr Ala Tyr Thr Pro Leu Asp Val Ala Gln Ala Tyr Gln Phe Pro Glu
                195                 200                 205

Gly Leu Asp Gly Gln Gly Gln Cys Ile Ala Ile Ile Glu Leu Gly Gly
            210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Glu Gly Pro Asp Gly Glu Val Glu Leu Asp Ile
                260                 265                 270

Glu Val Ala Gly Ala Leu Ala Pro Gly Ala Lys Phe Ala Val Tyr Phe
                275                 280                 285

Ala Pro Asp Thr Thr Ala Gly Phe Leu Asp Ala Ile Thr Thr Ala Ile
            290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
                340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
            370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
            530                 535                 540

Leu Pro Ser Ala Ser Gln Pro Gln
545                 550
```

<210> SEQ ID NO 49

<211> LENGTH: 553
<212> TYPE: PRT
<213> ORGANISM: Artificial Sequence
<220> FEATURE:
<223> OTHER INFORMATION: Synthetic

<400> SEQUENCE: 49

```
Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro Arg Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Glu Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380
```

```
Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
        420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
            530                 535                 540

Leu Pro Ser Ala Ser Gln Pro Gln Pro
545                 550

<210> SEQ ID NO 50
<211> LENGTH: 553
<212> TYPE: PRT
<213> ORGANISM: Artificial Sequence
<220> FEATURE:
<223> OTHER INFORMATION: Synthetic

<400> SEQUENCE: 50

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro Ser Phe Arg Met Gln
                165                 170                 175

Arg Arg Ala Glu Gly Gly Phe Glu Ala Arg Ser Gln Ala Ala Ala Pro
            180                 185                 190
```

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
        210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Glu Gly Pro Asp Gly Glu Val Glu Leu Asp Ile
                260                 265                 270

Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
        290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln
545                 550

<210> SEQ ID NO 51
<211> LENGTH: 553
<212> TYPE: PRT
<213> ORGANISM: Artificial Sequence
<220> FEATURE:
<223> OTHER INFORMATION: Synthetic

<400> SEQUENCE: 51

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Ala Ile Asn Arg Ala Phe Gly Val
        115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Arg Arg Met Gln
            165                 170                 175

Arg Arg Ala Glu Gly Phe Glu Ala Arg Ser Gln Ala Ala Pro
    180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
        210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
            245                 250                 255

Pro Thr Gly Asp Pro Glu Gly Pro Asp Gly Glu Val Glu Leu Asp Ile
        260                 265                 270

Glu Val Ala Gly Ala Leu Ala Pro Gly Ala Lys Phe Ala Val Tyr Phe
    275                 280                 285

Ala Pro Asp Thr Thr Ala Gly Phe Leu Asp Ala Ile Thr Thr Ala Ile
        290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
            325                 330                 335

Phe Leu Asp Ala Ala Leu Gly Val Thr Val Leu Ala Ala Ala Gly
        340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
        370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Gly Val Ser Arg Ile Phe Pro Leu
            405                 410                 415
```

Pro Ala Trp Gln Glu His Ala Asn Val Pro Pro Ser Ala Asn Pro Gly
             420                 425                 430

Ala Ser Ser Gly Arg Gly Val Pro Asp Leu Ala Gly Asn Ala Asp Pro
         435                 440                 445

Ala Thr Gly Tyr Glu Val Val Ile Asp Gly Glu Ala Thr Val Ile Gly
     450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                 485                 490                 495

Gln Leu Pro Ala Asp Val Phe His Asp Ile Thr Glu Gly Asn Asn Asp
             500                 505                 510

Ile Ala Asn Arg Ala Gln Ile Tyr Gln Ala Gly Pro Gly Trp Asp Pro
         515                 520                 525

Cys Thr Gly Leu Gly Ser Pro Ile Gly Val Arg Leu Leu Gln Ala Leu
     530                 535                 540

Leu Pro Ser Ala Ser Gln Pro Gln Pro
545                 550

<210> SEQ ID NO 52
<211> LENGTH: 553
<212> TYPE: PRT
<213> ORGANISM: Artificial Sequence
<220> FEATURE:
<223> OTHER INFORMATION: Synthetic

<400> SEQUENCE: 52

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
             20                  25                  30

Gly Pro Val Ala Gly Asp Glu Arg Met Ala Val Thr Val Leu Arg
         35                  40                  45

Arg Gln Arg Ala Gly Glu Leu Ala Ala His Val Glu Arg Gln Ala Ala
50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
             85                  90                  95

Asp Ala His Gly Leu Ala Leu Asp Arg Ala Asn Val Ala Ala Gly Thr
         100                 105                 110

Ala Val Leu Ser Gly Pro Asp Ala Ile Asn Arg Ala Phe Gly Val
     115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Ser Arg Met Gln
                 165                 170                 175

Arg Arg Ala Glu Gly Gly Phe Glu Ala Arg Ser Gln Ala Ala Ala Pro
             180                 185                 190

Thr Ala Tyr Thr Pro Leu Asp Val Ala Gln Ala Tyr Gln Phe Pro Glu
         195                 200                 205

Gly Leu Asp Gly Gln Gly Gln Cys Ile Ala Ile Ile Glu Leu Gly Gly
     210                 215                 220

Gly Tyr Asp Glu Ala Ser Leu Ala Gln Tyr Phe Ala Ser Leu Gly Val
225                 230                 235                 240

Pro Ala Pro Gln Val Ser Val Ser Val Asp Gly Ala Ser Asn Gln
            245                 250                 255

Pro Thr Gly Asp Pro Glu Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
            290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro
545                 550

<210> SEQ ID NO 53
<211> LENGTH: 553
<212> TYPE: PRT
<213> ORGANISM: Artificial Sequence
<220> FEATURE:
<223> OTHER INFORMATION: Synthetic

<400> SEQUENCE: 53

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

-continued

```
Gly Pro Val Ala Gly Asp Glu Arg Met Ala Val Thr Val Leu Arg
             35                  40                  45

Arg Gln Arg Ala Gly Glu Leu Ala Ala His Val Glu Arg Gln Ala Ala
 50                  55                  60

Ile Ala Pro His Ala Arg Glu His Leu Lys Arg Glu Ala Phe Ala Ala
 65                  70                  75                  80

Ser His Gly Ala Ser Leu Asp Asp Phe Ala Glu Leu Arg Arg Phe Ala
                 85                  90                  95

Asp Ala His Gly Leu Ala Leu Asp Arg Ala Asn Val Ala Ala Gly Thr
            100                 105                 110

Ala Val Leu Ser Gly Pro Asp Ala Ile Asn Arg Ala Phe Gly Val
            115                 120                 125

Glu Leu Arg His Phe Asp His Pro Asp Gly Ser Tyr Arg Ser Tyr Leu
            130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Ser Met Gln
                165                 170                 175

Arg Arg Ala Glu Gly Gly Phe Glu Ala Arg Ser Gln Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
            210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Glu Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Gly
            340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Thr Arg Leu
            370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
```

```
                    450                 455                 460
Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln
545                 550

<210> SEQ ID NO 54
<211> LENGTH: 553
<212> TYPE: PRT
<213> ORGANISM: Artificial Sequence
<220> FEATURE:
<223> OTHER INFORMATION: Synthetic

<400> SEQUENCE: 54

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Arg Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
```

```
                260                 265                 270
Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
        290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln
545                 550

<210> SEQ ID NO 55
<211> LENGTH: 553
<212> TYPE: PRT
<213> ORGANISM: Artificial Sequence
<220> FEATURE:
<223> OTHER INFORMATION: Synthetic

<400> SEQUENCE: 55

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
```

```
             65                  70                  75                  80
        Ser His Gly Ala Ser Leu Asp Asp Phe Ala Glu Leu Arg Arg Phe Ala
                            85                  90                  95
        Asp Ala His Gly Leu Ala Leu Asp Arg Ala Asn Val Ala Ala Gly Thr
                        100                 105                 110
        Ala Val Leu Ser Gly Pro Asp Ala Ile Asn Arg Ala Phe Gly Val
                    115                 120                 125
        Glu Leu Arg His Phe Asp His Pro Asp Gly Ser Tyr Arg Ser Tyr Leu
                130                 135                 140
        Gly Glu Val Thr Val Pro Ala Ser Ile Ala Pro Met Ile Glu Ala Val
        145                 150                 155                 160
        Leu Gly Leu Asp Thr Arg Pro Val Ala Arg Arg Phe Arg Met Gln
                        165                 170                 175
        Arg Arg Ala Glu Gly Gly Phe Glu Ala Arg Ser Gln Ala Ala Pro
                        180                 185                 190
        Thr Ala Tyr Thr Pro Leu Asp Val Ala Gln Ala Tyr Gln Phe Pro Glu
                    195                 200                 205
        Gly Leu Asp Gly Gln Gly Gln Cys Ile Ala Ile Ile Glu Leu Gly Gly
                210                 215                 220
        Gly Tyr Asp Glu Ala Ser Leu Ala Gln Tyr Phe Ala Ser Leu Gly Val
        225                 230                 235                 240
        Pro Ala Pro Gln Val Val Ser Val Ser Val Asp Gly Ala Ser Asn Gln
                        245                 250                 255
        Pro Thr Gly Asp Pro Lys Gly Pro Asp Gly Glu Val Glu Leu Asp Ile
                    260                 265                 270
        Glu Val Ala Gly Ala Leu Ala Pro Gly Ala Lys Phe Ala Val Tyr Phe
                275                 280                 285
        Ala Pro Asp Thr Thr Ala Gly Phe Leu Asp Ala Ile Thr Thr Ala Ile
                290                 295                 300
        His Asp Pro Thr Leu Lys Pro Ser Val Val Ser Ile Ser Trp Ser Gly
        305                 310                 315                 320
        Pro Glu Asp Ser Trp Thr Ser Ala Ala Ile Ala Ala Met Asn Arg Ala
                        325                 330                 335
        Phe Leu Asp Ala Ala Ala Leu Gly Val Thr Val Leu Ala Ala Ala Gly
                        340                 345                 350
        Asp Ser Gly Ser Thr Ser Gly Glu Gln Asp Gly Leu Tyr His Val His
                    355                 360                 365
        Phe Pro Ala Ala Ser Pro Tyr Val Leu Ala Cys Gly Gly Thr Arg Leu
                370                 375                 380
        Val Ala Ser Gly Gly Arg Ile Ala Gln Glu Thr Val Trp Asn Asp Gly
        385                 390                 395                 400
        Pro Asp Gly Gly Ala Thr Gly Gly Val Ser Arg Ile Phe Pro Leu
                        405                 410                 415
        Pro Ala Trp Gln Glu His Ala Asn Val Pro Ser Ala Asn Pro Gly
                        420                 425                 430
        Ala Ser Ser Gly Arg Gly Val Pro Asp Leu Ala Gly Asn Ala Asp Pro
                    435                 440                 445
        Ala Thr Gly Tyr Glu Val Val Ile Asp Gly Glu Ala Thr Val Thr Gly
                    450                 455                 460
        Gly Thr Ser Ala Val Ala Pro Leu Phe Ala Ala Leu Val Ala Arg Ile
        465                 470                 475                 480
        Asn Gln Lys Leu Gly Lys Ala Val Gly Tyr Leu Asn Pro Thr Leu Tyr
                        485                 490                 495
```

```
Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
        530                 535                 540

Leu Pro Ser Ala Ser Gln Pro Gln Pro
545                 550

<210> SEQ ID NO 56
<211> LENGTH: 553
<212> TYPE: PRT
<213> ORGANISM: Artificial Sequence
<220> FEATURE:
<223> OTHER INFORMATION: Synthetic

<400> SEQUENCE: 56

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Arg Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Glu Gly Pro Asp Gly Glu Val Thr Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Ala Ile
    290                 295                 300
```

```
His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
            325                 330                 335

Phe Leu Asp Ala Ala Leu Gly Val Thr Val Leu Ala Ala Gly
        340                 345                 350

Asp Gln Gly Ser Thr Ser Gly Glu Gln Asp Gly Leu Tyr His Val His
            355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Gln Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
            435                 440                 445

Gln Thr Gly Tyr Glu Val Val Ile Asp Gly Ala Thr Val Thr Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
            530                 535                 540

Leu Pro Ser Ala Ser Gln Pro Gln Pro
545                 550

<210> SEQ ID NO 57
<211> LENGTH: 553
<212> TYPE: PRT
<213> ORGANISM: Artificial Sequence
<220> FEATURE:
<223> OTHER INFORMATION: Synthetic

<400> SEQUENCE: 57

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
            50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110
```

```
Ala Val Leu Ser Gly Pro Asp Ala Ile Asn Arg Ala Phe Gly Val
        115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Arg Phe Arg Met Gln
                165                 170                 175

Arg Arg Ala Glu Gly Gly Phe Glu Ala Arg Ser Gln Ala Ala Ala Pro
                180                 185                 190

Thr Ala Tyr Thr Pro Leu Asp Val Ala Gln Ala Tyr Gln Phe Pro Glu
                195                 200                 205

Gly Leu Asp Gly Gln Gly Gln Cys Ile Ala Ile Ile Glu Leu Gly Gly
        210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Thr Leu Asp Ile
                260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
        290                 295                 300

His Asp Pro Thr Leu Lys Pro Ser Val Val Ser Ile Ser Trp Ala Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
                340                 345                 350

Asp Ser Gly Ser Thr Gly Gly Glu Gln Asp Gly Leu Tyr His Val Phe
        355                 360                 365

Phe Pro Ala Ala Ser Pro Tyr Val Leu Ala Cys Gly Gly Thr Arg Leu
        370                 375                 380

Val Ala Ser Gly Gly Arg Ile Ala Gln Glu Thr Val Trp Asn Gln Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
        435                 440                 445

Gln Thr Gly Tyr Glu Val Val Ile Asp Gly Glu Ala Thr Val Thr Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
                515                 520                 525
```

```
Cys Thr Gly Leu Gly Ser Pro Ile Gly Val Arg Leu Leu Gln Ala Leu
        530                 535                 540

Leu Pro Ser Ala Ser Gln Pro Gln Pro
545                 550

<210> SEQ ID NO 58
<211> LENGTH: 553
<212> TYPE: PRT
<213> ORGANISM: Artificial Sequence
<220> FEATURE:
<223> OTHER INFORMATION: Synthetic

<400> SEQUENCE: 58

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Ala Ile Asn Arg Ala Phe Gly Val
        115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Arg Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Glu Gly Pro Asp Gly Glu Val Thr Val Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335
```

```
Phe Leu Asp Ala Ala Leu Gly Val Thr Val Leu Ala Ala Ala Gly
                340                 345                 350

Asp Gln Gly Ser Thr Ser Gly Glu Gln Asp Gly Leu Tyr His Val His
            355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Gln Gly
385                 390                 395                 400

Pro Asp Gly Gly Ala Thr Gly Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
                435                 440                 445

Gln Thr Gly Tyr Glu Val Val Ile Asp Gly Glu Ala Thr Val Ile Gly
                450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
                515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro
545                 550

<210> SEQ ID NO 59
<211> LENGTH: 553
<212> TYPE: PRT
<213> ORGANISM: Artificial Sequence
<220> FEATURE:
<223> OTHER INFORMATION: Synthetic

<400> SEQUENCE: 59

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Ala Ile Asn Arg Ala Phe Gly Val
            115                 120                 125

Glu Leu Arg His Phe Asp His Pro Asp Gly Ser Tyr Arg Ser Tyr Leu
    130                 135                 140
```

-continued

Gly Glu Val Thr Val Pro Ala Ser Ile Ala Pro Met Ile Glu Ala Val
145                 150                 155                 160

Leu Gly Leu Asp Thr Arg Pro Val Ala Arg Arg Phe Arg Met Gln
            165                 170                 175

Arg Arg Ala Glu Gly Phe Glu Ala Arg Ser Gln Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Cys Ile Ala Ile Glu Leu Gly Gly
        210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
            245                 250                 255

Pro Thr Gly Asp Pro Glu Gly Pro Asp Gly Glu Val Thr Leu Asp Ile
            260                 265                 270

Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
290                 295                 300

His Asp Pro Thr Leu Lys Pro Ser Val Val Ser Ile Ser Trp Ser Met
305                 310                 315                 320

Pro Glu Asp Ser Trp Thr Ser Ala Ala Ile Ala Ala Met Asn Arg Ala
            325                 330                 335

Phe Leu Asp Ala Ala Leu Gly Val Thr Val Leu Ala Ala Gly
            340                 345                 350

Asp Gln Gly Ser Thr Ser Gly Glu Gln Asp Gly Leu Tyr His Val His
            355                 360                 365

Phe Pro Ala Ala Ser Pro Tyr Val Leu Ala Cys Gly Gly Thr Arg Leu
            370                 375                 380

Val Ala Ser Gly Gly Arg Ile Ala Gln Glu Thr Val Trp Asn Gln Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
            435                 440                 445

Gln Thr Gly Tyr Glu Val Val Ile Asp Gly Glu Ala Thr Val Thr Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
            530                 535                 540

Leu Pro Ser Ala Ser Gln Pro Gln Pro
545                 550

-continued

```
<210> SEQ ID NO 60
<211> LENGTH: 553
<212> TYPE: PRT
<213> ORGANISM: Artificial Sequence
<220> FEATURE:
<223> OTHER INFORMATION: Synthetic

<400> SEQUENCE: 60

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Arg Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Thr Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Ser Ile Ser Trp Ala Met
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
            340                 345                 350

Asp Ser Gly Ser Thr Gly Gly Glu Gln Asp Gly Leu Tyr His Val Phe
        355                 360                 365

Phe Pro Ala Ala Ser Pro Tyr Val Leu Ala Cys Gly Gly Thr Arg Leu
```

```
                370                 375                 380
Val Ala Ser Gly Gly Arg Ile Ala Gln Glu Thr Val Trp Asn Gln Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
            435                 440                 445

Gln Thr Gly Tyr Glu Val Val Ile Asp Gly Glu Ala Thr Val Thr Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro
545                 550

<210> SEQ ID NO 61
<211> LENGTH: 15
<212> TYPE: PRT
<213> ORGANISM: Artificial Sequence
<220> FEATURE:
<223> OTHER INFORMATION: Synthetic

<400> SEQUENCE: 61

Pro Gln Gln Pro Ile Pro Gln Gln Pro Gln Pro Tyr Pro Gln Gln
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic

<400> SEQUENCE: 62

Gln Pro Phe Pro Gln Gln Pro Glu Gln Ile Ile Pro Gln Gln Pro
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic

<400> SEQUENCE: 63

Leu Gln Pro Phe Pro Gln Pro Gln Leu Pro Tyr Pro Gln Pro Gln
1               5                   10                  15

<210> SEQ ID NO 64
<211> LENGTH: 14
<212> TYPE: PRT
<213> ORGANISM: Artificial Sequence
```

```
<220> FEATURE:
<223> OTHER INFORMATION: Synthetic

<400> SEQUENCE: 64

Gln Pro Phe Pro Gln Pro Gln Gln Pro Phe Pro Trp Gln Pro
1               5                   10

<210> SEQ ID NO 65
<211> LENGTH: 4
<212> TYPE: PRT
<213> ORGANISM: Artificial Sequence
<220> FEATURE:
<223> OTHER INFORMATION: Synthetic

<400> SEQUENCE: 65

Pro Gln Leu Pro
1

<210> SEQ ID NO 66
<211> LENGTH: 4
<212> TYPE: PRT
<213> ORGANISM: Artificial Sequence
<220> FEATURE:
<223> OTHER INFORMATION: Synthetic

<400> SEQUENCE: 66

Pro Gln Gln Pro
1

<210> SEQ ID NO 67
<211> LENGTH: 9
<212> TYPE: PRT
<213> ORGANISM: Artificial Sequence
<220> FEATURE:
<223> OTHER INFORMATION: Synthetic

<400> SEQUENCE: 67

Pro Phe Pro Gln Pro Gln Leu Pro Tyr
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic

<400> SEQUENCE: 68

Pro Phe Pro Gln Pro Gln Gln Pro Phe
1               5

<210> SEQ ID NO 69
<211> LENGTH: 33
<212> TYPE: PRT
<213> ORGANISM: Artificial Sequence
<220> FEATURE:
<223> OTHER INFORMATION: Synthetic

<400> SEQUENCE: 69

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe
```

```
<210> SEQ ID NO 70
<211> LENGTH: 26
<212> TYPE: PRT
<213> ORGANISM: Artificial Sequence
<220> FEATURE:
<223> OTHER INFORMATION: Synthetic

<400> SEQUENCE: 70

Phe Leu Gln Pro Gln Gln Pro Phe Pro Gln Gln Pro Gln Gln Pro Tyr
1               5                   10                  15

Pro Gln Gln Pro Gln Gln Pro Phe Pro Gln
            20                  25

<210> SEQ ID NO 71
<211> LENGTH: 363
<212> TYPE: PRT
<213> ORGANISM: Artificial Sequence
<220> FEATURE:
<223> OTHER INFORMATION: Synthetic

<400> SEQUENCE: 71

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285
```

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln
                355                 360
```

<210> SEQ ID NO 72
<211> LENGTH: 364
<212> TYPE: PRT
<213> ORGANISM: Artificial Sequence
<220> FEATURE:
<223> OTHER INFORMATION: Synthetic

<400> SEQUENCE: 72

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Glu Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285
```

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
                355                 360

<210> SEQ ID NO 73
<211> LENGTH: 364
<212> TYPE: PRT
<213> ORGANISM: Artificial Sequence
<220> FEATURE:
<223> OTHER INFORMATION: Synthetic

<400> SEQUENCE: 73

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Ala Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
        290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                    325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360

<210> SEQ ID NO 74
<211> LENGTH: 364
<212> TYPE: PRT
<213> ORGANISM: Artificial Sequence
<220> FEATURE:
<223> OTHER INFORMATION: Synthetic

<400> SEQUENCE: 74

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Ser Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
                355                 360
```

<210> SEQ ID NO 75
<211> LENGTH: 364
<212> TYPE: PRT
<213> ORGANISM: Artificial Sequence
<220> FEATURE:
<223> OTHER INFORMATION: Synthetic

<400> SEQUENCE: 75

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Ser Val Ser Val Asp Gly Ala
    50                  55                  60

Ser Asn Gln Pro Thr Gly Asp Pro Lys Gly Pro Asp Gly Glu Thr Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285
```

```
Ala Arg Ile Asn Gln Lys Leu Gly Lys Ala Val Gly Tyr Leu Asn Pro
        290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                    325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
        355                 360
```

<210> SEQ ID NO 76
<211> LENGTH: 364
<212> TYPE: PRT
<213> ORGANISM: Artificial Sequence
<220> FEATURE:
<223> OTHER INFORMATION: Synthetic

<400> SEQUENCE: 76

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Leu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285
```

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
                355                 360
```

<210> SEQ ID NO 77
<211> LENGTH: 364
<212> TYPE: PRT
<213> ORGANISM: Artificial Sequence
<220> FEATURE:
<223> OTHER INFORMATION: Synthetic

<400> SEQUENCE: 77

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
        50                  55                  60

Ser Asn Gln Pro Thr Gly Asp Pro Lys Gly Pro Asp Gly Glu Val Thr
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
                100                 105                 110

Thr Ala Ile His Asp Pro Thr Leu Lys Pro Ser Val Val Ser Ile Ser
            115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
                180                 185                 190

Thr Arg Leu Val Ala Ser Gly Gly Arg Ile Ala Gln Glu Thr Val Trp
            195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
            275                 280                 285
```

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360

<210> SEQ ID NO 78
<211> LENGTH: 364
<212> TYPE: PRT
<213> ORGANISM: Artificial Sequence
<220> FEATURE:
<223> OTHER INFORMATION: Synthetic

<400> SEQUENCE: 78

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Ala Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360

<210> SEQ ID NO 79
<211> LENGTH: 364
<212> TYPE: PRT
<213> ORGANISM: Artificial Sequence
<220> FEATURE:
<223> OTHER INFORMATION: Synthetic

<400> SEQUENCE: 79

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Thr Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285
```

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
    355                 360

<210> SEQ ID NO 80
<211> LENGTH: 364
<212> TYPE: PRT
<213> ORGANISM: Artificial Sequence
<220> FEATURE:
<223> OTHER INFORMATION: Synthetic

<400> SEQUENCE: 80

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Val Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

```
Ala Arg Ile Asn Gln Lys Leu Gly Lys Ala Val Gly Tyr Leu Asn Pro
        290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                    325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
        355                 360

<210> SEQ ID NO 81
<211> LENGTH: 364
<212> TYPE: PRT
<213> ORGANISM: Artificial Sequence
<220> FEATURE:
<223> OTHER INFORMATION: Synthetic

<400> SEQUENCE: 81

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                    85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Ser Ile Ser
        115                 120                 125

Trp Ala Gly Pro Glu Asp Ser Trp Thr Ser Ala Ala Ile Ala Ala Met
130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                    165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                    245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285
```

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                    325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360

<210> SEQ ID NO 82
<211> LENGTH: 364
<212> TYPE: PRT
<213> ORGANISM: Artificial Sequence
<220> FEATURE:
<223> OTHER INFORMATION: Synthetic

<400> SEQUENCE: 82

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ala Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360

<210> SEQ ID NO 83
<211> LENGTH: 364
<212> TYPE: PRT
<213> ORGANISM: Artificial Sequence
<220> FEATURE:
<223> OTHER INFORMATION: Synthetic

<400> SEQUENCE: 83

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Glu Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
                355                 360
```

<210> SEQ ID NO 84
<211> LENGTH: 364
<212> TYPE: PRT
<213> ORGANISM: Artificial Sequence
<220> FEATURE:
<223> OTHER INFORMATION: Synthetic

<400> SEQUENCE: 84

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
        50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
                100                 105                 110

Thr Ala Ile His Asp Pro Thr Leu Lys Pro Ser Val Val Ser Ile Ser
            115                 120                 125

Trp Ser Gly Pro Glu Asp Ser Trp Thr Ser Ala Ala Ile Ala Ala Met
        130                 135                 140

Asn Arg Ala Phe Leu Asp Ala Ala Ala Leu Gly Val Thr Val Leu Ala
145                 150                 155                 160

Ala Ala Gly Asp Gln Gly Ser Thr Gly Gly Glu Gln Asp Gly Leu Tyr
                165                 170                 175

His Val His Phe Pro Ala Ala Ser Pro Tyr Val Leu Ala Cys Gly Gly
                180                 185                 190

Thr Arg Leu Val Ala Ser Gly Gly Arg Ile Ala Gln Glu Thr Val Trp
            195                 200                 205

Asn Asp Gly Pro Asp Gly Gly Ala Thr Gly Gly Gly Val Ser Arg Ile
        210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
            275                 280                 285
```

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                    325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360

<210> SEQ ID NO 85
<211> LENGTH: 364
<212> TYPE: PRT
<213> ORGANISM: Artificial Sequence
<220> FEATURE:
<223> OTHER INFORMATION: Synthetic

<400> SEQUENCE: 85

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Arg Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
        355                 360
```

<210> SEQ ID NO 86
<211> LENGTH: 364
<212> TYPE: PRT
<213> ORGANISM: Artificial Sequence
<220> FEATURE:
<223> OTHER INFORMATION: Synthetic

<400> SEQUENCE: 86

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Tyr Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285
```

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
                355                 360

<210> SEQ ID NO 87
<211> LENGTH: 364
<212> TYPE: PRT
<213> ORGANISM: Artificial Sequence
<220> FEATURE:
<223> OTHER INFORMATION: Synthetic

<400> SEQUENCE: 87

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Asn Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
                355                 360

<210> SEQ ID NO 88
<211> LENGTH: 364
<212> TYPE: PRT
<213> ORGANISM: Artificial Sequence
<220> FEATURE:
<223> OTHER INFORMATION: Synthetic

<400> SEQUENCE: 88

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
                100                 105                 110

Thr Ala Ile His Asp Pro Thr Leu Lys Pro Ser Val Val Ser Ile Ser
            115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Ser Gly Glu Gln Asp Gly Leu Tyr
                165                 170                 175

His Val His Phe Pro Ala Ala Ser Pro Tyr Val Leu Ala Cys Gly Gly
                180                 185                 190

Thr Arg Leu Val Ala Ser Gly Gly Arg Ile Ala Gln Glu Thr Val Trp
            195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360

<210> SEQ ID NO 89
<211> LENGTH: 364
<212> TYPE: PRT
<213> ORGANISM: Artificial Sequence
<220> FEATURE:
<223> OTHER INFORMATION: Synthetic

<400> SEQUENCE: 89

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gln Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
                355                 360

<210> SEQ ID NO 90
<211> LENGTH: 364
<212> TYPE: PRT
<213> ORGANISM: Artificial Sequence
<220> FEATURE:
<223> OTHER INFORMATION: Synthetic

<400> SEQUENCE: 90

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Thr Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360
```

<210> SEQ ID NO 91
<211> LENGTH: 364
<212> TYPE: PRT
<213> ORGANISM: Artificial Sequence
<220> FEATURE:
<223> OTHER INFORMATION: Synthetic

<400> SEQUENCE: 91

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val Phe Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285
```

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360

<210> SEQ ID NO 92
<211> LENGTH: 364
<212> TYPE: PRT
<213> ORGANISM: Artificial Sequence
<220> FEATURE:
<223> OTHER INFORMATION: Synthetic

<400> SEQUENCE: 92

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val Gln Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
                355                 360
```

<210> SEQ ID NO 93
<211> LENGTH: 364
<212> TYPE: PRT
<213> ORGANISM: Artificial Sequence
<220> FEATURE:
<223> OTHER INFORMATION: Synthetic

<400> SEQUENCE: 93

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Gln Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285
```

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
        355                 360

<210> SEQ ID NO 94
<211> LENGTH: 364
<212> TYPE: PRT
<213> ORGANISM: Artificial Sequence
<220> FEATURE:
<223> OTHER INFORMATION: Synthetic

<400> SEQUENCE: 94

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Gln Gly Pro Ser Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
                355                 360
```

<210> SEQ ID NO 95
<211> LENGTH: 364
<212> TYPE: PRT
<213> ORGANISM: Artificial Sequence
<220> FEATURE:
<223> OTHER INFORMATION: Synthetic

<400> SEQUENCE: 95

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
        50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
                100                 105                 110

Thr Ala Ile His Asp Pro Thr Leu Lys Pro Ser Val Val Ser Ile Ser
            115                 120                 125

Trp Ser Gly Pro Glu Asp Ser Trp Thr Ser Ala Ala Ile Ala Ala Met
        130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
                180                 185                 190

Thr Arg Leu Val Ala Ser Gly Gly Arg Ile Ala Gln Glu Thr Val Trp
            195                 200                 205

Asn Gln Gly Pro Gln Gly Gly Ala Thr Gly Gly Gly Val Ser Arg Ile
        210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
            275                 280                 285
```

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360

<210> SEQ ID NO 96
<211> LENGTH: 364
<212> TYPE: PRT
<213> ORGANISM: Artificial Sequence
<220> FEATURE:
<223> OTHER INFORMATION: Synthetic

<400> SEQUENCE: 96

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Gln Gly Pro Gln Gly Gly Ala Ser Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
        355                 360

<210> SEQ ID NO 97
<211> LENGTH: 364
<212> TYPE: PRT
<213> ORGANISM: Artificial Sequence
<220> FEATURE:
<223> OTHER INFORMATION: Synthetic

<400> SEQUENCE: 97

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Gln Gly Pro Gln Gly Gly Ala Ser Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
                355                 360

<210> SEQ ID NO 98
<211> LENGTH: 364
<212> TYPE: PRT
<213> ORGANISM: Artificial Sequence
<220> FEATURE:
<223> OTHER INFORMATION: Synthetic

<400> SEQUENCE: 98

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Glu Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
        290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
        355                 360

<210> SEQ ID NO 99
<211> LENGTH: 364
<212> TYPE: PRT
<213> ORGANISM: Artificial Sequence
<220> FEATURE:
<223> OTHER INFORMATION: Synthetic

<400> SEQUENCE: 99

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Gln Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
        355                 360

<210> SEQ ID NO 100
<211> LENGTH: 364
<212> TYPE: PRT
<213> ORGANISM: Artificial Sequence
<220> FEATURE:
<223> OTHER INFORMATION: Synthetic

<400> SEQUENCE: 100

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Val Asp Gly Glu Ala Thr
            260                 265                 270

Val Thr Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
                355                 360

<210> SEQ ID NO 101
<211> LENGTH: 364
<212> TYPE: PRT
<213> ORGANISM: Artificial Sequence
<220> FEATURE:
<223> OTHER INFORMATION: Synthetic

<400> SEQUENCE: 101

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Arg
            260                 265                 270

Val Thr Gly Gly Thr Ser Ala Val Ala Pro Leu Phe Ala Ala Leu Val
        275                 280                 285

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
        355                 360

<210> SEQ ID NO 102
<211> LENGTH: 364
<212> TYPE: PRT
<213> ORGANISM: Artificial Sequence
<220> FEATURE:
<223> OTHER INFORMATION: Synthetic

<400> SEQUENCE: 102

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ala Gly Gly Thr Ser Ala Val Ala Pro Leu Phe Ala Ala Leu Val
        275                 280                 285
```

```
Ala Arg Ile Asn Gln Lys Leu Gly Lys Ala Val Gly Tyr Leu Asn Pro
        290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
        355                 360
```

<210> SEQ ID NO 103
<211> LENGTH: 364
<212> TYPE: PRT
<213> ORGANISM: Artificial Sequence
<220> FEATURE:
<223> OTHER INFORMATION: Synthetic

<400> SEQUENCE: 103

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Leu Gly Gly Thr Ser Ala Val Ala Pro Leu Phe Ala Ala Leu Val
        275                 280                 285
```

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                    325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360

<210> SEQ ID NO 104
<211> LENGTH: 364
<212> TYPE: PRT
<213> ORGANISM: Artificial Sequence
<220> FEATURE:
<223> OTHER INFORMATION: Synthetic

<400> SEQUENCE: 104

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Met Gly Gly Thr Ser Ala Val Ala Pro Leu Phe Ala Ala Leu Val
        275                 280                 285

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360

<210> SEQ ID NO 105
<211> LENGTH: 364
<212> TYPE: PRT
<213> ORGANISM: Artificial Sequence
<220> FEATURE:
<223> OTHER INFORMATION: Synthetic

<400> SEQUENCE: 105

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Gln Gly Gly Thr Ser Ala Val Ala Pro Leu Phe Ala Ala Leu Val
        275                 280                 285
```

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                    325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360
```

<210> SEQ ID NO 106
<211> LENGTH: 364
<212> TYPE: PRT
<213> ORGANISM: Artificial Sequence
<220> FEATURE:
<223> OTHER INFORMATION: Synthetic

<400> SEQUENCE: 106

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Arg Gly Gly Thr Ser Ala Val Ala Pro Leu Phe Ala Ala Leu Val
        275                 280                 285
```

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                    325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360
```

<210> SEQ ID NO 107
<211> LENGTH: 364
<212> TYPE: PRT
<213> ORGANISM: Artificial Sequence
<220> FEATURE:
<223> OTHER INFORMATION: Synthetic

<400> SEQUENCE: 107

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Thr Gly Gly Thr Ser Ala Val Ala Pro Leu Phe Ala Ala Leu Val
        275                 280                 285
```

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
            325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
        355                 360

<210> SEQ ID NO 108
<211> LENGTH: 364
<212> TYPE: PRT
<213> ORGANISM: Artificial Sequence
<220> FEATURE:
<223> OTHER INFORMATION: Synthetic

<400> SEQUENCE: 108

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Val Gly Gly Thr Ser Ala Val Ala Pro Leu Phe Ala Ala Leu Val
        275                 280                 285

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360
```

<210> SEQ ID NO 109
<211> LENGTH: 364
<212> TYPE: PRT
<213> ORGANISM: Artificial Sequence
<220> FEATURE:
<223> OTHER INFORMATION: Synthetic

<400> SEQUENCE: 109

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Ser Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Thr Gly Gly Thr Ser Ala Val Ala Pro Leu Phe Ala Ala Leu Val
        275                 280                 285
```

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
                355                 360

<210> SEQ ID NO 110
<211> LENGTH: 364
<212> TYPE: PRT
<213> ORGANISM: Artificial Sequence
<220> FEATURE:
<223> OTHER INFORMATION: Synthetic

<400> SEQUENCE: 110

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Glu Gly Pro Asp Gly Glu Val Thr
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Gln Gly Ser Thr Ser Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Gln Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Gln Thr Gly Tyr Glu Val Val Ile Asp Gly Glu Ala Thr
            260                 265                 270

Val Thr Gly Gly Thr Ser Ala Val Ala Pro Leu Phe Ala Ala Leu Val
        275                 280                 285

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360

<210> SEQ ID NO 111
<211> LENGTH: 364
<212> TYPE: PRT
<213> ORGANISM: Artificial Sequence
<220> FEATURE:
<223> OTHER INFORMATION: Synthetic

<400> SEQUENCE: 111

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Thr
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ala Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val Phe Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Gln Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Gln Thr Gly Tyr Glu Val Val Ile Asp Gly Glu Ala Thr
            260                 265                 270

Val Thr Gly Gly Thr Ser Ala Val Ala Pro Leu Phe Ala Ala Leu Val
        275                 280                 285
```

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
        355                 360

<210> SEQ ID NO 112
<211> LENGTH: 364
<212> TYPE: PRT
<213> ORGANISM: Artificial Sequence
<220> FEATURE:
<223> OTHER INFORMATION: Synthetic

<400> SEQUENCE: 112

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Glu Gly Pro Asp Gly Glu Val Thr
65                  70                  75                  80

Val Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Gln Gly Ser Thr Ser Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Gln Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Gln Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
                355                 360

<210> SEQ ID NO 113
<211> LENGTH: 392
<212> TYPE: PRT
<213> ORGANISM: Artificial Sequence
<220> FEATURE:
<223> OTHER INFORMATION: Synthetic

<400> SEQUENCE: 113

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
        50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
                100                 105                 110

Thr Ala Ile His Asp Pro Thr Leu Lys Pro Ser Val Val Ser Ile Ser
            115                 120                 125

Trp Ser Gly Pro Glu Asp Ser Trp Thr Ser Ala Ala Ile Ala Ala Met
        130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
                180                 185                 190

Thr Arg Leu Val Ala Ser Gly Gly Arg Ile Ala Gln Glu Thr Val Trp
            195                 200                 205

Asn Asp Gly Pro Asp Gly Gly Ala Thr Gly Gly Gly Val Ser Arg Ile
        210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                    325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro Gly Ser Ser Gly
            355                 360                 365

Ser Ser Gly Ser Gln Pro Gln Leu Pro Tyr Gly Ser Ser Gly Ser Ser
370                 375                 380

Gly Ser His His His His His His
385                 390

<210> SEQ ID NO 114
<211> LENGTH: 364
<212> TYPE: PRT
<213> ORGANISM: Artificial Sequence
<220> FEATURE:
<223> OTHER INFORMATION: Synthetic

<400> SEQUENCE: 114

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Glu Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

```
Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
        355                 360

<210> SEQ ID NO 115
<211> LENGTH: 364
<212> TYPE: PRT
<213> ORGANISM: Artificial Sequence
<220> FEATURE:
<223> OTHER INFORMATION: Synthetic

<400> SEQUENCE: 115

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Glu Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255
```

Ala Asp Pro Ala Thr Gly Tyr Glu Val Val Ile Asp Gly Glu Ala Thr
              260                 265                 270

Val Ile Gly Gly Thr Ser Ala Val Ala Pro Leu Phe Ala Ala Leu Val
          275                 280                 285

Ala Arg Ile Asn Gln Lys Leu Gly Lys Ala Val Gly Tyr Leu Asn Pro
      290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                  325                 330                 335

Trp Asp Pro Cys Thr Gly Leu Gly Ser Pro Ile Gly Val Arg Leu Leu
              340                 345                 350

Gln Ala Leu Leu Pro Ser Ala Ser Gln Pro Gln Pro
          355                 360

<210> SEQ ID NO 116
<211> LENGTH: 364
<212> TYPE: PRT
<213> ORGANISM: Artificial Sequence
<220> FEATURE:
<223> OTHER INFORMATION: Synthetic

<400> SEQUENCE: 116

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Glu Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Arg Ile Ala Gln Glu Thr Val Trp
        195                 200                 205

Asn Asp Gly Pro Asp Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

-continued

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
        355                 360

<210> SEQ ID NO 117
<211> LENGTH: 364
<212> TYPE: PRT
<213> ORGANISM: Artificial Sequence
<220> FEATURE:
<223> OTHER INFORMATION: Synthetic

<400> SEQUENCE: 117

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Glu Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

```
Ala Asp Pro Ala Thr Gly Tyr Glu Val Val Ile Asp Gly Glu Ala Thr
        260                 265                 270

Val Ile Gly Gly Thr Ser Ala Val Ala Pro Leu Phe Ala Ala Leu Val
    275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
        355                 360

<210> SEQ ID NO 118
<211> LENGTH: 364
<212> TYPE: PRT
<213> ORGANISM: Artificial Sequence
<220> FEATURE:
<223> OTHER INFORMATION: Synthetic

<400> SEQUENCE: 118

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Glu Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255
```

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln
            355                 360

<210> SEQ ID NO 119
<211> LENGTH: 364
<212> TYPE: PRT
<213> ORGANISM: Artificial Sequence
<220> FEATURE:
<223> OTHER INFORMATION: Synthetic

<400> SEQUENCE: 119

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
        50                  55                  60

Ser Asn Gln Pro Thr Gly Asp Pro Glu Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
            115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
            195                 200                 205

Asn Asp Gly Pro Asp Gly Ala Thr Gly Gly Gly Val Ser Arg Ile
        210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

```
Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
        355                 360

<210> SEQ ID NO 120
<211> LENGTH: 364
<212> TYPE: PRT
<213> ORGANISM: Artificial Sequence
<220> FEATURE:
<223> OTHER INFORMATION: Synthetic

<400> SEQUENCE: 120

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Glu Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255
```

```
Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
        290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
            355                 360

<210> SEQ ID NO 121
<211> LENGTH: 363
<212> TYPE: PRT
<213> ORGANISM: Artificial Sequence
<220> FEATURE:
<223> OTHER INFORMATION: Synthetic

<400> SEQUENCE: 121

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Glu Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255
```

Ala Asp Pro Ala Thr Gly Tyr Glu Val Val Ile Asp Gly Glu Ala Thr
              260                 265                 270

Val Ile Gly Gly Thr Ser Ala Val Ala Pro Leu Phe Ala Ala Leu Val
          275                 280                 285

Ala Arg Ile Asn Gln Lys Leu Gly Lys Ala Val Gly Tyr Leu Asn Pro
      290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln
            355                 360

<210> SEQ ID NO 122
<211> LENGTH: 364
<212> TYPE: PRT
<213> ORGANISM: Artificial Sequence
<220> FEATURE:
<223> OTHER INFORMATION: Synthetic

<400> SEQUENCE: 122

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Glu Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

```
Ala Asp Pro Ala Thr Gly Tyr Glu Val Val Ile Asp Gly Glu Ala Thr
        260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
        290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
            355                 360
```

<210> SEQ ID NO 123
<211> LENGTH: 364
<212> TYPE: PRT
<213> ORGANISM: Artificial Sequence
<220> FEATURE:
<223> OTHER INFORMATION: Synthetic

<400> SEQUENCE: 123

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Glu Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255
```

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
            355                 360

<210> SEQ ID NO 124
<211> LENGTH: 364
<212> TYPE: PRT
<213> ORGANISM: Artificial Sequence
<220> FEATURE:
<223> OTHER INFORMATION: Synthetic

<400> SEQUENCE: 124

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

```
Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
            355                 360

<210> SEQ ID NO 125
<211> LENGTH: 364
<212> TYPE: PRT
<213> ORGANISM: Artificial Sequence
<220> FEATURE:
<223> OTHER INFORMATION: Synthetic

<400> SEQUENCE: 125

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Ser Gly Ser Thr Ser Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255
```

```
Ala Asp Pro Ala Thr Gly Tyr Glu Val Val Ile Asp Gly Glu Ala Thr
            260                 265                 270

Val Thr Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
        355                 360
```

<210> SEQ ID NO 126
<211> LENGTH: 364
<212> TYPE: PRT
<213> ORGANISM: Artificial Sequence
<220> FEATURE:
<223> OTHER INFORMATION: Synthetic

<400> SEQUENCE: 126

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Glu Gly Pro Asp Gly Glu Val Thr
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Gln Gly Ser Thr Ser Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Gln Gly Pro Asp Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255
```

```
Ala Asp Pro Gln Thr Gly Tyr Glu Val Val Ile Asp Gly Glu Ala Thr
            260                 265                 270

Val Thr Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
            355                 360

<210> SEQ ID NO 127
<211> LENGTH: 364
<212> TYPE: PRT
<213> ORGANISM: Artificial Sequence
<220> FEATURE:
<223> OTHER INFORMATION: Synthetic

<400> SEQUENCE: 127

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Thr
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ala Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val Phe Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Gln Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255
```

Ala Asp Pro Gln Thr Gly Tyr Glu Val Val Ile Asp Gly Glu Ala Thr
            260                 265                 270

Val Thr Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
            355                 360

<210> SEQ ID NO 128
<211> LENGTH: 364
<212> TYPE: PRT
<213> ORGANISM: Artificial Sequence
<220> FEATURE:
<223> OTHER INFORMATION: Synthetic

<400> SEQUENCE: 128

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Glu Gly Pro Asp Gly Glu Val Thr
65                  70                  75                  80

Val Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Gln Gly Ser Thr Ser Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Gln Gly Pro Asp Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

```
Ala Asp Pro Gln Thr Gly Tyr Glu Val Val Ile Asp Gly Glu Ala Thr
        260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
        290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
        355                 360
```

<210> SEQ ID NO 129
<211> LENGTH: 364
<212> TYPE: PRT
<213> ORGANISM: Artificial Sequence
<220> FEATURE:
<223> OTHER INFORMATION: Synthetic

<400> SEQUENCE: 129

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Glu Gly Pro Asp Gly Glu Val Thr
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Met Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Gln Gly Ser Thr Ser Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Gln Gly Pro Asp Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255
```

-continued

```
Ala Asp Pro Gln Thr Gly Tyr Glu Val Val Ile Asp Gly Glu Ala Thr
            260                 265                 270

Val Thr Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
        290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
        355                 360

<210> SEQ ID NO 130
<211> LENGTH: 364
<212> TYPE: PRT
<213> ORGANISM: Artificial Sequence
<220> FEATURE:
<223> OTHER INFORMATION: Synthetic

<400> SEQUENCE: 130

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Thr
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ala Met Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val Phe Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Gln Gly Pro Asp Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255
```

Ala Asp Pro Gln Thr Gly Tyr Glu Val Val Ile Asp Gly Glu Ala Thr
            260                 265                 270

Val Thr Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
        355                 360

<210> SEQ ID NO 131
<211> LENGTH: 60
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(25)
<223> OTHER INFORMATION: Xaa is any amino acid
<220> FEATURE:
<221> NAME/KEY: MISC_FEATURE
<222> LOCATION: (28)..(28)
<223> OTHER INFORMATION: Xaa is L or Q
<220> FEATURE:
<221> NAME/KEY: MISC_FEATURE
<222> LOCATION: (30)..(55)
<223> OTHER INFORMATION: Xaa is any amino acid

<400> SEQUENCE: 131

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Pro Gln Xaa Pro Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa His His His His His His
    50                  55                  60

<210> SEQ ID NO 132
<211> LENGTH: 28
<212> TYPE: PRT
<213> ORGANISM: Artificial Sequence
<220> FEATURE:
<223> OTHER INFORMATION: Synthetic

<400> SEQUENCE: 132

Gly Ser Ser Gly Ser Ser Gly Ser Gln Pro Gln Leu Pro Tyr Gly Ser
1               5                   10                  15

Ser Gly Ser Ser Gly Ser His His His His His His
            20                  25

<210> SEQ ID NO 133
<211> LENGTH: 15
<212> TYPE: PRT
<213> ORGANISM: Artificial Sequence
<220> FEATURE:
<223> OTHER INFORMATION: Synthetic

<400> SEQUENCE: 133

Leu Gln Pro Phe Pro Gln Pro Gln Leu Pro Tyr Pro Gln Pro Gln
1               5                   10                  15

<210> SEQ ID NO 134
<211> LENGTH: 14
<212> TYPE: PRT
<213> ORGANISM: Artificial Sequence
<220> FEATURE:
<223> OTHER INFORMATION: Synthetic

<400> SEQUENCE: 134

Gln Pro Phe Pro Gln Pro Gln Gln Pro Phe Pro Trp Gln Pro
1               5                   10

<210> SEQ ID NO 135
<211> LENGTH: 5
<212> TYPE: PRT
<213> ORGANISM: Artificial Sequence
<220> FEATURE:
<223> OTHER INFORMATION: Synthetic

<400> SEQUENCE: 135

Gln Gln Pro Phe Pro
1               5

<210> SEQ ID NO 136
<211> LENGTH: 6
<212> TYPE: PRT
<213> ORGANISM: Artificial Sequence
<220> FEATURE:
<223> OTHER INFORMATION: Synthetic

<400> SEQUENCE: 136

Gln Pro Gln Leu Pro Tyr
1               5

<210> SEQ ID NO 137
<211> LENGTH: 9
<212> TYPE: PRT
<213> ORGANISM: Artificial Sequence
<220> FEATURE:
<223> OTHER INFORMATION: Synthetic

<400> SEQUENCE: 137

Leu Pro Tyr Pro Gln Pro Gln Pro Phe
1               5

<210> SEQ ID NO 138
<211> LENGTH: 5
<212> TYPE: PRT
<213> ORGANISM: Artificial Sequence
<220> FEATURE:
<223> OTHER INFORMATION: Synthetic

<400> SEQUENCE: 138

Phe Leu Gln Pro Gln
1               5

<210> SEQ ID NO 139
<211> LENGTH: 20
<212> TYPE: PRT
<213> ORGANISM: Artificial Sequence
<220> FEATURE:
<223> OTHER INFORMATION: Synthetic

<400> SEQUENCE: 139

Gly Ser Thr Glu Asn Leu Tyr Phe Gln Ser Gly Ala Leu Glu His His
1               5                   10                  15

His His His His
            20

<210> SEQ ID NO 140
<211> LENGTH: 8
<212> TYPE: PRT
<213> ORGANISM: Artificial Sequence
<220> FEATURE:
<223> OTHER INFORMATION: Synthetic

<400> SEQUENCE: 140

Pro Phe Gln Pro Gln Leu Pro Tyr
1               5

<210> SEQ ID NO 141
<211> LENGTH: 9
<212> TYPE: PRT
<213> ORGANISM: Artificial Sequence
<220> FEATURE:
<223> OTHER INFORMATION: Synthetic

<400> SEQUENCE: 141

Pro Phe Pro Gln Pro Gln Leu Pro Tyr
1               5

<210> SEQ ID NO 142
<211> LENGTH: 9
<212> TYPE: PRT
<213> ORGANISM: Artificial Sequence
<220> FEATURE:
<223> OTHER INFORMATION: Synthetic

<400> SEQUENCE: 142

Pro Gln Pro Gln Leu Pro Tyr Pro Gln
1               5

<210> SEQ ID NO 143
<211> LENGTH: 9
<212> TYPE: PRT
<213> ORGANISM: Artificial Sequence
<220> FEATURE:
<223> OTHER INFORMATION: Synthetic

<400> SEQUENCE: 143

Pro Phe Pro Gln Pro Gln Gln Pro Phe
1               5

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Pro Gln Pro Gln Gln Pro Phe Pro Trp
1               5

<210> SEQ ID NO 145
<211> LENGTH: 9
<212> TYPE: PRT
<213> ORGANISM: Artificial Sequence
<220> FEATURE:
<223> OTHER INFORMATION: Synthetic

```
<400> SEQUENCE: 145

Ile Gln Pro Gln Gln Pro Ala Gln Leu
1               5

<210> SEQ ID NO 146
<211> LENGTH: 9
<212> TYPE: PRT
<213> ORGANISM: Artificial Sequence
<220> FEATURE:
<223> OTHER INFORMATION: Synthetic

<400> SEQUENCE: 146

Pro Gln Gln Ser Phe Pro Gln Gln Gln
1               5

<210> SEQ ID NO 147
<211> LENGTH: 5
<212> TYPE: PRT
<213> ORGANISM: Artificial Sequence
<220> FEATURE:
<223> OTHER INFORMATION: Synthetic

<400> SEQUENCE: 147

Gln Pro Tyr Pro Gln
1               5

<210> SEQ ID NO 148
<211> LENGTH: 6
<212> TYPE: PRT
<213> ORGANISM: Artificial Sequence
<220> FEATURE:
<223> OTHER INFORMATION: Synthetic

<400> SEQUENCE: 148

Pro Phe Pro Gln Pro Gln
1               5

<210> SEQ ID NO 149
<211> LENGTH: 7
<212> TYPE: PRT
<213> ORGANISM: Artificial Sequence
<220> FEATURE:
<223> OTHER INFORMATION: Synthetic

<400> SEQUENCE: 149

Glu Asn Leu Tyr Phe Gln Ser
1               5

<210> SEQ ID NO 150
<211> LENGTH: 553
<212> TYPE: PRT
<213> ORGANISM: Artificial Sequence
<220> FEATURE:
<223> OTHER INFORMATION: Synthetic

<400> SEQUENCE: 150

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
    50                  55                  60
```

```
Ile Ala Pro His Ala Arg Glu His Leu Lys Arg Glu Ala Phe Ala Ala
 65                  70                  75                  80

Ser His Gly Ala Ser Leu Asp Asp Phe Ala Glu Leu Arg Arg Phe Ala
                 85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Phe Glu Ala Arg Ser Gln Ala Ala Ala Pro
                180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Glu Gly Pro Asp Gly Glu Val Thr Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Met
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Gln Gly Ser Thr Ser Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Gln Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
        435                 440                 445

Gln Thr Gly Tyr Glu Val Val Ile Asp Gly Glu Ala Thr Val Thr Gly
    450                 455                 460

Gly Thr Ser Ala Val Ala Pro Leu Phe Ala Ala Leu Val Ala Arg Ile
465                 470                 475                 480
```

```
Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
            530                 535                 540

Leu Pro Ser Ala Ser Gln Pro Gln Pro
545                 550
```

<210> SEQ ID NO 151
<211> LENGTH: 364
<212> TYPE: PRT
<213> ORGANISM: Artificial Sequence
<220> FEATURE:
<223> OTHER INFORMATION: Synthetic

<400> SEQUENCE: 151

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Ser Val Ser Val Asp Gly Ala
    50                  55                  60

Ser Asn Gln Pro Thr Gly Asp Pro Glu Gly Pro Asp Gly Glu Val Thr
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Met Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Gln Gly Ser Thr Ser Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Gln Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Gln Thr Gly Tyr Glu Val Val Ile Asp Gly Glu Ala Thr
            260                 265                 270

Val Thr Gly Gly Thr Ser Ala Val Ala Pro Leu Phe Ala Ala Leu Val
        275                 280                 285
```

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
                355                 360

<210> SEQ ID NO 152
<211> LENGTH: 553
<212> TYPE: PRT
<213> ORGANISM: Artificial Sequence
<220> FEATURE:
<223> OTHER INFORMATION: Synthetic

<400> SEQUENCE: 152

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Asp Ala Ile Asn Arg Ala Phe Gly Val
            115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Thr Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
290                 295                 300

His Asp Pro Thr Leu Lys Pro Ser Val Val Ser Ile Ser Trp Ala Met
305                 310                 315                 320

Pro Glu Asp Ser Trp Thr Ser Ala Ala Ile Ala Ala Met Asn Arg Ala
            325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val Phe
        355                 360                 365

Phe Pro Ala Ala Ser Pro Tyr Val Leu Ala Cys Gly Thr Arg Leu
370                 375                 380

Val Ala Ser Gly Gly Arg Ile Ala Gln Glu Thr Val Trp Asn Gln Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Gln Thr Gly Tyr Glu Val Val Ile Asp Gly Glu Ala Thr Val Thr Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
530                 535                 540

Leu Pro Ser Ala Ser Gln Pro Gln
545                 550

<210> SEQ ID NO 153
<211> LENGTH: 364
<212> TYPE: PRT
<213> ORGANISM: Artificial Sequence
<220> FEATURE:
<223> OTHER INFORMATION: Synthetic

<400> SEQUENCE: 153

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Thr
65                  70                  75                  80

Leu Asp Ile Glu Val Ala Gly Ala Leu Ala Pro Gly Ala Lys Phe Ala
                85                  90                  95

```
Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
            115                 120                 125

Trp Ala Met Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val Phe Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Gln Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Gln Thr Gly Tyr Glu Val Val Ile Asp Gly Glu Ala Thr
            260                 265                 270

Val Thr Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
        355                 360

<210> SEQ ID NO 154
<211> LENGTH: 553
<212> TYPE: PRT
<213> ORGANISM: Artificial Sequence
<220> FEATURE:
<223> OTHER INFORMATION: Synthetic

<400> SEQUENCE: 154

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95
```

```
Asp Ala His Gly Leu Ala Leu Asp Arg Ala Asn Val Ala Ala Gly Thr
            100                 105                 110
Ala Val Leu Ser Gly Pro Asp Ala Ile Asn Arg Ala Phe Gly Val
        115                 120                 125
Glu Leu Arg His Phe Asp His Pro Asp Gly Ser Tyr Arg Ser Tyr Leu
    130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                165                 170                 175
Arg Arg Ala Glu Gly Gly Phe Glu Ala Arg Ser Gln Ala Ala Ala Pro
            180                 185                 190
Thr Ala Tyr Thr Pro Leu Asp Val Ala Gln Ala Tyr Gln Phe Pro Glu
        195                 200                 205
Gly Leu Asp Gly Gln Gly Gln Cys Ile Ala Ile Ile Glu Leu Gly Gly
    210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Lys Gly Pro Asp Gly Glu Val Glu Leu Asp Ile
            260                 265                 270
Glu Val Ala Gly Ala Leu Ala Pro Gly Ala Lys Phe Ala Val Tyr Phe
        275                 280                 285
Ala Pro Asp Thr Thr Ala Gly Phe Leu Asp Ala Ile Thr Thr Ala Ile
    290                 295                 300
His Asp Pro Thr Leu Lys Pro Ser Val Val Ser Ile Ser Trp Ser Gly
305                 310                 315                 320
Pro Glu Asp Ser Trp Thr Ser Ala Ala Ile Ala Ala Met Asn Arg Ala
                325                 330                 335
Phe Leu Asp Ala Ala Ala Leu Gly Val Thr Val Leu Ala Ala Ala Gly
            340                 345                 350
Asp Ser Gly Ser Thr Ser Gly Glu Gln Asp Gly Leu Tyr His Val His
        355                 360                 365
Phe Pro Ala Ala Ser Pro Tyr Val Leu Ala Cys Gly Gly Thr Arg Leu
    370                 375                 380
Val Ala Ser Gly Gly Arg Ile Ala Gln Glu Thr Val Trp Asn Gln Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Pro Ser Ala Asn Pro Gly
            420                 425                 430
Ala Ser Ser Gly Arg Gly Val Pro Asp Leu Ala Gly Asn Ala Asp Pro
        435                 440                 445
Gln Thr Gly Tyr Glu Val Val Ile Asp Gly Glu Ala Thr Val Thr Gly
    450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
                485                 490                 495
Gln Leu Pro Ala Asp Val Phe His Asp Ile Thr Glu Gly Asn Asn Asp
            500                 505                 510
Ile Ala Asn Arg Ala Gln Ile Tyr Gln Ala Gly Pro Gly Trp Asp Pro
```

```
            515                 520                 525
Cys Thr Gly Leu Gly Ser Pro Ile Gly Val Arg Leu Leu Gln Ala Leu
        530                 535                 540

Leu Pro Ser Ala Ser Gln Pro Gln Pro
545                 550

<210> SEQ ID NO 155
<211> LENGTH: 364
<212> TYPE: PRT
<213> ORGANISM: Artificial Sequence
<220> FEATURE:
<223> OTHER INFORMATION: synthetic

<400> SEQUENCE: 155

Ala Ala Pro Thr Ala Tyr Thr Pro Leu Asp Val Ala Gln Ala Tyr Gln
1               5                  10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Ser Gly Ser Thr Ser Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Arg Ile Ala Gln Glu Thr Val Trp
        195                 200                 205

Asn Gln Gly Pro Asp Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Gln Thr Gly Tyr Glu Val Val Ile Asp Gly Glu Ala Thr
            260                 265                 270

Val Thr Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
```

```
                      325                 330                 335
Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro
            355                 360
```

<210> SEQ ID NO 156
<211> LENGTH: 6
<212> TYPE: PRT
<213> ORGANISM: Artificial Sequence
<220> FEATURE:
<223> OTHER INFORMATION: synthetic

<400> SEQUENCE: 156

```
Pro Gln Pro Gln Leu Pro
1               5
```